United States Patent [19]

Oinuma et al.

[11] Patent Number: 5,281,626

[45] Date of Patent: Jan. 25, 1994

[54] BENZENESULFONAMIDE DERIVATIVES

[75] Inventors: Hitoshi Oinuma; Takashi Hasegawa; Tadanobu Takamura; Kenichi Nomoto; Yoshiharu Daiku; Toshihiko Naito, all of Ibaraki; Sachiyuki Hamano, Kanagawa, all of Japan

[73] Assignee: Eisai Co., Ltd., Tokyo, Japan

[21] Appl. No.: 768,515

[22] PCT Filed: Feb. 7, 1991

[86] PCT No.: PCT/JP91/00149

§ 371 Date: Sep. 26, 1991

§ 102(e) Date: Sep. 26, 1991

[87] PCT Pub. No.: WO91/12237

PCT Pub. Date: Aug. 22, 1991

[30] Foreign Application Priority Data

Feb. 8, 1990 [JP] Japan .................. 2-27071

[51] Int. Cl.$^5$ .................. C07C 311/46; A61K 31/18
[52] U.S. Cl. .................. 514/603; 540/575; 540/597; 540/606; 544/335; 546/133; 546/171; 546/208; 546/223; 546/280; 546/337; 548/193; 548/568; 558/391; 560/138; 562/428; 564/86
[58] Field of Search .................. 514/603; 564/86; 562/428; 560/138; 558/391; 548/193, 568; 540/133, 171, 208, 223, 280, 337, 575, 597, 606; 544/335

[56] References Cited

U.S. PATENT DOCUMENTS 4,925,861 5/1990 Hayashi et al. .................. 514/603
4,992,469 2/1991 Ozawa et al. .................. 514/603

FOREIGN PATENT DOCUMENTS 0227431 7/1987 European Pat. Off. ..
0248597 12/1987 European Pat. Off. ..
0255749 12/1985 Japan .
2175466 8/1987 Japan .
63-2968 1/1988 Japan .
3258854 10/1988 Japan .

OTHER PUBLICATIONS

Islam, Egyptian J. Chem. 17, 689, (1974).
Teofino, Gazz Chim. Ital. 89, 1200 (1959).
Naoya Yoda et al.: Journal of Polymer Science Part A, vol. 3 (6) 2229–2242 (1965) Abstract.
R. J. Cremlyn et al.: J. Chem. Soc. Pak., vol. 7, No. 2, 1985, pp. 111–124.

Primary Examiner—Robert Gerstl
Attorney, Agent, or Firm—Birch, Stewart, Kolasch & Birch

[57] ABSTRACT

A novel benzenesulfonamide derivative represented by the formula:

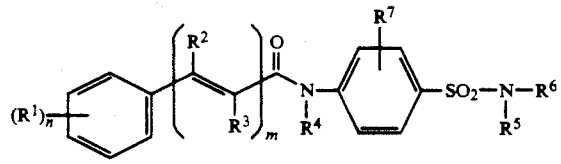

has an inhibitory activity against phospholipase $A_2$, so that it is effective in the treatment of diseases for which such an activity is efficacious.

17 Claims, No Drawings

BENZENESULFONAMIDE DERIVATIVES

TECHNICAL FIELD

The present invention relates to a benzenesulfonamide derivative or a pharmacologically acceptable salt thereof exhibiting excellent activity as a drug.

BACKGROUND ART

Phospholipase A is an enzyme catalyzing the hydrolysis of the acyl linkage of glycerophospholipid and includes phospholipase A catalyzing the hydrolysis of 1-ester linkage of glycerophospholipid and phospholipase $A_2$ catalyzing that of 2-ester linkage thereof. Although both of the phospholipases are widely distributed in the biological world, they have recently been noted from the standpoint of their connection to various diseases.

For example, in ischemic diseases such as cardiac infarction, it is believed that phospholipase is activated to disintegrate membrane phospholipid, giving an increased infarct size. Furthermore, studies have been made on the connection of the phospholipase to other various troubles.

Under these circumstances, various phospholipase $A_2$ inhibitors have been proposed from the standpoint that the inhibition of phospholipase, particularly phospholipase $A_2$ ($PLA_2$) is effective in the prevention and treatment of various diseases (see Japanese Patent Laid-Open Nos. 255,749/1985, 175,466/1987, 2,968/1988 and 258,854/1988).

The inventors of the present invention have eagerly studied for many years on substances which can inhibit phospholipase $A_2$ to find out that a benzenesulfonamide derivative or a pharmacologically acceptable salt thereof which will be described below exhibits a high inhibitory activity against phospholipase $A_2$ and therefore is useful in the prevention and treatment of various diseases, for example, ischemic diseases such as cardiac infarction. The present invention has been accomplished on the basis of this finding.

DISCLOSURE OF INVENTION

The compound of the present invention is a sulfonamide derivative represented by the following formula (I) or a pharmacologically acceptable salt thereof:

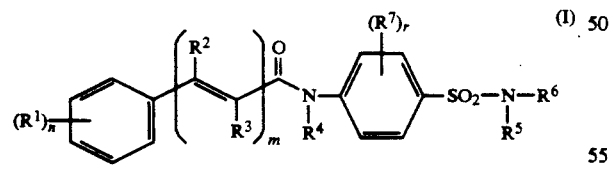

wherein a plurality of $R^1$ groups each independently stand for a hydrogen atom, a cyano, nitro or hydroxyl group, a halogen atom, a lower alkoxy group, an acyloxy group, a group represented by the formula: $-SO_2-R^8$ (wherein $R^8$ stands for a lower alkyl group), a heteroaryl or glycyloxy group or a group represented by the formula:

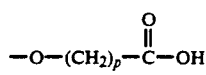

wherein p is an integer of 1 to 3), and n is an integer of 1 to 4;

$R^2$ stands for a hydrogen atom or a pyridyl group;
$R^3$ stands for a hydrogen atom or a lower alkyl, cyano or pyridyl group;
$R^4$ stands for a hydrogen atom or a lower alkyl group;
$R^5$ and $R^6$ may be the same or different from each other and each stand for a hydrogen atom, a lower alkyl group, a group represented by the formula: $-(CH_2)_q-A$ [wherein q is an integer of 1 to 4; and A stands for a hydroxyl group, a group represented by the formula:

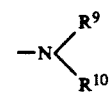

(wherein $R^9$ and $R^{10}$ may be the same or different from each other and each stand for a hydrogen atom or a lower alkyl group), a group represented by the formula:

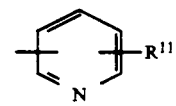

(wherein $R^{11}$ stands for a hydrogen atom or a lower alkyl group) or a group represented by the formula:

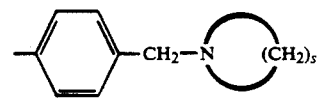

wherein s is an integer of 2 to 5)], an unsubstituted or substituted cycloalkyl group, a bicycloalkyl, tricycloalkyl or azabicycloalkyl group or a group represented by the formula:

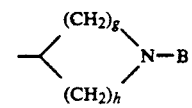

(wherein g and h are each an integer of 1 to 4; and B stands for a lower alkyl group, a substituted or unsubstituted arylalkyl group or a substituted or unsubstituted pyridyl alkyl group), or alternatively $R^5$ and $R^6$ may be combined together to form a 6- or 7-membered ring which may contain a nitrogen or oxygen atom in addition to the nitrogen atom to which $R^5$ and $R^6$ are bonded, and said 6- or 7-membered ring may be substituted with a lower alkyl, arylalkyl, cycloalkylalkyl or heteroarylalkyl group;

a plurality of $R^7$ groups each independently stand for a hydrogen atom, a lower alkyl group, a lower alkoxy group or a halogen atom; and r is an integer of 1 or 2, provided that when r is 2, the two $R^7$ groups may form a ring together with two adjacent carbon atoms constituting the benzene ring; and m is an integer of 1 or 2.

In the above definition of the compound (I) according to the present invention, the lower alkyl group defined with respect to $R^3$, $R^4$, $R^5$, $R^6$, $R^7$, $R^{11}$ and B is a straight chain or branched alkyl group having 1 to 6 carbon atoms and examples thereof include methyl, ethyl, propyl, isopropyl, butyl, isobutyl, sec-butyl, tert-butyl, pentyl(amyl), isopentyl, neopentyl, tert-pentyl, 1-methylbutyl, 2-methylbutyl, 1,2-dimethylpropyl, hexyl, isohexyl, 1 methylpentyl, 2-methylpentyl, 3-methylpentyl, 1,1-dimethylbutyl, 1,2-dimethylbutyl, 2,2 dimethylbutyl, 1,3 dimethylbutyl, 2,3 dimethylbutyl, 3,3-dimethylbutyl, 1-ethylbutyl, 2-ethylbutyl, 1,1,2-trimethylpropyl, 1,2,2 trimethyl propyl, 1-ethyl-1 methylpropyl and 1-ethyl-2-methylpropyl groups. Among these groups, methyl, ethyl, propyl and isopropyl groups are desirable, among which methyl group is most desirable.

The lower alkoxy group defined with respect to $R^1$ and $R^2$ is one derived from the above-mentioned lower alkyl group having 1 to 6 carbon atoms and preferable examples thereof include methoxy, ethoxy, n-propoxy, isopropoxy and n-butoxy groups.

The halogen atom defined with respect to $R^1$ and $R^7$ is chlorine, bromine, iodine or fluorine.

The acyloxy group defined with respect to $R^1$ is a group wherein an oxygen atom is bonded to an acyl group which is a residue of an organic acid such as aliphatic saturated or unsaturated carboxylic acid or carbocyclic or heterocyclic carboxylic acid, and particular examples of the acyl group include lower alkanoyl groups such as formyl, acetyl, propionyl, butyryl, isobutylryl, valeryl, isovaleryl and pivaloyl groups; aroyl groups such as benzoyl, toluoyl and naphthoyl groups; and heteroaroyl groups such as furoyl, nicotinoyl and isonicotinoyl groups.

Among the groups represented by the formula —SO$_2$—R$^8$ in the definition of $R^1$, methylsulfonyl group which corresponds to a group represented by the formula wherein $R^8$ is a methyl group is most desirable.

The heteroaryl group defined with respect to $R^1$ is a group derived from a heterocycle containing a nitrogen, oxygen or sulfur atom. Particular examples thereof include pyridyl, furyl and imidazolyl groups, among which imidazolyl group is most desirable.

Among the groups represented by the formula:

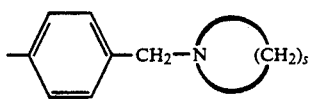

(wherein s is an integer of 2 to 5) in the definition of $R^5$ and $R^6$, a group represented thereby wherein s is 4 or 5 is most desirable.

That is, a group represented by the above formula wherein the group represented by the formula:

is one represented by the formula:

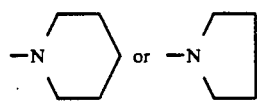

is most desirable.

The unsubstituted cycloalkyl group defined with respect to $R^5$ and $R^6$ includes cyclopropyl, cyclobutyl, cyclopentyl, cyclohexyl, cycloheptyl, cyclooctyl, cyclononyl, cyclodecyl and cyclododecyl groups.

The substituted cycloalkyl group is a cycloalkyl group as described above which is either substituted with a lower alkyl group such as a methyl group or a halogen atom or condensed with an aromatic ring such as a benzene ring or a heterocyclic ring such as a pyridine ring at adjacent carbon atoms constituting the cyclcoalkyl group to form a condensed ring group represented by the formula:

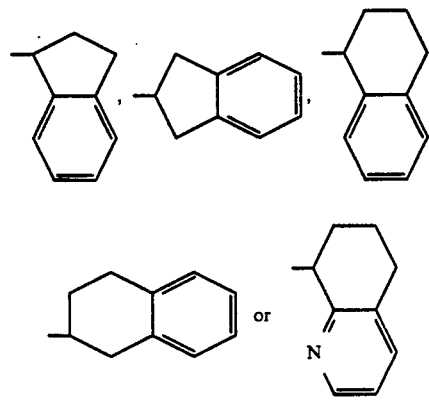

The bicycloalkyl or tricycloalkyl group is an aliphatic saturated hydrocarbon group which is composed only of two or three rings with at least two carbon atoms being jointly owned by the rings.

Representative examples of the bicycloalkyl group include

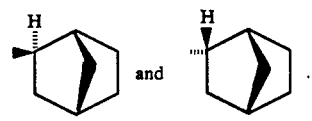

The tricycloalkyl group is, for example, an adamantyl group.

The azabicycloalkyl group is a bicycloalkyl group described above in which one of the carbon atoms constituting the bicycloalkyl group is replaced by a nitrogen atom. Examples thereof include

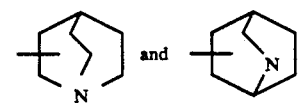

In the formula:

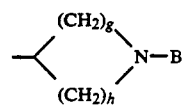

in the definition of $R^5$ and $R^6$, g and h are each an integer of 1 to 4. Examples of the group represented by the formula include

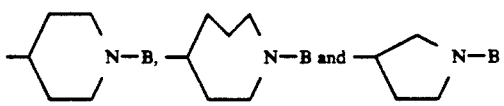

The substituted or unsubstituted arylalkyl group defined with respect to B is one derived from an aryl group (such as a phenyl or naphthyl group) which may be substituted with a lower alkyl group such as a methyl or ethyl group, a halogen atom or a lower alkoxy group such as a methoxy group and examples thereof include benzyl and phenethyl groups. Further, the substituted or unsubstituted pyridylalkyl group defined with respect thereto is one derived from a pyridyl group which may be substituted with a lower alkyl group such as a methyl or ethyl group, a halogen atom or a lower alkoxy group such as a methoxy group. Preferable examples of the group represented by the above formula include

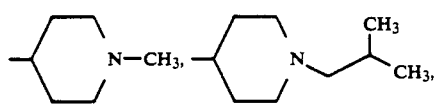

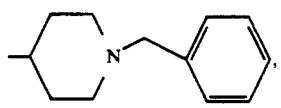

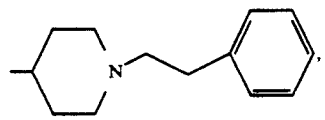

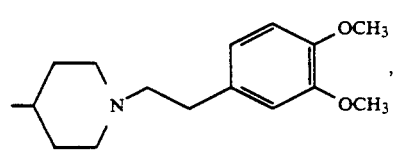

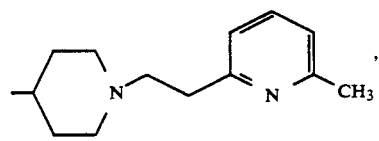

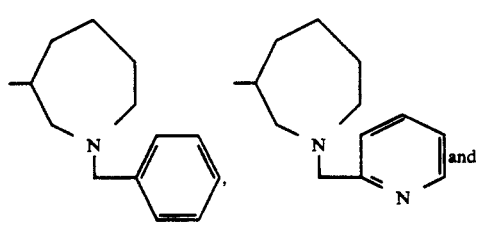

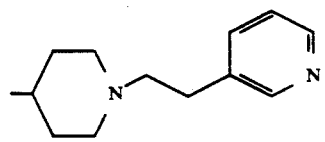

Preferable examples of the 6- or 7-membered ring formed by the groups $R^5$ and $R^6$ which may contain a nitrogen or oxygen atom in addition to the nitrogen atom to which the groups are bonded are as follows:

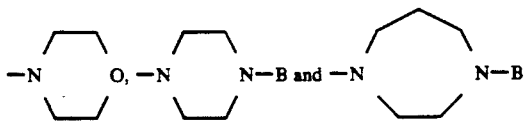

These 6- or 7-membered rings may be each substituted with a B group such as a lower alkyl, arylalkyl, cycloalkylalkyl or heteroarylalkyl group. The arylalkyl, cycloalkylalkyl and heteroarylalkyl groups are each the same as that defined above.

Particular examples thereof are as follows:

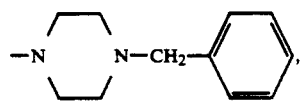

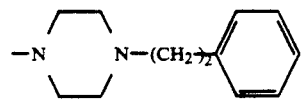

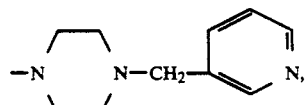

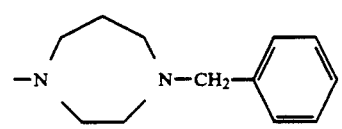

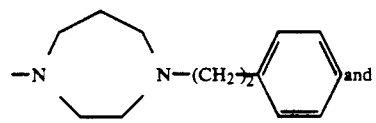

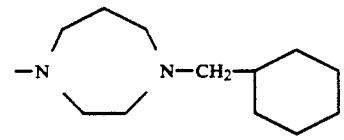

Among the groups defined with respect to $R^7$, a hydrogen atom is most desirable, i.e., the benzene ring is most desirably an unsubstituted one. When r is 2, the two $R^7$ groups may form a ring together with adjacent two carbon atoms constituting the benzene ring. Particular examples of such a ring are as follows:

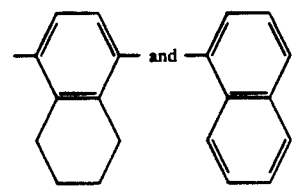

In the general formula (I), the groups represented by the formula: $(R^1)_n$ each independently stand for a hydrogen atom, a cyano, nitro or hydroxyl group, a halogen atom, a lower alkoxy group, an acyloxy group, a group represented by the formula: —SO$_2$—R$^8$ (wherein R$^6$ stands for a lower alkyl group), a heteroaryl group a glycyloxy group or a group represented by the formula

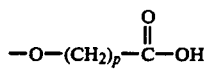

(wherein p is an integer of 1 to 3) and n is an integer of 1 to 4. The term "each independently" used in this description means that when n is an integer of 2 to 4, the substituents on the benzene ring may be either the same or different from each other.

In other words, the general formula (I) can be replaced by the following formula (I'):

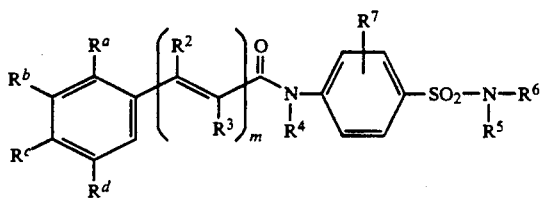

wherein R$^2$, R$^3$, m, R$^4$, R$^7$, R$^5$ and R$^6$ are each as defined above; and R$^a$, R$^b$, R$^c$ and R$^d$ may be the same or different from each other and each stand for a hydrogen atom, a cyano, nitro or hydroxyl group, a halogen atom, a lower alkoxy group, an acyloxy group, a group represented by the formula: —SO$_2$—R$^8$ (wherein R$^8$ stands for a lower alkyl roup), a heteroaryl group, a glycyloxy group or a group represented by the formula:

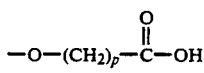

(wherein p is an integer of 1 to 3).

That is, the benzenesulfonamide derivative according to the present invention may be mono-, di-, tri- or tetra substituted with the groups described above, the groups being either the same or different from each other. Among these substituted derivatives, preferred ones are those wherein the benzene ring is monosubstituted with a lower alkylsulfonyl group such as a methylsulfonyl group or an imidazolyl, cyano or nitro group at the p-position (i.e., 4-position) or is di-substituted with two members selected from among halogens and a hydroxyl group, for example, 3-fluoro-4-hydroxy and 3,4-dihydroxy derivatives.

The pharmacologically acceptable salt according to the present invention may be any conventional nontoxic one and examples thereof include inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the derivative according to the present invention may form a metal salt such as sodium, potassium or calcium salt depending upon the substituents.

Although the compound of the present invention may be present as a geometrical isomer, cis or trans, because it has a double bond as shown by its structural formula, it is needless to say that the present invention includes both of the isomers.

In order to represent more precisely that the present invention include both of the cis and trans isomers, the general formula (I) specifying the compound of the present invention can be replaced by the following formula:

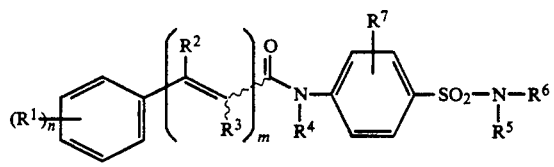

wherein R$^1$, R$^2$, R$^3$, R$^4$, R$^5$, R$^6$, R$^7$, n and m are each as defined above.

Representative processes for the preparation of the compound according to the present invention will now be described.

Preparation process A

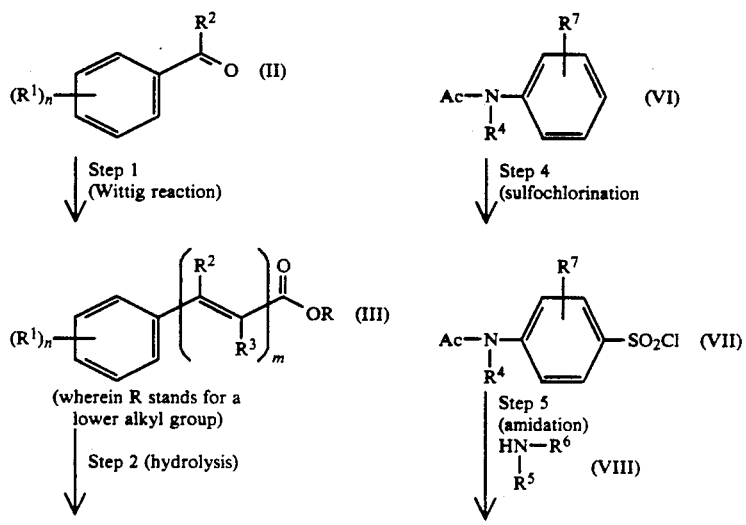

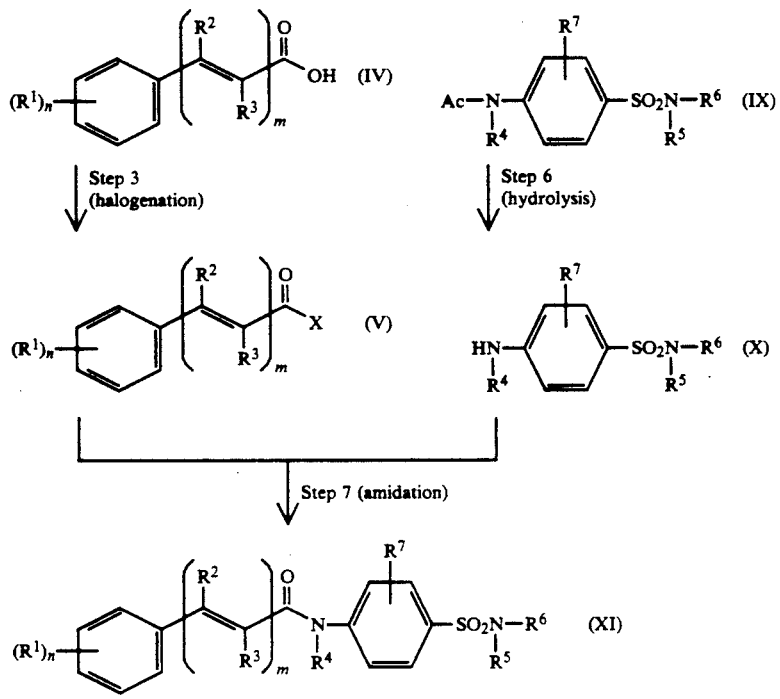

(in the above reaction scheme, $R^1$, $R^2$, $R^3$, $R^4$, $R^5$, $R^6$, m and n are each as defined above; Ac stands for an acetyl group; and X stands for a halogen atom)

Preparation process B

A compound represented by the general formula (I) wherein at least one $R^1$ group is an acetyloxy or methoxy group can be converted into another objective compound (XIV) by the following process:

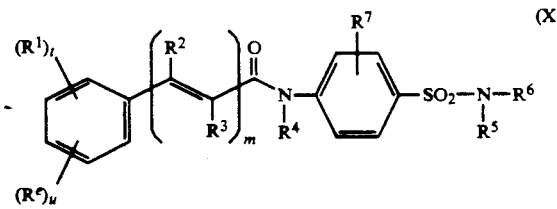

[wherein $R^e$ stands for an acetyloxy (OAc) group or an alkoxy group such as a methoxy group; and t and u are each an integer of 1 to 4 with the proviso that they satisfy the relationship : $t+u \leq 4$.]

Step 8
(when $R^e$ is an OAc group)
hydrolysis

Step 9
(when $R^e$ is an alkoxy group)
dealkylation (wherein R'O stands for an acyloxy or glycyloxy group)

Preparation process C

A compound represented by the general formula (I) wherein $R^6$ is a group represented by the formula:

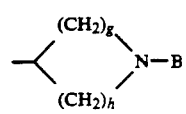

(wherein g and h are each an integer of 1 to 4) can be prepared also by the following processes:

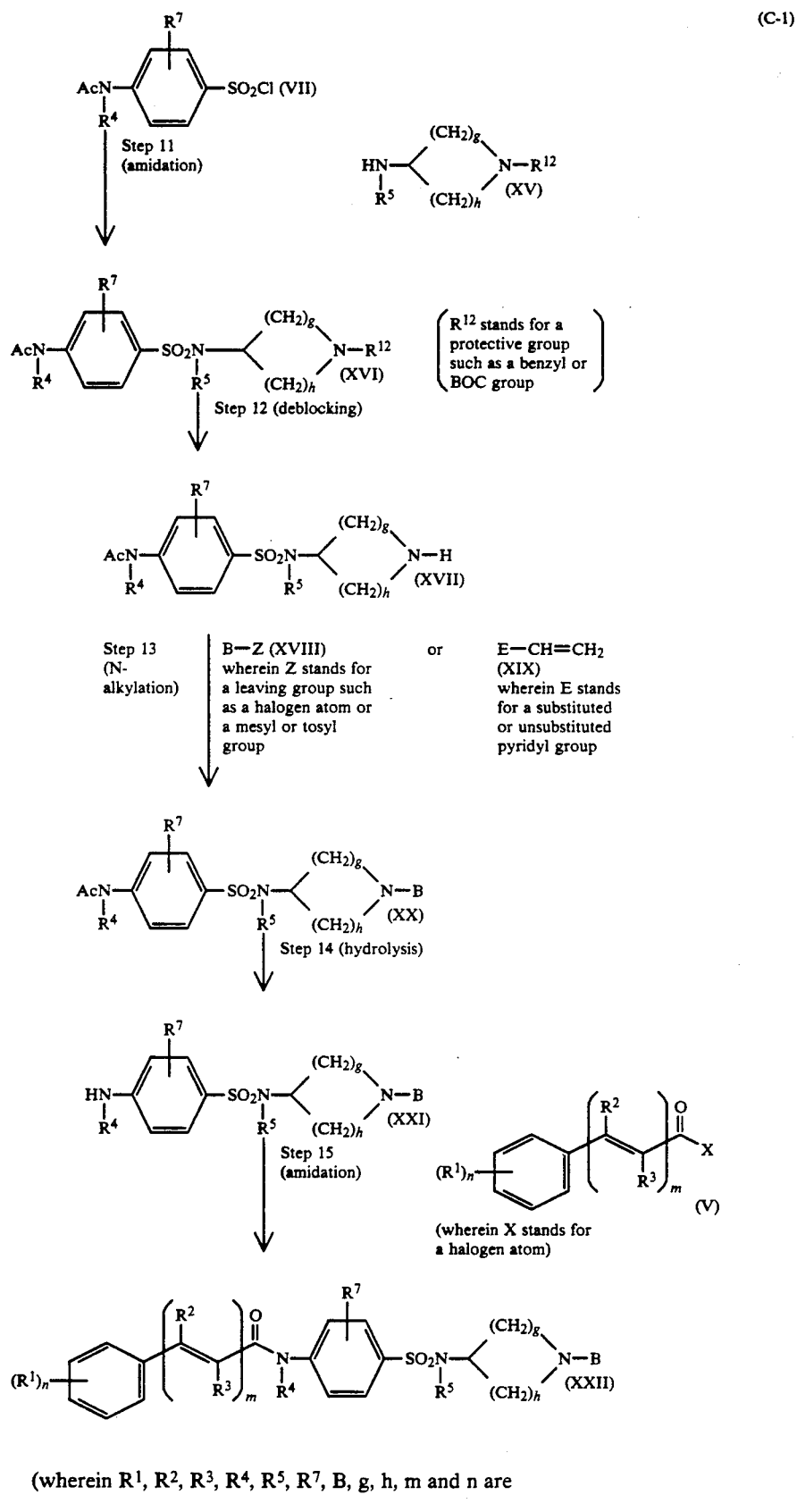
(C-1)
(wherein $R^1$, $R^2$, $R^3$, $R^4$, $R^5$, $R^7$, B, g, h, m and n are each as defined above)

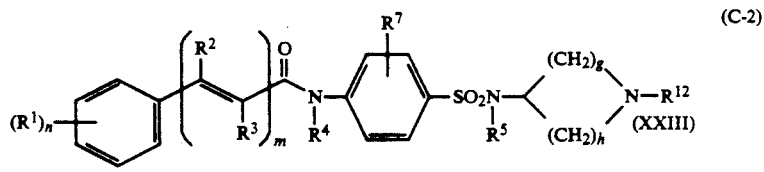 (C-2)

Step 16 (deblocking)

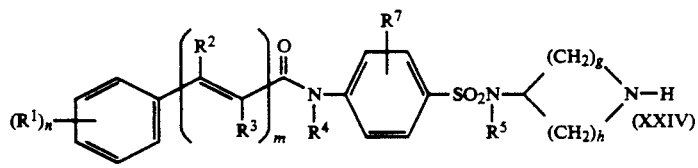 (XXIV)

Step 17 (N-alkylation)

(XXII)

(in the above reaction scheme, $R^1$, $R^2$, $R^3$, $R^4$, $R^5$, $R^6$, $R^7$, $R^{12}$, g, h, m and n are each as defined above)

Preparation process D

A compound represented by the general formula (I) wherein $R^5$ and $R^6$ form a 6- or 7-membered ring which may contain another nitrogen atom in addition to the nitrogen atom to which $R^5$ and $R^6$ are bonded and which may be substituted can be prepared also by, e.g., the processes which will be described below.

A case wherein the

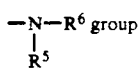 group is one represented by the formula:

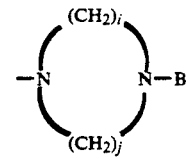

wherein i and j are each an integer of 2 to 3; and B stands for a hydrogen atom or a substituent described above) will now be described.

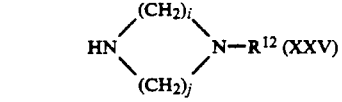 (D-1)

Step 18 (amidation)

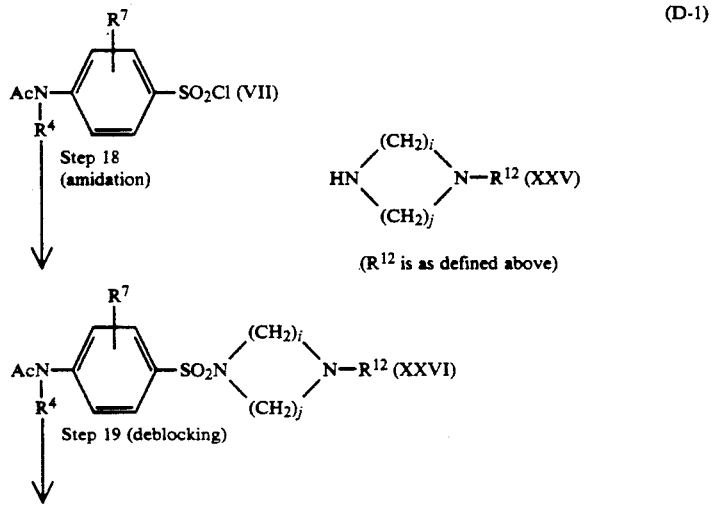

($R^{12}$ is as defined above)

Step 19 (deblocking)

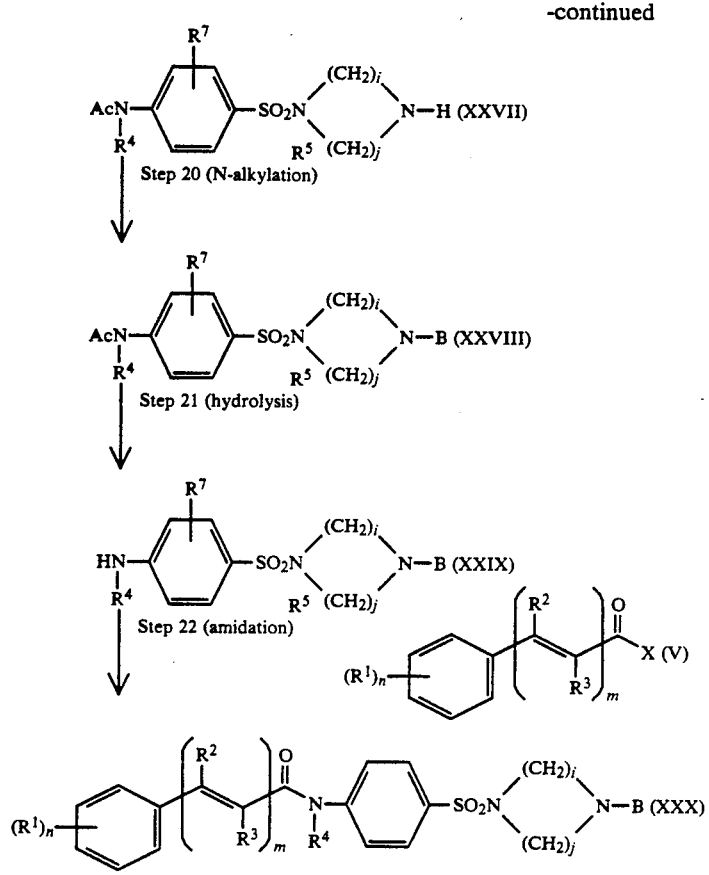

(in the above reaction scheme, $R^1$, $R^2$, $R^3$, $R^4$, B, i, j, m and n are each as defined above)

(D-2)

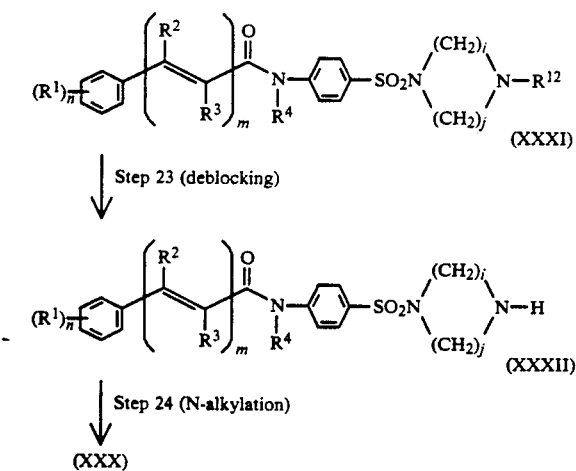

(wherein $R^1$, $R^2$, $R^3$, $R^4$, $R^{12}$, i, j, m and n are each as defined above)

Step 1

In this step, a ketone or aldehyde (II) which is known in itself or can be prepared by a known process is converted into a cinnamic acid derivative (III) through Wittig reaction, aldol condensation or Knoevenagel reaction. When the conversion is conducted through Wittig reaction, a compound (II) is reacted with a Wittig reagent such as triethylphosphonoacetate, triethylphosphonocrotonate or triethylphosphonopropionate generally in an inert solvent such as dimethylformamide, ether, tetrahydrofuran, dioxane, benzene, toluene or dimethyl sulfoxide in the presence of a base such as potassium butoxide, potassium hydroxide, sodium hydroxide, sodium methoxide, sodium ethoxide, sodium hydride or n-butyllithium at a temperature of $-78°$ to $150°$ C. according to a conventional process to give a compound (III).

The compound (III) can be prepared also through aldol condensation or Knoevenagel reaction according to a conventional process.

Step 2

In this step, the compound (III) prepared in Step 1 is converted into a carboxylic acid derivative (IV) through the hydrolysis of an ester linkage. For example, the hydrolysis is conducted in a dilute aqueous solution of an alkali or a mineral acid, preferably a mixture comprising a 0.5 to 3N aqueous solution of sodium hydroxide and ethanol at a ratio of 1:1 or in a 2 to 6N aqueous solution of hydrochloric acid at room temperature to refluxing temperature.

Step 3

In this step, the compound (IV) prepared in Step 2 is halogenated into an acid halide derivative (V). The halogenation is conducted by reacting the compound (IV) with oxalyl chloride, thionyl chloride, phosphorus trichloride or phosphorus tribromide in an inert solvent such as dichloromethane, chloroform, dichloroethane, benzene or toluene at room temperature to refluxing temperature according to a conventional process. When oxalyl chloride is used, it is preferable to use dimethylformamide as a catalyst.

In some cases, the compound (IV) may be converted into other reactive derivative, for example, acid azide, active ester with N-hydroxybenzotriazole or N-hydroxysuccinimide, symmetric acid anhydride or mixed acid anhydride with alkylcarbonic or p-toluenesulfonic acid. These reactive derivatives may be also used in Step 7.

Step 4

In this step, an acetanilide derivative (VI) which is known in itself or can been prepared by a known process is sulfochlorinated into a compound (VII). For example, the compound (VI) is reacted with excess chlorosulfonic acid in an inert solvent such as chloroform, dichloroethane, trichloroethane or nitrobenzene or in the absence of any solvent at room temperature to 100° C. to give a compound (VII).

Step 5

In this step, the sulfonyl chloride derivative (VII) prepared in Step 4 is reacted with an amine (VIII) which is known in itself or can be prepared by a known process to prepare a sulfonamide derivative (IX). For example, the objective compound (IX) can be prepared by reacting the derivative (VII) with an amine (VIII) in a solvent such as water, methanol, ethanol, propanol, acetonitrile, tetrahydrofuran, dioxane, dimethylformamide, dimethyl sulfoxide, dichloromethane, chloroform, benzene or toluene in the presence of a base such as sodium acetate, sodium hydrogencarbonate, sodium carbonate, triethylamine or pyridine at a temperature of 0° C. to room temperature.

Step 6

In this step, the sulfonamide derivative (IX) prepared in Step 5 is converted into an aniline derivative (X) through the hydrolysis of the N-acyl group. The hydrolysis is conducted in a dilute aqueous solution of an alkali or a mineral acid. Preferably, it is conducted in a 2 to 6N aqueous solution of hydrochloric acid or a 0.5 Lo 3N aqueous solution of sodium hydroxide at 50° C. to refluxing temperature.

Step 7

In this step, an amide derivative (XI) is prepared by the reaction of the acid halide or other reactive derivative (V) prepared in Step 3 with the aniline derivative (X) prepared in Step 6.

In the above reaction, the compounds (V) and (X) are used in equimolar amounts or either of them is used in slight excess. The reaction is conducted in an inorganic solvent inert to the reaction, for example pyridine, tetrahydrofuran, dioxane, ether, benzene, toluene, xylene, dichloromethane or chloroform. In some cases, the addition of a base such as diisopropylamine, triethylamine, pyridine, picoline, lutidine, N,N-dimethylaniline, 4-dimethyaminopyridine, potassium carbonate or sodium hydroxide is effective in making the reaction proceed smoothly. Although the reaction temperature varies depending upon the kind of the reactive derivative and therefore is not particularly limited, the reaction is generally conducted at a temperature of 20° C. to refluxing temperature to give an objective compound (XI).

Step 8

Among the compounds (XI) prepared in Step 7, a compound (XII) having an acetoxy group as $R^1$ is converted into a phenol derivative (XIII) in this step through the hydrolysis of the acetyl group.

The hydrolysis is conducted according to a conventional process, for example, either in a solvent such as water, methanol, ethanol, propanol, acetonitrile, tetrahydrofuran or dioxane in the presence of a base such as lithium hydroxide, sodium hydroxide, potassium hydroxide, sodium carbonate, potassium carbonate or sodium hydrogencarbonate, or in a 0.5 to 6N solution of a mineral acid, at a temperature of 0° C. to refluxing temperature.

Step 9

Among the compounds (XI) prepared in Step 7, a compound (XII) having an alkoxy group such as a methoxy group as $R^1$ is converted into a phenol derivative (XIII) through the dealkylation of the alkoxy group in this step.

The dealkylation is conducted according to a conventional process, for example, in an inert solvent such as dichloromethane, chloroform, dichloroethane or nitrobenzene in the presence of a dealkylating agent, for example, boron halide such as boron tribromide, boron trichloride or boron triiodide or aluminum halide such as aluminum trichloride or aluminum tribromide at 0° C. to refluxing temperature.

Step 10

In this step, the phenol derivative (XIII) prepared in Step 8 or 9 is acylated into a compound (XIV). The acylation is preferably conducted by reacting the phenol derivative (XIII) with an amino acid such as glycine, alanine or valine or a carboxylic acid such as nicotinic acid in an inert solvent such as acetonitrile, tetrahydrofuran, dioxane, ether, benzene, toluene, dichloromethane, chloroform, dimethylformamide or dimethyl sulfoxide in the presence of a condensing agent such as dicyclohexylcarbodiimide, 1,1,-carbonyldiimidazole, ethyl chloroformate, diethyl azodicarboxylate or dipyridyl disulfide at a temperature of 0° C. to refluxing temperature.

Step 11

In this step, a sulfonamide derivative (XVI) is prepared by reacting the sulfonyl chloride derivative (VII) prepared in Step 4 with an amine derivative (XV) wherein $R^{12}$ is a nitrogen-protective group such as a benzyl, methoxybenzyl, t-butoxycarbonyl or benzyloxycarbonyl group which is known in itself or can be prepared by a known process. This reaction may be conducted in a similar manner to that described in Step 5.

Step 12

In this step, the compound (XVI) prepared in Step 11 is freed from the N-protective group to give an amine derivative (XVII).

When $R^{12}$ is a benzyl, methoxybenzyl or benzyloxycarbonyl group, it can be removed according to a conventional process. For example, it can be removed by hydrogenating the compound (XVI) in a solvent such as water, methanol, ethanol, propanol, acetonitrile, dioxane, tetrahydrofuran, ether, ethyl acetate or dimethylformamide in the presence of a catalyst such as palladium/carbon, palladium black, platinum oxide or Raney nickel at room temperature to refluxing temperature. In some cases, the coexistence of an acid such as acetic or hydrochloric acid is preferable. When $R^{12}$ is a t butoxycarbonyl group, it can be removed by treating the compound (XVI) in a 1 to 3N solution of hydrochloric acid in a solvent such as water, methanol or ethanol at a temperature of 0° C. to room temperature or by reacting the compound (XVI) with a fluoride reagent such as KF or tetraalkyl ammonium fluoride in a solvent such as methanol, ethanol, acetonitrile, tetrahydrofuran, dioxane or dichloromethane at a temperature of 0° C. to room temperature, though it can be removed also by a conventional process as described above.

Step 13

In this step, the amine derivative (XVII) prepared in Step 12 is converted into a compound (XX) through N-alkylation. The alkylation is conducted by a conventional process. For example, when the alkylating agent is a compound (XVIII), the compound (XX) can be prepared by reacting the compound (XVII) with the compound (XVIII) in a solvent, for example, dimethylformamide, dimethyl sulfoxide, a lower alkyl alcohol such as methanol, ethanol or propanol, acetone, benzene, chloroform or dichloromethane in the presence of a base at room temperature to refluxing temperature. The base includes potassium carbonate, sodium carbonate, sodium hydrogencarbonate, sodium methoxide, sodium ethoxide and sodium hydride. In some cases, the additional use of lithium bromide or potassium iodide gives better results.

When the alkylating agent is a compound (XIX), the objective compound (XX) can be prepared by reacting the compound (XIX) with the amine derivative (XVII) in a polar solvent such as water, methanol, ethanol, dioxane tetrahydrofuran or acetonitrile or a mixture thereof with water in the presence of a small amount of hydrochloric acid, acetic acid or sodium acetate at a temperature of 50° C. to refluxing temperature.

When B is a substituted or unsubstituted pyridyl alkyl group, the compound (XX) can be prepared by the condensation of the compound (XVII) with an alkylating agent represented by the formula (XVIII): B-Z. Particularly, when B is a substituted or unsubstituted pyridylethyl group (i.e., when the alkyl group in the above definition is an ethyl group), the compound (XX) can be prepared also by the addition reaction of the compound (XVII) with a compound represented by the formula (XIX) E—CH=CH$_2$.

When E is a pyridyl group which is unsubstituted or substituted with a lower alkyl group, the formula (XIX) can be replaced by the following formula:

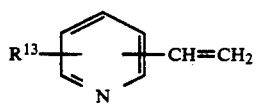
(XIX')

Step 14

In this step, the compound (XX) prepared in Step 13 is converted into an aniline derivative (XXI) through the hydrolysis of the N acyl group. The hydrolysis can be conducted in a similar manner to that of Step 6.

Step 15

In this step, an amide derivative (XXII) is prepared by reacting the aniline derivative (XXI) prepared in Step 14 with the acid halide or other reactive derivative (V) prepared in Step 3. This reaction can be conducted in a similar manner to that of Step 7.

Steps 16 to 24

These steps can be each conducted in a similar manner to that described in one of the above-mentioned steps. The steps corresponding to them respectively are as follows:

(Step 16→Step 12)
(Step 17→Step 13)
(Step 18→Step 5)
(Step 19→Step 12)
(Step 20→Step 13)
(Step 21→Step 6)
(Step 22→Step 7)
(Step 23→Step 12)
(Step 24–Step 13)

Representative compounds of the present invention will now be described in order to facilitate the understanding of the present invention, though it is needless to say that the present invention is not limited by them. They are all represented in free forms.

1. N-[1-(2-phenylethyl)-4-piperidyl]-4-{N-methyl-N-[(E)-3-(4-methylsulfonylphenyl) -2-propenoyl]amino}benzenesulfonamide,
2. N-(1-benzyl-4-piperidyl)-4-(N-methyl [(E)-3-(4-methylsulfonylphenyl)-2-propenoyl]amino}benzenesulfonamide,
3. N-methyl N-[2-(6-methyl-2-pyridyl)ethyl]-4-{N-methyl-N-[(E)-3-(4-methylsulfonylphenyl)-2-propenoyl]amino}benzenesulfonamide,
4. (±)N-[1-(2-pyridylmethyl)-3-hexamethyleneimino]-4 {N methyl-N-[(E)-3-(4-methylsulfonylphenyl)-2-propenoyl]amino}benzenesulfonamide,
5. (E)-N-methyl-N-{4-[4-(2 phenylethyl)-homopiperazinyl]sulfonylphenyl}-3-(4-methylsulfonylphenyl)-2-propenamide,
6. (±)-[1-benzyl-3-hexamethyleneimino]-4-{N-methyl N-[(E)-N-3-(4-methylsulfonylphenyl)-2-propenoyl]amino)benzenesulfonamide,
7. N-[1-(2-methylpiopyl)-4-piperidyl]-4-{N-methyl N-[(E) 3-(4-methylsulfonylphenyl)-2-propenoyl]amino} benzenesulfonamide,
8. N-[1-methyl-4-piperidyl]-4-{N-methyl-N-[(E) 3 (4-methylsulfonylphenyl) -2-propenoyl]amino}-benzenesulfonamide,
9. N-(3-quinuclidyl)-4-{N methyl-N-[(E)-3-(4-methylsulfonylphenyl)-2-propenoyl]amino}benzenesulfonamide,
10. N-[3-(N,N-dimethylamino)propyl]-4-(N-methyl-N-[(E)-3-(4-methylsulfonylphenyl) -2-propenoyl]amino)benzenesulfonamide,
11. N-pycloheptyl-4-(N-methyl-N-[(E)-3-(4-methylsulfonylphenyl)-2-propenoyl]amino}benzenesulfonamide,
12. N-[2-(6-methyl-2-pyridyl)ethyl]-4-{N-methyl-N-[(E)-3-(4-methylsulfonylphenyl)-2-propenoyl]amino} benzenesulfonamide,
13. N-[3-(4-pyridyl)propyl]-4-{N-methyl N-[(E)-3-(4-methylsulfonylphenyl) -2 propenoyl]amino}benzenesulfonamide, 14. N-methyl-N-[2 (2-pyridyl)ethyl]-4-{N-methyl-N-[(E)-3-(4-methylsulfonylphenyl)-2-propenoyl]amino} benzenesulfonamide,
15. N-[2-(2-pyridyl)ethyl]-4-{N-methyl-N-[(E)-3-(4-methylsulfonylphenyl) -2-propenoyl]amino}benzenesulfonamide,
16. N-(2-pyridylmethyl)-4-(N-methyl-N-[(E)-3-(4-methylsulfonylphenyl)-2-propenoyl]amino}benzensulfonamide,
17. (E)-N-methyl-N-[4-(4-cyclohexylmethyl-1-homopiperazinyl)sulfonylphenyl]-3 (4 methylsulfonylphenyl)-2-propenamide,
18. (E)-N-methyl-N-[4-(4-benzyl-1-homopiperazinyl)-sulfonylphenyl]-3-(4-methylsulfonylphenyl)-2-propenamide,
19. (E)-N methyl-N-{4-[4-(2-phenylethyl)-piperazinyl]-sulfonylphenyl}-3-(4-methylsulfonylphenyl)-2-propenamide,
20. (E) N-methyl-N-(4-[4 (3-pyridylmethyl)-piperazinyl]sulfonylphenyl}-3-(4-methylsulfonylphenyl)-2-propenapide,
21. (E) N-methyl-N-[4-(4-benzylpiperazinyl)sulfonylphenyl]-3-(4-methylsulfonylphenyl)-2-propenamide,
22. N-cycloheptyl-4-{N-methyl-N-[(E)-3-(4-cyanophenyl)-2-propenoyl ]amino}benzenesulfonamide,
23. N-(1-benzyl-4-piperidyl)-4-{N-methyl-N-[(E)-3-(4-cyanophenyl)-2-propenoyl]amino}benzenesulfonamide,
24. N-(2-indanyl)-4-(N-methyl-N-[(E)-3-[4-(1-imidazolyl)phenyl]-2-propenoyl]amino}benzenesulfonamide,
25. N-[1-(1,2,3,4-tetrahydro)naphthyl]-4-{N-methyl-N-[(E)-3-(4-(1-imidazoyl)phenyl]-2-propenoyl]amino} benzenesulfonamide,
26. N cycloheptyl-4-{N-methyl-N-[(E)-3-[4-(1-imidazolyl)phenyl-2-propenoyl]amino}benzenesulfonamide,
27. N-cyclooctyl-4-{N-methyl-N-[(E)-3-[4-(1-imidazolyl)phenyl]-2-propenoyl]amino}benzenesulfonamide,
28. (±)-N-(exo-2-norbornyl)-4-{N-methyl-N-[(E)-3-[4-(1-imidazolyl)phenyl ]-2-propenoyl]amino}benzenesulfonamide,
29. (±)-N-(endo-2-norbornyl)-4-{N-methyl-N-[(E)-3-[4-(1-imidazolyl) phenyl]-2-propenoyl]amino}benzenesulfonamide,
30. N (2-indanyl)-4-{N-methyl-N-[(E)-3-[4- nitrophenyl)-2-propenoyl]amino}benzenesulfonamide,
31. N-cyclohexyl-N-methyl-4-{N-[(E)-3-(4-nitrophenyl)-2-propenoyl]amino}benzenesulfonamide,
32. N-cyclohexyl-4-{N-[(E)-3-(4-nitrophenyl)-2-propenoyl]amino}benzenesulfonamide,
33. N-cyclohexyl-4-{N-methyl-N-[(E)-3-(4-nitrophenyl)-2-propenoyl]amino}benzenesulfonamide,
34. N cyclohexyl-N-methyl-4-{N-methyl-N-[(E)-3-(4-nitrophenyl)-2-propenoyl]amino}benzenesulfonamide,
35. N-cycloheptyl-4-{N-methyl-N-[(E)-3-(4-nitrophenyl)-2-propenoyl]amino}benzenesulfonamide,
36. N-cycloheptyl-4-{N-methyl-N-[(2E, 4E)-5-(4-nitrophenyl)-2,4-pentadienoyl]amino}benzenesulfonamide,
37. N-(2-indanyl)-4-{N-methyl-N-[(E)-3-(3,5-dihydroxyphenyl)-2-propenoyl]amino}benzenesulfonamide,
38. N-(2-indanyl)-4-{N-methyl-N-[(E)-3-(4-dihydroxyphenyl)-2-propenoyl]amino}benzenesulfonamide,
39. 4-{(E)-1-[N-methyl-N-[4-(2-indanyl)amino-sulfonylphenyl]amino]-3-propenoyl}phenoxyacetic acid,
40. N-cyclobutyl-4-{N-methyl-N-I(E)-3-(3-fluoro-4-hydroxyphenyl)-2 propenoyl]amino}benzenesulfonamide,
41. N-cycloheptyl-4-{N-methyl-N-[(2E, 4E)-5-(3,5-dibromo-4-hydroxyphenyl) -2,4-pentadienoyl]amino} benzenesulfonamide,
42. N-cycloheptyl-4-{N-methyl-N-[(E)-3-(4-fluorophenyl)-2-propenoyl]amino}benzenesulfonamide,
43. N-(2-indanyl)-4-{N-methyl-N-[(E)-3-(3,4-dihydroxyphenyl)-2-propenoyl]amino}benzenesulfonamide,
44. N-(2-indanyl)-4-{N-methyl-N-[(2E, 4E) 5-(3,4-dihydroxyphenyl)-2,4-pentadienoyl]amino}benzenesulfonamide,
45. N-[2-(1,2,3,4-tetrahydro)naphthyl]-4-{N-methyl-N-[(E)-3-(3,4-dihydroxyphenyl)-2-propenoyl]amino)-benzenesulfonamide,
46. N-[2-(1,2,3,4-tetrahydro)naphthyl]-4-{N-methyl-N-[(2E, 4E)-5-(3,4-hydroxyphenyl)-2,4-pentadienyl]amino}benzenesulfonamide,
47. N-cycloheptyl-4-{N-methyl-N-[(E)-3-(3,4-dihydroxyphenyl)-2-propenoyl]amino}benzenesulfonamide,
48. N-cycloheptyl-4-{N-methyl N-[(2E, 4E)-5-(3,4-dihydroxyphenyl)-2,4-pentadienoyl]amino}benzenesulfonamide,
49. N (2-indanyl)-4-{N methyl-N-[(E)-3-(2-chloro-3,4-dihydroxyphenyl) -2-propenoyl]amino}benzenesulfonamide,
50. N-(2-indanyl)-4-{N-methyl-N-[(E)-3-(3-chloro-3,5-dihydroxyphenyl)-2-propenoyl]amino}benzenesulfonamide,
51. N-(2-indanyl)-4-{N-methyl-N-{(E)-3-(2-chloro-4,5-dihydroxyphenyl)-2-propenoyl]amino}benzenesulfonamide,
52. N-(2-indanyl)-4-{N-methyl-N-[(E)-3-(3-bromo-4,5-dihydroxyphenyl)-2-propenoyl]amino}benzenesulfonamide,
53. N-(2-indanyl)-4-{N-methyl-N-[(E)-3-(2-bromo-4,5-dihydroxyphenyl)-2-propenoyl ]amino}benzenesulfonamide,
54. N-(2-indanyl)-4-{N-methyl-N-[(E)-3-(3,4-dihydroxyphenyl)-2-methyl-2-propenoyl]amino}benzenesulfonamide,
55. N-cyclopentyl-4-{N-methyl-N-[(E)-3-(3,4-dihydroxyphenyl)-2-propenoyl]amino}benzenesulfonamide,
56. N-cyclohexyl-4-{N-methyl-N-[(E)-3-(3,4-dihydroxyphenyl)-2-propenoyl]amino}benzenesulfonamide,
57. N-(1-indanyl)-4-{N-methyl-N-[(E)-3-(3,4-dihydroxyphenyl)-2-propenoyl]amino}benzenesulfonamide,
58. N-[2-(2-pyridyl)ethyl-4-{N methyl-N-[3-(3,4-dihydroxyphenyl)-2-propenoyl]amino}benzenesulfonamide,
59. N-(2-thiazolyl)-4-{N-[(E)-3-(3,4-dihydroxyphenyl)-2-propenoyl]amino }benzenesulfonamide,
60. N-[2-(4,6-dimethyl)pyrimidyl]-4-{N-[(E)-3-(3,4-dihydroxyphenyl)-2-propenoyl]amino}benzenesulfonamide,
61. N-(2-(hydroxyethyl)-4-{N-[(E)-3-(3,4-dihydroxyphenyl)-2-propenoyl]amino}benzenesulfonamide,
62. N-cyclohexyl-4-{N-[(E)-3-(3,4-dihydroxyphenyl)-2-propenoyl]amino}benzenesulfonamide,
63. 4-{N-methyl-N-[(E)-3-(3,4-dihydroxyphenyl)-2-propenoyl]amino}benzenesulfonamide,
64. 4-{N-isopropyl-N-[(E)-3-(3,4 dihydroxyphenyl) 2-propenoyl]amino}benzenesulfonamide, 65. N-[2-(N,N-dimethylamino)ethyl]-4-{N-methyl-N-[(E)-3-(3,4-dihydroxyphenyl) -2-propenoyl]amino}benzenesulfonamide,
66. N-methyl-4-{N-methyl-N-[(E)-3-(3,4-dihydroxyphenyl)-2-propenoyl]amino}benzenesulfonamide,
67. N-isopropyl-4-{N-methyl-N-[(E)-3 (3,4-dihydroxyphenyl)-2-propenoyl]amino}benzenesulfonamide,
68. (E)-N-methyl N-[4-(4-morpholinyl)sulfonylphenyl]-3-(4-methylsulfonylphenyl)-2-propenamide,
69. 4-{N-(E)-3-(3,4-dimethoxyphenyl)-2-propenoyl]amino}benzenesulfonamide,
70. 4-{N-(Z)-3-(3,4-dimethoxyphenyl)-3-(3-pyridyl)-2-propenoyl]amino}benzenesulfonamide,
71. 4-{N-(E)-3-(3,4-dimethoxyphenyl)-3-(3-pyridyl)-2-propenoyl]amino}benzenesulfonamide,
72. 4-{N-(Z)-3-(3,4-dihydroxyphenyl)-3-(3-pyridyl)-2-propenoyl]amino}benzenesulfonamide,
73. 4-{N-(E)-3-(3,4-dihydroxyphenyl)-3-(3-pyridyl)-2-propenoyl]amino}benzenesulfonamide,
74. 4-{N-(Z)-3-(3,4-dihydroxyphenyl)-2-(3 pyridyl)-2-propenoyl]amino}benzenesulfonamide,
75. 4-{N-(E)-3-(3,4-dihydroxyphenyl) 2-propenoyl]amino}benzenesulfonamide,
76. N-[4-(1-piperidylmethyl)benzyl]-4- {N methyl-N-(E)-3-(4-methylsulfonylphenyl)-2-propenoyl]amino} benzenesulfonamide,
77. N-[1-(2-(3,4-dimethoxyphenyl)ethyl]-4-piperidyl]-4-{N-methyl-N-(E)-3-(4-methylsulfonylphenyl)-2-propenoyl]amino}benzenesulfonamide,
78. N-[1-(2-(3-pyridyl)ethyl]-4-piperidyl]-4-{N-methyl-N-[(E)-3-(4-methylsulfonylphenyl) 2-propenoyl]amino}benzenesulfonamide,
79. N-[1-(2-(6-methyl-2-pyridyl)ethyl]-4-piperidyl-4-{N-methyl-N-(E)-3-(4-methylsulfonylphenyl)-2-propenoyl]amino}benzenesulfonamide,
80. N-[4-(1-pyrrolidylmethyl)benzyl]-4-{N-methyl-N-(E)-3-(4-methylsulfonylphenyl)-2-propenoyl]amino} benzenesulfonamide,
81. N-[8-(5,6,7,8-tetrahydro)quinolyl]-4-{N-methyl-N-[(E)-3-(4-methylsulfonylphenyl)-2-propenoyl]amino} benzenesulfonamide,
82. N-cyclohexyl-4-{N-[(E)-3-(3-fluoro -4-hydroxyphenyl)-2-propenoyl]amino}benzenesulfonamide,
83. N-cyclohexyl-4-methyl-4-{N-[(E)-3-(3-fluoro-4-hydroxyphenyl)-2-propenoyl]amino}benzenesulfonamide,
84. N-cycloheptyl-4-{N-methyl-N-[(E)-3-(4-hydroxyphenyl)-2-propenoyl]amino}benzenesulfonamide,
85. N-cyclooctyl-4-{N-methyl-N-[(E)-3-(3-fluoro-4-hydroxyphenyl)-2-propenoyl]amino}benzenesulfonamide,
86. N-cycloheptyl-4-{N-[(E)-3-[4-(1-imidazolyl)-phenyl]-2-propenoyl]amino}benzenesulfonamide,
87. 4-{N-[(E)-3-(3-acetoxy-4-methoxyphenyl]-2-propenoyl]amino}benzenesulfonamide,
88. N-cycloheptyl-4-{N [(E)-3-([3,4-dihydroxyphenyl]-2-methyl-2-propenoyl]amino}benzenesulfonamide,
89. N-cyclohexyl-4-{N-methyl-N-[(E)-3-([3,5-dihydroxyphenyl]-2-propenoyl]amino}benzenesulfonamide,
90. N-(2-indanyl)-4-{N-methyl-N-[(E)-3-[4-hydroxy 3-methoxyphenyl)-2-cyano-2-propenoyl]amino}benzenesulfonamide,
91. 4-{N-[(E)-3-(3,4-dihydroxyphenyl)-2-propenoyl]amino}-5,6,7,8-tetrahydro-1-naphthalenesulfonamide,
92. N-(2-indanyl)-4-{N-methyl-N-[(E)-3-[3,4-diglycyloxyphenyl)-2-propenoyl]amino}benzenesulfonamide,
93. N-isopropyl-4-{N-methyl-N-[(E)-3-(2-chloro-3,4-dihydroxyphenyl)-2-propenoyl]amino}benzenesulfonamide,
94. 4-{N-[(E)-3-(2-bromo-4,5-dihdyroxyphenyl)-2-propenoyl]amino}benzenesulfonamide,
95. N-(2-thiazolyl)-4-{N-[(Z)-3-(3,4-dimethoxyphenyl)-2-(3-pyridyl-2-propenoyl]amino}benzenesulfonamide,
96. 4-{N-[(Z)-3-(3,4-dimethoxyphenyl)-2-(3-pyridyl)-2-propenoyl]amino}benzenesulfonamide,
97. N-(thiazolyl)-4-{N-[(E)-3-(3,4-dimethoxyphenyl-2-propenoyl]amino}benzenesulfonamide,
98. 4-{N-[(E)-3-(4-hydroxy-3-methoxyphenyl)-2-propenoyl]amino}benzenesulfonamide, and
99. N-(2-indanyl)-4-{N-methyl-N-[(E)-3-(3,4-diacetoxyphenyl)-2-propenoyl]amino}benzenesulfonamide.

Pharmacological Experiment Examples with respect to representative compounds according to the present invention will now be described in order to illustrate the effects of the present invention in more detail.

PHARMACOLOGICAL EXPERIMENT EXAMPLES

A. Inhibitory activity against phospholipase $A_2$ ($PLA_2$) contained in the membrane fraction of rabbit heart or the supernatant fraction thereof (method)

1. Preparation of membrane fraction of rabbit heart and supernatant fraction thereof An NZW male rabbit was anesthetized by the intravenous administration of pentobarbital sodium to take out its heart. This heart was washed with ice cooled physiological saline to recover a ventricle, followed by the addition of ice-cooled 0.25M sucrose/20 mM tris hydrochloride buffer (pH: 8.0) in an amount of 5 ml per g of the ventricle. The obtained mixture was mashed with a homogenizer in ice water for 30 minutes and centrifuged at 1,000 g for 10 min. The supernatant was further centrifuged at 105,000 g for 60 min. The centrifugation was conducted at 0° to 4° C. The obtained supernatant was used as such as the supernatant fraction for examination. The precipitate was suspended in the same buffer as that described above and used as the membrane fraction for examination. The protein concentrations of these fractions were each adjusted to 5 mg/ml as determined by Lowry method.

2. Determination of $PLA_2$-inhibitory activity

A 100 mM $CaCl_2$ solution was added to the above membrane fraction in an amount of 100 μl per 10 ml of the fraction, while a 100 mM solution of ethylene glycol bis(β-aminoethyl ether)-N,N,N',N'-tetraacetic acid (EGTA) was added to the above supernatant fraction in an amount of 500 μl per 10 ml of the fraction. The obtained mixtures were each poured into test tubes in an amount of 0.2 ml per tube, followed by the addition of 2 μl of a solution of a test compound in dimethyl sulfoxide (DMSO) into each of the tubes, while 2 μl of DMSO was poured into a test tube for control. 5 μl of an 8 mM ethanol solution of phosphatidylcholine (1-palmitoyl-2-[1-$^{14}$C]arachidonyl, 1.184 MBq/ml) was added to each of the test tubes. The test tubes of the membrane fraction were kept at 37° C. for 30 minutes for incubation, while those of the supernatant fraction were kept at 37° C. for 5 minutes for incubation. Each incubation was stopped by the addition of 1 ml of Dole reagent. The $^{14}$C-arachidonic acid was extracted with heptane and the heptane layer was passed through silica gel to remove the phosphatidylcholine contained therein by adsorption. The amount of $^{14}$C was determined with a liquid scintillation counter.

Mepacrine was selected as a comparative compound.
(Results)

The results are given in Table 1.

TABLE 1

| Compound (Example No.) | PLA$_2$-inhibitory activity IC$_{30}$ ($\mu$M) | |
|---|---|---|
| | membrane fraction | supernatant fraction |
| 2 | 4.48 | 40 |
| 3 | 2.4 | nt |
| 4 | 0.032 | >100 |
| 5 | 0.007 | 49 |
| 6 | 0.056 | >100 |
| 7 | 0.018 | >100 |
| 8 | 0.029 | >100 |
| 9 | 0.015 | 61 |
| 14 | 0.016 | >30 |
| 15 | 0.081 | 61 |
| 18 | 0.18 | >100 |
| 20 | 0.045 | 92 |
| 21 | 0.055 | >100 |
| 22 | 0.050 | >100 |
| 25 | 0.16 | 68 |
| 26 | 0.24 | 59 |
| 29 | 0.45 | 90 |
| 30 | 0.66 | >100 |
| 31 | 0.42 | 29 |
| 38 | 0.12 | 29 |
| 41 | 0.98 | 46 |
| 43 | 3.49 | 62 |
| 44 | 5.1 | 39 |
| 48 | 1.7 | 32 |
| 49 | 1.8 | 56 |
| 50 | 1.05 | 38 |
| 58 | 1.5 | 64 |
| 65 | 16 | nt |
| 72 | 41 | nt |
| 77 | 20 | >100 |
| 79 | 0.03 | >100 |
| 81 | 0.044 | >100 |
| 86 | 0.62 | 46 |
| 87 | 2.1 | nt |
| mepacrine | >100 | >100 |

B. Influence on the cardiac infarct size of rat

Sixty-one male rats (weight : 220 to 300 g) were made to get myocardial ischemia by the ligation of the coronary artery. After 3 hours from the ligation, hearts were taken out of the rats and cut into round slices to obtain preparations. These preparations were stained with myoglobin. The area unstained therewith was regarded as a cardiac infarction nidus and the area ratio of the nidus to the left ventricle was determined by the image analysis and regarded as the cardiac infarct size.

The cardiac infarct size was reduced as compared with that of the control rat by 21% or 20% by the administration of the compound of Example 4 or 6 through the tail vein in a dose of 1 mg/kg before 15 minutes prior to the ligation of the coronary artery.

C. Toxicity test

A small amount of 1N HCl was added to each of the compounds of Examples 4, 6, 7, 8 and 15 to form aqueous solutions. These solutions were each intravenously administered to the groups of three male SD rats of 7 weeks of age in a dose of 50 mg/kg. All of the groups of rats were observed for 3 hours after the administration. No rat died.

It can be understood from the results of the above Pharmacological Experiment Examples that each of the compounds of the present invention has a remarkably high inhibitory activity against phospholipase A$_2$ to arrest the course of a series of ischemic cell diseases which are thought to be caused by the activation of phospholipase A$_2$, for example, cardiac infarction.

Particularly, the phospholipase A$_2$-inhibitory activity of each of the compounds according to the present invention is remarkably higher than that of mepacrine used as a comparative compound.

Accordingly, the compounds of the present invention are useful as a remedy or preventive for various diseases for which the phospholipase A$_2$-inhibitory action is efficacious.

Particularly, the compounds of the present invention are usable as a remedy for various heart diseases, an antithrombotic drug or the like.

More particularly, the compounds of the present invention are effective in the treatment and prevention of cardiac infarction; angina pectoris; coogestive cardiac insufficiency accompanied with edema, pulmonary congestion, hepatomegaly or the like; cerebrovascular diseases such as TIA (transient ischemic attack), cerebral infarction (thrombosis and embolism) or (brain edema, cerebrovascular spasm) cerebral arteriosclerosis; postoperative thrombosis and embolism and bloodstream disturbance attendant on the operation of the vessel or the extracorporeal circulation of blood; Buerger disease; and peripheral bloodstream disturbance due to the obliteration and stenosis of appendicular arteries, for example, arteriosclerosis obliterans, SLE or while finger disease, the prevention of relapse of these diseases and the improvement of prognosis thereof.

Further, the compounds of the present invention are efficacious for diseases caused by metabolism intermediates of the arachidonic acid liberated by the action of phospholipase A$_2$, for example, thromboxanes such as thromboxane A$_2$, prostaglandins or leukotrienes, while the diseases include inflammatory disease, rheumatoid arthritis and allergoses such as asthma and atopic dermatitis.

Particularly among these diseases, the compounds of the present invention are thought to be able to arrest the course of a series of ischemic cell diseases caused by the activation of phospholipase A$_2$. The compounds of the present invention are highly valuable in this sense.

When the compounds of the present invention are used as drugs, they may be each administered orally or parenterally (as injection, suppository or external preparation). Although the dose thereof varies depending upon the symptom, age, sex, weight and sensitivity of a patient; the method, timing and interval of administration; the properties, dispensing and kind of preparation; and the kind of an active ingredient and is not particularly limited, the does thereof per adult a day is about 0.1 to 2,000 mg, desirably about 1 to 1,000 mg, more desirably about 5 to 500 mg, most desirably about 20 to 100 mg, which may be generally administered in 1 to 4 portions a day.

A solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellblose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, mentha, herb, aromatic powder, mentha oil, borneol and powdered cinnamon bark. Of course, the tablet and granule may be suitably coated with sugar, gelatin or the like, if necessary.

An injection according to the present invention is prepared by adding a pH modifier, buffer, suspending agent, solubilizing agent, stabilizer, tonicity agent and/or preservative to an active ingredient at need and converting the mixture into an injection for intravenous, subcutaneous or intramuscular administration, or administration into coronary arteries by a conventional process. If necessary, the injection may be freeze-dried according to a conventional method.

Examples of the suspending agent include methylcellulose, Polysorbate 80, hydroxyethylcellulose, acacia, tragacanth powder, carboxymethylcellulose sodium and polyoxyethylene sorbitan monolaurate.

Examples of the solubilizing agent include polyoxyethylene hardened castor oil, Polysorbate 80, nicotinamide, polyoxyethylene sorbitan monolaurate, Macrogol and ethyl ester of castor oil fatty acid.

Further, examples of the stabilizer include sodium sulfite, sodium metasulfite and ether and those of the preservative include methyl p-hydroxybenzoate, ethyl p hydroxybenzoate, sorbic acid, phenol, cresol and chlorocresol.

Example

Examples of the present invention will now be described below, though it is needless to say that the present invention is not limited to them. The preparation of the starting compounds for preparing the compounds of the present invention will be described in the following Preparative Examples preceding Examples.

PREPARATIVE EXAMPLE 1

4-(Methylthio)benzaldehyde dimethyl acetal

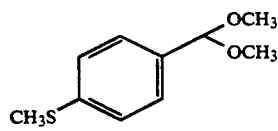

A suspension of K-10 (32 g) in trimethyl orthoformate (115 ml, 1.05 mol) was added to a solution of 4-(methylthio)benzaldehyde (31.0 g, 0.203 mol) in dichloromethane (300 ml) at 0° C. The obtained mixture was stirred at room temperature for 20 minutes and filtered to remove the K-10. The filter cake was washed with dichloromethane. The filtrate and washings were together washed with a saturated aqueous solution of sodium hydrogencarbonate and a saturated aqueous solution of common salt, dried over magnesium sulfate and concentrated in a vacuum to give the title compound as a pale-yellow oil (39.0 g, 96%).

$^1$H-NMR (90 MHz, DMSO-d$_6$) δ: 7.29 (4H, brs), 5.36 (1H, s), 3.26 (6H, s), 2.50 (3H, s).

PREPARATIVE EXAMPLE 2

4-(Methylsulfonyl)benzaldehyde dimethyl acetal

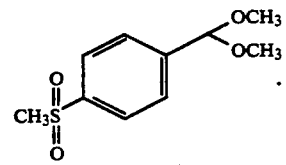

m Chloroperbenzoic acid (115.0 g, 0.567 mol) was added to a suspension of the 4-(methylthio)benzaldehyde dimethyl acetal (50.0 g, 0.252 mol) prepared in Preparative Example 1 and sodium hydrogencarbonate (73.1 g) in dichloromethane (1.00 l) at 0° to 10° C. in portions (over a period of about one hour and 20 minutes). The obtained suspension was stirred at room temperature for 18 hours and poured into an aqueous solution (1 l) of sodium sulfite (100.0 g) under cooling to decompose excess peracid. The resulting solution was extracted with dichloromethane and the organic layer was washed with a saturated aqueous solution of common salt, dried over magnesium sulfate and concentrated in a vacuum. The obtained solid residue was recrystallized from hexane/isopropyl ether/ethyl acetate to give the title compound as a colorless crystal (53.9 g, yield: 93%).

m.p. (°C.): 100 to 110

$^1$H-NMR (90 MHz, DMSO-d$_6$) δ: 7.92 (2H, d, J=7.9), 7.61 (2H, d, J=7.9), 5.50 (1H, s), 3.28 (6H, s), 3.24 (3H, s).

PREPARATIVE EXAMPLE 3

4-Methylsulfonyl)benzaldehyde

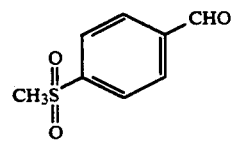

1N Hydrochloric acid (200 ml) was added to a solution of the 4-(methylsulfonyl)benzaldehyde dimethyl acetal (39.4 g, 0.171 mol) prepared in Preparative Example 2 in dioxane (200 ml). The obtained mixture was stirred under heating at 100° C. for 20 minutes to conduct a reaction. The reaction mixture was cooled by allowing to stand and concentrated in a vacuum to give a crystal. This crystal was recovered by filtration, washed with water and dried to give the title compound as a colorless crystal (30.9 g, 98%).

m.p. (°C.): 153 to 157

$^1$H-NMR (90 MHz, CDCl$_3$) δ: 10.10 (1H, s), 8.06 (4H, s), 3.10 (3H, s).

PREPARATIVE EXAMPLE 4

Ethyl (E)-3-(4-methylsulfonyl)phenyl-2-propenoate

-continued

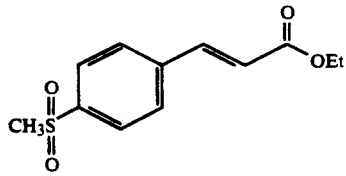
5

A solution of ethyl diethylphosphonoacetate (46.2 ml, 0.233 mol) in tetrahydrofuran (180 ml) was dropped into a solution of sodium hydride (60% in mineral oil, 9.20 g, 0.230 mol) in tetrahydrofuran (250 ml) at 0° C. The obtained solution was stirred at that temperature for 10 minutes. A solution of the 4 (methylsulfonyl)benzaldehyde (40.4 g, 0.219 mol) prepared in Preparative Example 3 in dimethylformamide (300 ml)/tetrahydrofuran (50 ml) was dropped into the resulting solution at 0° C. The obtained mixture was stirred at room temperature for 2 hours and cooled with ice again, followed by the addition of an aqueous solution (1.0 l) of ammonium chloride (25 g). The obtained mixture was extracted with ethyl acetate. The organic layer was washed with a saturated aqueous solution of common salt, dried over magnesium sulfate and concentrated in a vacuum. The solid residue was recrystallized from hexane/isopropyl ether to give the title compound as a colorless crystal (48.8 g, yield: 87%).

m.p.(°C.): 91 to 92.

$^1$H-NMR (90 MHz, CDCl$_3$) δ: 7.96 (2H, d, J=8.6), 7.70 (1H, d, J=15.8), 7.68 (2H, d, J=8.6), 6.54 (1H, d, J=15.8), 4.29 (2H, q, J=7.0), 3.07 (3H, s), 1.35 (3H, t, J=7.0)

PREPARATIVE EXAMPLE 5

(E)-3-(4-Methylsulfonyl)phenyl-2-propenoic acid

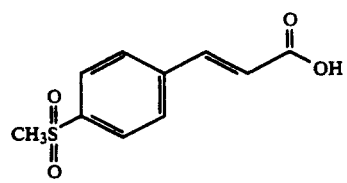

The ethyl (E)-3-(4-methylsulfonyl)phenyl-2-propenoate (48.1 g, 0.189 mol) prepared in Preparative Example 4 was suspended in a mixture comprising ethanol (300 ml) and 1N aqueous sodium hydroxide (300 ml). The obtained suspension was stirred at 50° C. for one hour.

The obtained solution was cooled with ice and 1N hydrochloric acid (330 ml) was dropped thereinto to precipitate a crystal. This crystal was recovered by filtration, washed with water and isopropyl ether and dried to give the title compound as a colorless crystal (42.4 g, 99%).

m.p. (°C.): 230 to 240

$^1$H-NMR (90 MHz, DMSO d$_6$) δ: 7.95 (4H, s), 7.67 (1H, d, J=15.8), 6.70 (1H, d, J=15.8), 3.24 (3H, s).

The same procedure as that of Preparative Example 4 or 5 was repeated except that 3-fluoro-4-methoxybenzaldehyde, 3,5-dibromo-4-hydroxybenzaldehyde, 3-(3,4-dimethoxybenzoyl)pyridine or 3,4-dimethoxybenzaldehyde was used instead of 4-(methylsulfonyl)benzaldehyde or that triethyl-4-phosphonocrotonate or triethyl-2-phosphonopropionate was used instead of triethylphosphonoacetate to prepare the compounds listed in Table 2.

TABLE 2

| Prep. Ex. | Structural formula | m.p. (°C.) | $^1$H-NMR δ |
|---|---|---|---|
| 6 | ![F, AcO-phenyl-CH=CH-COOH] | 185–195 | (90 MHz, DMSO-d$_6$); 7.78(1H, dd, J=11.9, 1.8), 7.58(1H, d, J=11.2), 7.56(1H, brdd, J=9.5, 2.4), 7.32(1H, J=8.0), 6.57(1H, d, J=16.2), 2.33(3H, s) |
| 7 | ![Br, CH$_3$O, Br-phenyl-CH=CH-CH=CH-COOH] | 201–205 | (400 MHz, DMSO-d$_6$); 7.87(2H, s), 7.23(2H, m), 6.94(1H, d, J=15.2), 6.01(1H, d, J=14.4), 3.81(3H, s) |
| 8 | ![CH$_3$O, CH$_3$O-phenyl-C(COOH)=CH-pyridyl] | 103–131 | (90 MHz, CDCl$_3$); 8.55(1H, dd, J=4.9, 1.8), 7.63(1H, dt, J=7.9, 2.2), 7.37(1H, dd, J=7.9, 3.9), 6.97(1H, d, J=8.4), 6.77(1H, d, J=1.7), 6.67(1H, dd, J=8.4, 1.7), 6.34(1H, s), 3.78 & 3.68(each 3H, s) |

TABLE 2-continued

| Prep. Ex. | Structural formula | m.p. (°C.) | $^1$H-NMR δ |
|---|---|---|---|
| 9 | 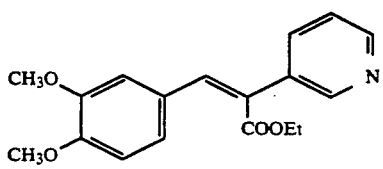 | 216~218 | (90 MHz, CDCl$_3$); 8.55(1H, dd, J=4.7, 1.8), 8.34(1H, dd, J=8.1, 4.7, 0.9), 7.54(1H, dt, J=8.1, 1.8), 7.41(1H, ddd, J=8.1, 4.7, 0.9), 7.04(1H, d, J=2.2), 6.92(1H, d, J=8.5), 6.57(1H, dd, J=8.5, 2.2), 6.47(1H, s), 3.76 & 3.75(each 3H, s) NOE ; 6.47→7.04(10.5%) |

PREPARATIVE EXAMPLE 10

Ethyl (Z)-3-(3,4-dimethoxyphenyl)-2-(3-pyridyl)-2-propenoate

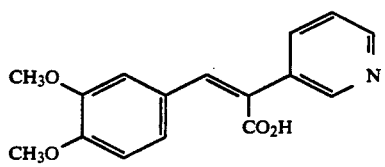

n-Butyllithium (1.6M hexane solution, 99.2 ml) was dropped into a solution of diisopropylamine (23.4 ml, 166.6 mmol) in tetrahydrofuran (320 ml). The obtained mixture was stirred at 0° C. for 30 minutes. A solution of ethyl 3-pyridylacetate (24.0 ml, 158.9 mmol) in tetrahydrofuran (20 ml) was dropped into the resulting mixture at −70° C. and the obtained mixture was stirred at 0° C for 15 minutes. A solution of 3,4-dimethoxybenzaldehyde (27.6 g, 166.0 mmol) in tetrahydrofuran (100 ml) was dropped into the mixture at 0° C. The obtained mixture was stirred at room temperature overnight, followed by the addition of water. The obtained mixture was extracted with ether. The organic layer was washed with water and a saturated aqueous solution of common salt, dried over magnesium sulfate and concentrated. The oily residue was purified by flash column chromatography (ethyl acetate/hexane=3:2) to give the title compound as a pale yellow oil (18.19 g, yield: 37%).

$^1$H-NMR (400 MHz, CDCl$_3$) δ: 8.58 (1H, brd, J=4.1), 8.50 (1H, brs), 7.88 (1H, s), 7.60 (1H, dt, J=7.7, 1.8), 7.33 (1H, dd, J=7.7, 4.9), 6.79 (1H, dd, J=8.5, 2.2), 6.72 (1H, d, J=8.5), 6.41 (1H, d, J=2.2), 4.25 (2H, q, J=7.0), 3.81 and 3.45 (each 3H, s), 1.30 (3H, q, J=7.0).

NOE: 7.88↗→6.79 (7.4%), 6.41 (4.2%) 6.41↗→7.88 (4.6%), 3.45 (10.47%).

PREPARATIVE EXAMPLE 11

(Z)-3-(3,4-Dimethoxyphenyl)-2-(3-pyridyl)-2-propenoic acid

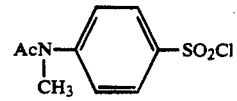

The ethyl (Z)-3-(3,4-dimethoxyphenyl)-2-(3-pyridyl-2-propionate (2.00 g, 6.39 mmol) prepared in Preparative Example 10 was dissolved in a mixture comprising 1N aqueous sodium hydroxide (5 ml) and ethanol (5 ml).

The obtained solution was stirred at room temperature for 5 hours and washed with ethanol (20 ml). The pH of the obtained aqueous layer was adjusted to about 7 by the addition of 1N aqueous hydrochloric acid (about 5.0 ml) to thereby precipitate a crystal. This crystal was recovered by filtration and washed with water and ether to give the title compound as a white crystal (0.71 g, yield: 39%).

m.p. (°C.): 190 to 191

$^1$H-NMR (90 MHz, DMSO$_4$-d$_6$) δ: 8.54 (1H, dd, J=4.8, 1.8), 8.34 (1H, dd, J=1.8, 0.9), 7.81 (1H, s), 7.66 (1H, dt, J=8.0, 1.8), 7.43 (1H, ddd, J=8.1, 4.8, 0.9), 6.86 (1H, d, J=8.8), 6.72 (1H, dd, J=8.8, 1.5), 6.49 (1H, d, J=1.5).

PREPARATIVE EXAMPLE 12

4-(N-Acetyl-N-methylamino)benzenesulfonyl chloride

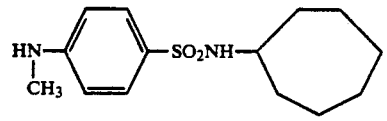

N-Methylacetanilide (25.0 g, 188.0 mmol) was added to chlorosulfonic acid (62.8 ml) under cooling with ice in portions at such a rate as not to raise the temperature of the resulting mixture to 50° C. or above, which took about 10 minutes. The obtained mixture was stirred at 80° C. for 2.5 hours and poured into a mixture comprising ice (200 ml), hexane (30 ml) and isopropyl ether (30 ml) under cooling with ice at 20° C. or below in portions to decompose excess chlorosulfonic acid. The precipitated crystal was recovered by filtration, washed with water and dissolved in ethyl acetate The obtained solution was washed with water and a saturated aqueous solution of common salt. The organic layer was dried over magnesium sulfate and concentrated to give the title compound as a white crystal (19.4 g, yield: 42%).

m.p. (°C.): 139 to 140.

$^1$H-NMR (90 MHz, CDCl$_3$) δ: 8.04 (2H, d, J=9.0), 7.43 (2H, d, J=9.0), 3.36 (3H, s), 2.08 (3H, s).

PREPARATIVE EXAMPLE 13

N-Cycloheptyl-4-(N-methylamino)benzenesulfonamide

Cycloheptylamine (2.26 ml, 17.8 mmol) was added to a suspension of the 4-(N-acetyl-N-methylamino)benzenesulfonyl chloride (4.00 g, 16.2 mmol) prepared in Preparative Example 12 and sodium acetate (3.98 g) in ethanol (40 ml). The obtained mixture was stirred at room temperature for 4 hours, followed by the addition of water. The obtained mixture was extracted with ethyl acetate and the organic layer was washed with water and a saturated aqueous solution of common salt, and dried over magnesium sulfate Ethanol (20 ml) and 1N aqueous sodium hydroxide (20 ml) were added to the obtained white crystal [N-cycloheptyl-4-(N-acetyl-N-methylamino)benzenesulfonamide] (4.72 g, 90%). The obtained mixture was heated under reflux overnight, acidified by the addition of 1N aqueous hydrochloric acid and adjusted to pH 8 with sodium hydrogencarbonate. The resulting mixture was extracted with ethyl acetate and the organic layer was dried over magnesium sulfate and concentrated to precipitate a crystal. This crystal was recovered by filtration and washed with ether to give the title compound as a white crystal (1.92 g, 44%).

m.p. (°C.): 111 to 113.

$^1$H-NMR (400 MHz, DMSO-d$_6$) δ: 7.47 (2H, d, J=8.8), 7.09 (1H, d, J=7.2), 6.57 (2H, d, J=8.8), 6.44 (1H, brq, J=4.8), 2.72 (3H, d, J=4.8)

EXAMPLE 14

N-(2-Indanyl)-4-(N-methylamino)benzenesulfonamide

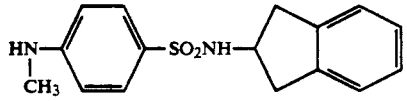

2-Indanylamine hydrochloride (9.68 g, 57.1 mmol) was added to a suspension of the 4-(N-acetyl-N-methylamino)benzenesulfonyl chloride (12.84 g, 51.9 mmol) prepared in Preparative Example 12 and sodium acetate (18.73 g) in ethanol (100 ml). The obtained mixture was stirred at room temperature for 3 hours, followed by the addition of water. The obtained mixture was extracted with ethyl acetate. The organic layer was washed with water and a saturated aqueous solution of common salt, dried over magnesium sulfate, and concentrated to give N-(2 indanyl)-4-(N-acetyl-N-methylamino)benzenesulfonamide as a white crystal (16.92 g, 95%). Ethanol (80 ml) and 1N aqueous sodium hydroxide (80 ml) were added to the white crystal. The obtained mixture was heated under reflux overnight, acidified with 1N aqueous hydrochloric acid, adjusted to pH 8 with sodium hydrogencarbonate and extracted with ethyl acetate. The organic layer was dried over magnesium sulfate and concentrated to precipitate a crystal. This crystal was recovered by filtration and washed with ether to give the title compound as a white crystal (6.79 g, 46%).

m.p. (°C.): 136 to 137.

$^1$H NMR (90 MHz, DMSO-d$_6$) δ: 7.85 (2H, d, J=8.8), 7.53 (2H, d, J=8.8), 7.08 (4H, s), 3.90 (1H, m), 3.24 (3H, s), 3.12~2.54 (4H, m).

PREPARATIVE EXAMPLE 15

N-[2-(6-Methyl-2-pyridyl)ethyl]-4-(N-methylamino)benzenesulfonamide

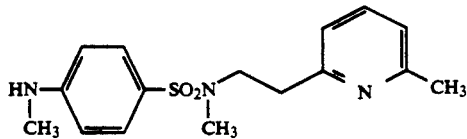

N-Methyl-N-[2-(6-methyl-2-pyridyl)ethyl]amine (14.66 g, 97.7 mmol) was added to a suspension of the 4-(N-acetyl-N-methylamino)benzenesulfonyl chloride (24.2 g, 97.3 mmol) prepared in Preparative Example 12 and sodium acetate (24.0 g) in ethanol (140 ml). The obtained mixture was stirred at room temperature overnight, followed by the addition of water. The obtained mixture was extracted with ethyl acetate. The organic layer was washed with water and a saturated aqueous solution of common salt, dried over magnesium sulfate, and concentrated to give N-[2-(6-methyl-2-pyridyl)ethyl]-4-(N-acetyl-N-methylamino)benzenesulfonamide as a colorless oil. This oil was dissolved in 4N aqueous hydrochloric acid. The solution was heated under reflux for 2 hours. The pH of the mixture was adjusted to about 8 by the addition of an aqueous solution of sodium hydrogencarbonate. The resulting mixture was extracted with ethyl acetate. The organic layer was washed with water and a saturated aqueous solution of common salt, dried over magnesium sulfate, and concentrated to give an oily residue. This residue was purified by flash column chromatography (chloroform/methanol/aqueous ammonia=97:3:0.3) to give the title compound as a light brown oil (25.8 g, overall yield of two steps: 83%).

$^1$H NMR (400 MHz, CDCl$_3$) δ: 7.56 (2H, d, J=8.8), 7.49 (1H, t, J=8.0), 7.03 (1H, d, J=8.0), 6.98 (1H, d, J=8.0), 6.57 (2H, d, J=8.8), 4.28 (1H, brq, J=5.2), 3.36 (2H, t, J=7.2), 2.99 (2H, t, J=7.2), 2.87 (3H, d, J=5.2), 2.69 (3H, s), 2.50 (3H, s)

PREPARATIVE EXAMPLE 16

N-(1-Benzyl-4-piperidyl)-4-(N-methylamino)-benzenesulfonamide dihydrochloride

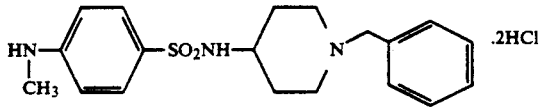

4-Amino-1-benzylpiperidine (3.63 ml, 17.8 mmol) was added to a suspension of the 4-(N-acetyl-N-methylamino)benzenesulfonyl chloride (4.00 g, 16.2 mmol) prepared in Preparative Example 12 and sodium acetate (2.65 g) in ethanol (40 ml). The obtained mixture was stirred at room temperature for 4 hours, followed by the addition of water. The obtained mixture was extracted with ethyl acetate. The organic layer was washed with water and a saturated aqueous solution of common salt, dried over magnesium sulfate, and concentrated to give N (1-benzyl-4-piperidyl)-4-(N-acetyl-N-methylamino)benzenesulfonamide as a colorless viscous oil. This oil was dissolved in 4N aqueous hydrochloric acid and the obtained solution was heated under reflux for 3 hours. The resulting mixture was concentrated to give a solid residue. This residue was recrystallized from ethyl acetate to give the title compound as a white crystal (highly hygroscopic one) (5.80 g, overall yield of two steps: 80%).

m.p. (°C.): amorphous (highly hygroscopic).
¹H-NMR (400 MHz, DMSO-d₆) δ: 7.60 (1H, m), 7.54 (2H, m), 7.50 (2H, d, J=8.8), 7.44 (1H, m), 7.42 (2H, m), 6.60 (2H, d, J=8.8), 4.13 (2H, s), 3.18 (2H, m), 3.08 (2H, m), 2.87 (2H, m), 2.71 (3H, s), 1.73 (4H, m).

PREPARATIVE EXAMPLE 17

N-(4-Piperidyl)-4-(N-acetyl-N-methylamino)-benzenesulfonamide acetate

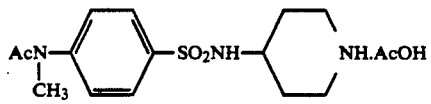

N-(1-Benzyl-4-piperidyl)-4-(N-acetyl-N-methylamino)benzenesulfonamide was prepared as a colorless oil from the 4-(N-acetyl-N-methylamino)benzenesulfonyl chloride (20.0 g, 80.8 mmol) and 4-amino-1-benzylpiperidine (18.16 ml, 88.9 mmol) in a similar manner to that described in Preparative Example 16. This oil was dissolved in ethanol (200 ml), followed by the addition of glacial acetic acid (10.0 ml). The obtained mixture was stirred in the presence of 10% palladium/carbon (water-containing one, 2.00 g) in a hydrogen atmosphere (1 atm) at 50° C for 5 hours and filtered to remove the catalyst. The filtrate was concentrated to precipitate a crystal. The resulting mixture was washed with ethyl acetate and filtered to give the title compound as a white crystal (29.70 g, overall yield of two steps: 100%).

m.p.: 177 to 184
¹H-NMR (400 MHz, DMSO-d₆) δ: 7.84 (2H, d, J=8.8), 7.55 (2H, d, J=8.8), 3.22 (3H, s), 3.11 (1H, m), 2.90 (2H, m), 2.47 (2H, m), 1.90 (3H, brs), 1.85 (3H, s), 1.57 (2H, m), 1.32 (2H, m).

PREPARATIVE EXAMPLE 18

N-[1-(2-Phenylethyl)-4-piperidyl]-4-(N-methyl-amino)benzenesulfonamide dihydrochloride

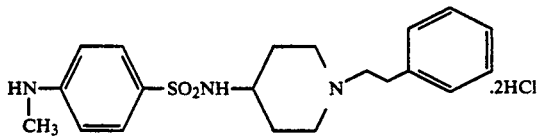

The N-(4-piperidyl)-4-(N-acetyl-N methylamino)benzenesulfonamide acetate (3.71 g, 10.6 mmol) prepared in Preparative Example 17 was dissolved in a suspension of sodium hydrogencarbonate (2.52 g) and potassium iodide (3.32 g) in dimethylformamide (50 ml), followed by the addition of 2-bromoethylbenzene (1.49 ml, 11.0 mmol). The obtained mixture was stirred at 70° C. for 3 hours, followed by the addition of water. The obtained mixture was extracted with ethyl acetate. The organic layer was washed with water and a saturated aqueous solution of common salt, dried over magnesium sulfate, and concentrated to give N-[1-(2-phenylethyl)-4-piperidyl]-4-(N-acetyl-N-methylamino)benzenesulfonamide as a colorless oil (3.19 g, yield: 77%).

This oil was dissolved in 1N aqueous sodium hydroxide (50 ml). The obtained solution was heated under reflux for 2 hours and acidified with 1N aqueous hydrochloric acid. The pH of the solution was adjusted to about 8 with an aqueous solution of sodium hydrogencarbonate. The resulting mixture was extracted with ethyl acetate and the organic layer was washed with water and a saturated aqueous solution of common salt, dried over magnesium sulfate, and concentrated to give the title compound in free form as a colorless oil (2.60 g). This oil was converted into a hydrochloride in ethyl acetate-ethanol to give the title compound as a white crystal (2.55 g, yield: 74%).

m.p. (°C.): amorphous (hygroscopic).
¹H-NMR (400 MHz, DMSO-d₆) δ: 7.55 (2H, d, J=8.8), 7.31 (3H, m), 7.22 (2H, m), 6.67 (2H, d, J=8.8), 3.45-3.00 (6H, m), 2.92 (2H, m), 2.72 (3H, s), 1.75 (4H, m).

PREPARATIVE EXAMPLE 19

N-{1-[2-(6-Methyl-2-pyridyl)ethyl]-4-piperidyl}-4-(N-methylamino)benzenesulfonamide

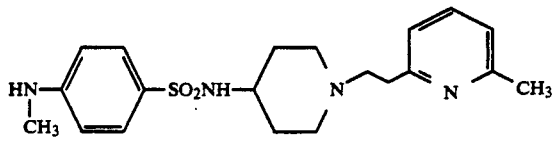

The N-(4-piperidyl)-4-(N-acetyl-N methylamino)benzenesulfonamide acetate (3.71 g, 10.0 mmol), 6-methyl-2-vinylpyridine (1.43 g, 12.0 mmol) and sodium acetate (0.82 g) were dissolved in a mixture comprising methanol (20 ml) and water (20 ml). The obtained solution was heated under reflux for 5 hours, followed by the addition of sodium hydroxide (3.20 g). The obtained mixture was heated under reflux for additional three hours and acidified with 2N aqueous hydrochloric acid. The pH of the mixture was adjusted to about 8 with an aqueous solution of sodium hydrogencarbonate. The resulting mixture was extracted with ethyl acetate. The organic layer was washed with water and a saturated aqueous solution of common salt, dried over magnesium sulfate and concentrated. The obtained oily residue was purified by column chromatography (chloroform : methanol : aqueous ammonia=90:9:1) and recrystallized from ethyl acetate/ether to give the title compound as a white crystal (2.71 g, overall yield of two steps: 70%).

m.p. (°C.): 80 to 84.
¹H-NMR (400 MHz, DMSO-d₆) δ: 7.53 (1H, t, J=8.0), 7.49 (2H, d, J=8.8), 7.20 (2H, d, J=7.2), 7.01 (2H, d, J=8.0), 6.58 (2H, d, J=8.8), 6.47 (1H, brq, J=5.2), 2.75 (6H, m), 2.72 (3H, d, J=5.2), 2.52 (2H, t, J=7.2), 1.88 (2H, brt), 1.52 (2H, m), 1.31 (2H, m), 2.40 (3H, s).

PREPARATIVE EXAMPLE 20

N-Methyl-4-[4-(2-phenylethyl)homopiperazinyl-sulfonylaniline

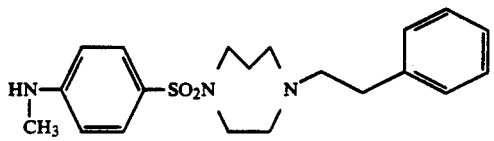

A suspension of 1 (2 phenylethyl)homopiperazine dihydrochloride (7.0 g, 25 mmol) in dichloromethane (100 ml) was cooled with ice, followed by the gradual addition of a solution of triethylamine (15.0 ml, 108 mmol) in dichloromethane (50 ml) thereto. The solid 4-(N acetyl-N methylamino)benzenesulfonyl chloride (6.20 g, 25.0 mmol) prepared in Preparative Example 12 was added as such to the obtained solution at 0° C., followed by the addition of dichloromethane (50 ml). The ice bath was taken out to raise the temperature of the resulting mixture to room temperature. The mixture was stirred for one hour and 40 minutes.

A saturated aqueous solution (100 ml) of sodium hydrogencarbonate was added to the obtained suspension to conduct phase separation. The aqueous layer was further extracted with dichloromethane. The organic layers were combined, washed with a saturated aqueous solution of common salt, dried over magnesium sulfate, and concentrated in a vacuum. The obtained oil (10.4 g) was purified by column chromatography [benzene/acetone (3:1)→(1:1)] to give N-acetyl-N-methyl-4-[4-(2-phenylethyl)homopiperazinyl]sulfonylaniline as an oil (9.9 g, 94%).

This oil (9.9 g) was dissolved in dioxane (40 ml), followed by the addition of 4N hydrochloric acid (100 ml). The obtained mixture was heated under reflux for one hour and 15 minutes.

The obtained solution was cooled by allowing to stand and concentrated in a vacuum. The obtained residue was cooled with ice, followed by the successive addition of water (50 ml) and concentrated aqueous ammonia (50 ml) in this order. The obtained mixture was extracted with dichloromethane. The organic layer was washed with a saturated aqueous solution of common salt, dried over magnesium sulfate and dried in a vacuum. The obtained oil (9.0 g) was purified by column chromatography [benzene/acetone (10:1)→(5:1)] to give the title compound as an oil (8.26 g, 93%).

$^1$H-NMR (400 MHz, CDCl$_3$) δ: 7.58 (2H, d, J=8.9), 7.26 (2H, m), 7.17 (3H, m), 6.58 (2H, d, J=8.9), 4.23 (1H, brq, J=5.1), 3.34 (4H, m), 2.88 (3H, d, J=5.1), 2.75 (4H, m), 2.73 (4H, s), 1.83 (2H, quint, J=6.0).

PREPARATIVE EXAMPLES 21 TO 58

Amine derivatives of Preparative Examples 21 to 58 listed in Table 3 were each prepared in a similar manner to that described in one of Preparative Examples 12 to 20.

TABLE 3

HN(R$^4$)—C$_6$H$_4$—SO$_2$N(R$^5$)—R$^6$

| Prep. No. | R$^4$ | —N(R$^5$)—R$^6$ | m.p. (°C.) | $^1$H-NMR δ |
|---|---|---|---|---|
| 21 | H | —NH—cyclohexyl · HCl | 102–107 | (90 MHz, DMSO-d$_6$): 7.52(2H, d, J=9.0), 7.24(1H, m), 6.82(2H, d, J=9.0), 2.84(1H, m), 1.8–0.8(10H, m) |
| 22 | H | —N(CH$_3$)—cyclohexyl | 139–140 | (400 MHz, CDCl$_3$): 7.56(2H, d, J=8.8), 6.67(2H, d, J=8.8), 4.13(2H, brs), 3.71(1H, brtt, J=11.8, 3.7), 2.70(3H, s), 1.72(2H, m), 1.60(1H, m), 1.51(2H, m), 1.27(4H, m), 0.99(1H, brqt, J=12.8, 4.0) |
| 23 | H | —N(CH$_3$)—cyclohexyl | 119–122 | (400 MHz, DMSO-d$_6$): 7.60(2H, d, J=8.8), 7.37(1H, br), 6.98(1H, d, J=8.8), 3.05(1H, m), 1.60(2H, m), 1.55–1.30(8H, m), 1.22(2H, m) |
| 24 | CH$_3$ | —NHCH$_3$ | 143–148 | (90 MHz, DMSO-d$_6$): 7.56(2H, br, D$_2$O exchange), 7.50(2H, d, J=8.4), 6.75(2H, d, J=8.4), 2.72(3H, s), 2.32(3H, s) |
| 25 | CH$_3$ | —NHCH$_2$CH$_2$N(CH$_3$)$_2$ · 2HCl | amorphous (highly hygroscopic) | (90 MHz, DMSO-d$_6$): 7.54(2H, d, J=8.4), 6.68(2H, d, J=8.4), 6.48(4H, br, D$_2$O exchange), 3.06(4H, br, D$_2$O→sharpen m), 3.74(6H, s), 3.70(3H, s) |
| 26 | CH$_3$ | —NHCH$_2$CH$_2$CH$_2$N(CH$_3$)$_2$ | oil | (90 MHz, CDCl$_3$): 7.59(2H, d, J=9.0), 6.55(2H, d, J=9.0), 4.41(1H, brq, J=5.0), 3.00(2H, t, J=6.5), 2.87(3H, d, J=5.0), 2.30(2H, t, J=6.5), 2.17(6H, s), 1.59(2H, quint, J=6.5) |
| 27 | CH$_3$ | —NH—cyclopentyl · HCl | 143–147 | (400 MHz, DMSO-d$_6$): 7.51(2H, d, J=8.8), 6.68(2H, d, J=8.8), 3.30(1H, m), 2.73(3H, s), 1.53(2H, m), 1.32(2H, m) |
| 28 | CH$_3$ | —NH$_2$ | 166–167 | 400 MHz, DMSO-d$_6$): 7.51(2H, d, J=8.8), 6.91(2H, s), 6.57(2H, |

TABLE 3-continued

-C6H4-SO2N(R5)(R6))

| Prep. No. | R⁴ | –N(R⁵)R⁶ | m.p. (°C.) | ¹H-NMR δ |
|---|---|---|---|---|
| | | | | d, J=8.8), 6.37(1H, brq, J=5.0), 2.71(3H, d, J=5.0) |
| 29 | CH₃ | 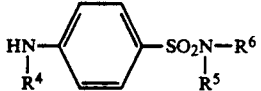—NH-cyclohexyl · HCl | 130~131 | [400 MHz, CDCl₃-DMSO-d₆ (7:1)] - 7 8.73(2H, br, s), 7.91(2H, d, J=8.5), 7.56(2H, d, J=8.5), 2.99(3H, s), 2.99(1H), 1.67(4H, m), 1.52(1H, brd, J=12.1), 1.18(4H, m), 1.10(1H, m) |
| 30 | CH₃ | 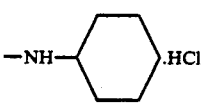—N(CH₃)-cyclohexyl | 126~127 | (400 MHz, CDCl₃): 7.58(2H, d, J=9.0), 6.57(2H, d, J=9.0), 4.31(1H, brs), 3.72(1H, tt, J=12.8, 4.3), 2.87(3H, brs), 2.69(3H, s), 1.72(2H, m), 1.59(1H, m), 1.52(2H, m), 1.28(4H, m), 0.99(1H, qt, J=12.8, 3.7) |
| 31 | CH₃ | 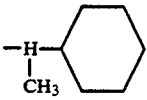—NH-cyclooctyl · HCl | 130~135 | (400 MHz, DMSO-d₆: 7.51(2H, d, J=8.8), 6.68(2H, d, J=8.8), 3.05(1H, m), 2.73(3H, s), 1.60~1.50(12H, m), 1.25(2H, m) |
| 32 | CH₃ | 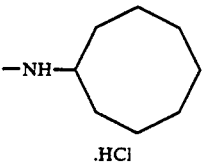—NH-indanyl | 117~119 | (400 MHz, DMSO-d₆): 7.65(1H, d, J=8.7), 7.57(2H, d, J=8.8), 7.21~7.09(4H, m), 6.62(2H, d, J=8.8), 6.51(1H, br), 4.56(1H, q like, J=7.8), 2.79(1H, m), 2.74(3H, d, J=4.2), 2.62(1H, m), 2.01(1H, m), 1.60(1H, m) |
| 33 | CH₃ | 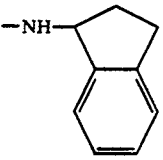tetrahydronaphthyl | 161~162 | (400 MHz, DMSO-d₆): 7.58(1H, d, J=8.1), 7.56(2H, d, J=8.8), 7.20~7.00(4H, m), 6.62(2H, d, J=8.8), 6.50(1H, brq, J=4.5), 4.40(1H, m), 2.74(3H, d, J=4.5), 2.32(2H, m), 1.78(1H, m), 1.56(3H, m) |
| 34 | CH₃ | 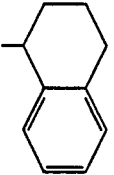tetrahydronaphthyl | 110~113 | (400 MHz, DMSO-d₆): 7.54(2H, d, J=8.8), 7.32(1H, d, J=6.2), 7.50~6.99(3H, m), 6.95(1H, m), 6.60(2H, d, J=8.8), 6.49(1H, brq, J=5.0), 3.20(1H, m), 2.83~2.54(3H, m), 1.80(1H, m), 1.56(1H, m) |
| 35 | CH₃ | 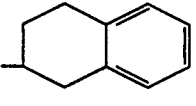NH-CH₂-pyridyl · 2HCl | 196~201 | (400 MHz, DMSO-d₆): 8.78(2H, d, J=5.5), 8.49(1H, t, J=7.9), 8.30(1H, br), 7.98(2H, d, J=8.1), 7.90(1H, t, J=6.5), 7.52(2H, d, J=8.8), 6.60(2H, d, J=8.8), 4.36(2H, s), 2.71(3H, s) |
| 36 | CH₃ | 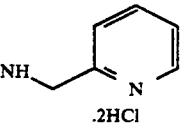—NH-CH₂CH₂-pyridyl | 99~100 | (400 MHz, DMSO-d₆): 8.44(1H, ddd, J=4.8, 1.8, 1.2), 7.67(1H, td, J=7.6, 1.8), 7.47(2H, d, J=8.8), 7.21(2H, m), 6.59(2H, d, J=8.8), 6.49(1H, brq, J=4.9), 3.00(2H, q like, J=7.0), 2.80(2H, t, J=7.5), 2.71(3H, d, J=4.9) |
| 37 | CH₃ | 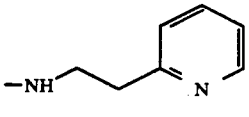—N(CH₃)-CH₂CH₂-pyridyl | oil | (400 MHz, DMSO-d₆): 8.50(1H, brd, J=4.8), 7.61(1H, t, d, J=8.0, 1.8), 7.56(2H, d, J=8.8), 7.23(1H, d, J=8.0), 7.13(1H, dd, J=8.0, 4.8), 6.57(2H, d, J=8.8), 4.30(1H, brq, J=5.2), 3.38(2H, t, J=7.0), 3.04(2H, t, J=7.0), 2.87(3H, d, J=5.2) |

TABLE 3-continued

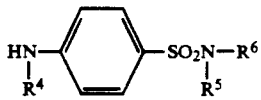

| Prep. No. | R⁴ | −N(R⁵)R⁶ | m.p. (°C.) | ¹H-NMR δ |
|---|---|---|---|---|
| 38 | CH₃ | −NH-CH₂CH₂-(2-pyridyl)-CH₂ .2HCl | 170~172 | (400 MHz, DMSO-$d_6$): 8.32(1H, brt, J=8.0), 7.71(1H, d, J=8.0), 7.65(1H, 1d, J=8.0), 7.42(2H, d, J=8.8), 6.57(2H, d, J=8.8), 3.13(4H, brs), 2.72(3H, s), 2.71(3H, d, J=5.2) |
| 39 | CH₃ | −NH-(norbornyl) .HCl | 139~143 | (400 MHz, DMSO-$d_6$): 7.49(2H, d, J=8.8), 6.66(2H, d, J=8.8), 2.85(1H, m), 2.73(3H, s), 2.08(1H, brs), 1.95(1H, brs), 1.48~1.12(5H, m), 0.95(3H, m) |
| 40 | CH₃ | −NH-(norbornyl) .HCl | amorphous 115~130 | (400 MHz, DMSO-$d_6$): 7.50(2H, d, J=8.8), 6.66(2H, d, J=8.8), 3.13(1H, m), 2.73(3H, s), 2.01(2H, brs), 1.62(2H, m), 1.38(1H, m), 1.14(4H, m), 0.96(1H, m) |
| 41 | CH₃ | −NH-(quinuclidinyl) .2HCl | 169~176 | (400 MHz, DMSO-$d_6$): 10.46(1H, brs), 7.80(1H, brs), 7.54(2H, d, J=8.8), 6.63(2H, d, J=8.8), 3.44(1H, m), 3.30(1H, m), 3.20~2.95(4H, m), 2.80(1H, m), 2.06~1.56(5H, m) |
| 42 | CH₃ | −NH-(5,6,7,8-tetrahydroquinolin-8-yl) | 109~110 | (400 MHz, DMSO-$d_6$): 8.33(1H, brd, J=4.4), 7.59(2H, d, J=8.8), 7.49(1H, d, J=7.5), 7.20(2H, m), 6.59(2H, d, J=8.8), 6.47(1H, brq, J=4.5), 4.18(1H, m), 2.71(3H, d, J=4.5), 2.69(2H, m), 1.90~1.55(4H, m) |
| 43 | CH₃ | −NH-CH₂-C₆H₄-CH₂-(pyrrolidinyl) | oil | (400 MHz, CDCl₃): 7.67(2H, d, J=8.9), 7.25(2H, d, J=8.1), 7.15(2H, d, J=8.1), 6.59(2H, d, J=8.9), 4.54(1H, brt, J=8.9), 4.28(1H, brq, J=5.1), 4.07(2H, d, J=5.9), 3.58(2H, s), 2.89(3H, d, J=5.1), 2.49(4H, m), 1.77(4H, m) |
| 44 | CH₃ | −NH-CH₂-C₆H₄-CH₂-(piperidinyl) | 102~103 | (400 MHz, CDCl₃): 7.67(2H, d, J=8.8), 7.22(2H, d, J=8.1), 7.14(2H, d, J=8.1), 6.59(2H, d, J=8.8), 4.54(1H, brt, J=6.2), 4.30(1H, brq, J=5.2), 4.06(2H, d, J=6.2), 3.41(2H, s), 2.89(3H, d, J=5.2), 2.33(4H, brs), 1.55(4 quint, J=5.5), 1.42(2H, brd, J=5.1) |
| 45 | CH₃ | −NH-(1-methylpiperidin-4-yl) | amorphous | [400 MHz, CDCl₃-DMSO-$d_6$ (10:1)]: 7.42(2H, d, J=9.0), 6.38(2H, d, J=9.0), 5.92(2H, brd, J=7.0), 4.94(1H, brq, J=5.0), 2.78(1H, m), 2.64(3H, d, J=5.0), 2.48(2H, brd, J=11.7), 2.01(3H, s), 1.76(2H, brt, J=11.7), 1.52(2H, brdd, J=11.7, 3.9), 1.30(2H, brqd, J=11.7, 3.6) |
| 46 | CH₃ | −NH-(1-isobutylpiperidin-4-yl) | 145~146 | (400 MHz, DMSO-$d_6$): 7.49(2H, d, J=8.8), 7.20(1H, brd, J=7), 6.58(2H, d, J=8.8), 6.47(1H, brq, J=4.7), 2.78(1H, m), 2.71(3H, d, J=4.7), 2.62(2H, m), 1.92(2H, m), 1.80~1.60(3H, m), 1.50(2H, m), 1.32(2H, m), 0.79(6H, d, J=6.4) |

TABLE 3-continued

Structure: HN(R⁴)—C₆H₄—SO₂N(R⁵)(R⁶)

| Prep. No. | R⁴ | —N(R⁵)R⁶ | m.p. (°C.) | ¹H-NMR δ |
|---|---|---|---|---|
| 47 | CH₃ | —NH-(4-piperidinyl)-N-CH₂CH₂-(3,4-dimethoxyphenyl) | 123~124 | (400 MHz, DMSO-d₆): 7.49(2H, d, J=8.8), 7.20(1H, d, J=7.1), 6.80(2H, m), 6.66(1H, d, J=8.0), 6.58(2H, d, J=8.8), 6.47(1H, brq), 3.71(3H, s), 3.69(3H, s), 2.86~2.70(3H, m), 2.72(3H, d, J=3.2), 2.57(2H, brt, J=7), 2.39(2H, brt, J=7), 1.87(2H, m), 1.52(2H, m), 1.32(2H, m) |
| 48 | (CH₃)₂CH— | —NH₂ | 138~139 | (400 MHz, DMSO-d₆): 7.48(2H, d, J=8.8), 6.88(2H, s), 6.58(2H, d, J=8.8), 6.17(1H, d, J=7.6), 3.60(1H, m), 1.13(6H, d, J=6.4) |
| 49 | CH₃ | —NH-(4-piperidinyl)-N-CH₂CH₂-(3-pyridyl) | 150~152 | (400 MHz, DMSO-d₆): 8.40(1H, brs), 8.37(1H, brd, J=4.7), 7.61(1H, d, J=8.0), 7.48(2H, d, J=8.8), 7.27(1H, dd, J=6.5, 4.7), 7.19(1H, d, J=6.5), 6.58(2H, d, J=8.8), 6.47(1H, br), 2.85~2.64(3H, m), 2.71(3H, d, J=4.9), 2.67(2H, t, J=7), 2.42(2H, t, J=7), 1.88(2H, m), 1.52(2H, m), 1.31(2H, m) |
| 50 | CH₃ | —NH-(azepan-3-yl)-N-CH₂-(2-pyridyl) | oil | (400 MHz, DMSO-d₆): 7.43(2H, d, J=8.8), 7.36~7.27(3H, m), 7.21(1H, t like, J=6.6), 6.58(2H, d, J=8.8), 6.55(1H, m), 3.72(1H, d, J=16), 3.68(1H, d, J=16), 3.38(1H, m), 3.33(2H, s), 3.15(1H, m), 2.98(4H, m), 2.75(1H, m), 2.71(3H, d, J=4.9), 2.64(1H, m), 1.77(1H, m), 1.64(2H, m), 1.52(1H, m), 1.31(1H, m) |
| 51 | CH₃ | 4-benzylpiperazin-1-yl | 146~147 | (90 MHz, CDCl₃): 7.50(2H, d, J=9.0), 7.21(5H, s), 6.55(2H, d, J=9.0), 4.25(1H, brq, J=5.8), 3.48(2H, s), 2.98(4H, m), 2.88(3H, d, J=5.8), 2.54(4H, m) |
| 52 | CH₃ | 4-(3-pyridylmethyl)piperazin-1-yl | 155~156 | (400 MHz, CDCl₃): 8.48(2H, d like), 7.56(1H, brd, J=7.8), 7.52(2H, d, J=8.8), 7.21(1H, dd, J=7.8, 4.8), 6.59(2H, d, J=8.8), 4.31(1H, brq, J=5.2), 3.48(2H, s), 2.99(4H, brs), 2.88(3H, d, J=5.2), 2.51(4H, t like) |
| 53 | CH₃ | 4-phenethylpiperazin-1-yl | 203~204 | [(400 MHz, CDCl₃-DMSO-d₆ (7:1)]: 7.48(2H, d, J=8.9), 7.25(2H, m), 7.16(3H, m), 6.61(2H, d, J=8.9), 5.60(1H, brq, J=5.0), 2.97(2H, m), 2.96(4H, s), 2.84(3H, d, J=5.0), 2.72(2H, m), 2.59(4H, m) |
| 54 | CH₃ | 4-benzyl-1,4-diazepan-1-yl | 140~141 | (400 MHz, CDCl₃): 7.57(2H, d, J=8.8), 7.28(5H, m), 6.58(2H, d, J=8.8), 4.24(1H, brq, J=5.1), 3.60(2H, s), 3.34(4H, m), 2.88(3H, d, J=5.1), 2.66(4H, m), 1.80(2H, quint, J=5.9) |
| 55 | CH₃ | 4-(cyclohexylmethyl)-1,4-diazepan-1-yl | 122~123 | (400 MHz, CDCl₃): 7.57(2H, d, J=8.9), 6.57(2H, d, J=8.9), 4.26(1H, brq, J=4.91), 3.31(4H, m), 2.88(3H, d, J=4.9), 2.63(4H, m), 2.21(2H, d, J=7.0), 1.77(2H, quint, J=6), 1.69(4H, m), 1.35(1H, m), 1.6(4H, m), 0.79(2H, m) |

TABLE 3-continued

HN—⟨benzene⟩—SO₂N—R⁶ with R⁴ on N and R⁵ on N

| Prep. No. | R⁴ | —N(R⁶)R⁵ | m.p. (°C.) | ¹H-NMR δ |
|---|---|---|---|---|
| 56 | CH₃ | —NH—CH(CH₃)₂ ·HCl | 120–128 | (400 MHz, DMSO-d₆): 7.49(2H, d, J=8.8), 7.07(1H, br), 6.61(2H, d, J=8.8), 3.10(1H, m), 2.71(3H, s), 0.96(6H, d, J=7) |
| 57 | CH₃ | —N(morpholino) ·HCl | 136–140 | (400 MHz, DMSO-d₆): 7.42(2H, d, J=8.8), 6.67(2H, d, J=8.8), 3.61(4H, m), 2.76(4H, m), 2.73(3H, s) |
| 58 | CH₃ | (4-propylpyridyl) | 125–127 | (400 MHz, DMSO-d₆): 8.41(2H, d, J=6.1), 7.46(2H, d, J=8.8), 7.18(1H, t, J=6.8), 7.14(2H, d, J=6.1), 6.59(2H, d, J=8.8), 6.50(1, brq, J=5.0) |

In Preparative Examples 21 to 23, known 4-(N-acetylamino)benzenesulfonyl chloride was used instead of the 4-(N-acetyl-N-methylamino)benzenesulfonyl chloride prepared in Preparative Example 12.

EXAMPLE 1 synthesis of Compound 99

N-(2-Indanyl)-4-{N-methyl-N-[(E)-3-(3,4-diacetoxyphenyl)-2-propenoyl]amino}-benzenesulfonamide

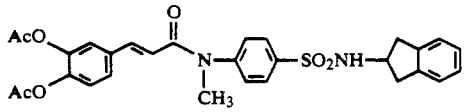

A solution of 3,4-diacetoxycinnamoyl chloride (5.61 g, 19.9 mmol) in dichloromethane (50 ml) was dropped into a solution of the N-(2-indanyl)-4-(methylamino)-benzenesulfonamide (5.00 g, 16.6 mmol) prepared in Preparative Example 14 in pyridine (50 ml) at 0° C. The obtained mixture was stirred at room temperature for 2 hours, followed by the addition of water. The obtained mixture was extracted with ethyl acetate. The organic layer was washed with 1N aqueous hydrochloric acid and a saturated aqueous solution of common salt, dried over magnesium sulfate, and concentrated to give a solid residue. This residue was recrystallized from ethyl acetate/ether/isopropyl ether to give the title compound as a white crystal (8.90 g, 100%).

m.p (°C.): 152–153 (iso-Pr₂O).

¹H-NMR (400 MHz, DMSO-d₆) δ: 8.11 (1H, d, J=7.2), 7.91 (2H, d, J=8.8), 7.58 (2H, d, J=8.8), 7.58–7.42 (3H, m), 7.20 (1H, d, J=8.4), 7.11 (4H, s), 6.61 (1H, brd, J=15.4), 3.94 (1H, m), 3.38 (3H, s), 2.98 (2H, dd, J=16.8), 2.75 (2H, dd, J=16.8), 2.26 (3H, s), 2.18 (3H, s).

Mass m/e (FAB): 549 (MH⁺), 507, 307, 205, 154 (base).

elemental analysis as C₂₉H₂₈N₂O₇S

| | C | H | N |
|---|---|---|---|
| calculated (%) | 63.49 | 5.14 | 5.11 |
| found (%) | 63.57 | 5.19 | 4.87 |

EXAMPLE 2

N-(2-Indanyl)-4-{N-methyl-N-[(E)-3-(3,4-dihydroxyphenyl)-2-propenoyl]amino}benzene-sulfonamide

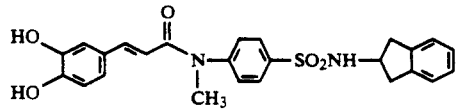

The N-(2-indanyl)-4-{N-methyl-N-[(E)-3-(3,4-dihydroxyphenyl)-2-propenoyl]amino}benzenesulfonamide (8.90 g, 16.6 mmol) prepared in Example 1 was suspended in a mixture comprising methanol (80 ml) and tetrahydrofuran (80 ml), followed by the addition of concentrated hydrochloric acid (30 ml). The obtained mixture was stirred at 60° C. for 20 minutes, followed by the addition of water. The obtained mixture was extracted with ethyl acetate. The organic layer was washed with water and a saturated aqueous solution of common salt, dried over magnesium sulfate, and concentrated to give a solid residue. The residue was recrystallized from ether to give the title compound as a white crystal (7.17 g, yield: 93%).

m.p. (°C.): 201–203 (Et₂O).

¹H-NMR (90 MHz, DMSO-d₆) δ: 9.20, 8.00 (each 1H, br, D₂O exchange), 7.92 (2H, d, J=8.3Hz), 7.55 (2H, d, J=8.4Hz), 7.40 (1H, d, J=15.4Hz), 7.11 (4H, s), 6.87-6.35 (3H, m), 6.22 (1H, d, J=15.4Hz), 3.88 (1H, m, D₂O sharpen), 3.35 (3H, s), 3.15-2.55 (4H, m).

Mass m/e (FD): 464 (M⁺).

| elemental analysis as C25H24N2O5S | | | |
|---|---|---|---|
| | C | H | N |
| calculated (%) | 64.64 | 5.21 | 6.03 |
| found (%) | 64.80 | 5.37 | 5.92 |

| elemental analysis as C29H30N4O7S.2HCl.½H2O | | | |
|---|---|---|---|
| | C | H | N |
| found (%) | 52.78 | 5.10 | 8.15 |

EXAMPLE 4

N-(1-Benzyl-4-piperidyl)-4-{N-methyl-N-l(E)-3-(4-methylsulfonylphenyl)-2-propenoyl]amino}-benzenesulfonamide

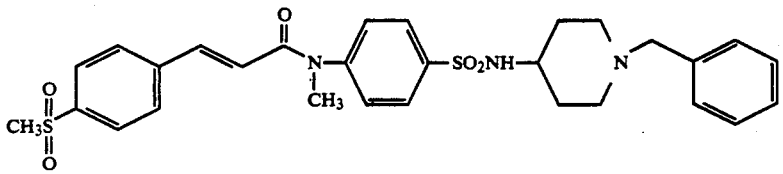

EXAMPLE 3

N-(2-Indanyl)-4-{N-methyl-N-[(E)-3-(3,4-diglycyloxyphenyl)-2-propenoyl]amino}benzene-sulfonamide dihydrochloride

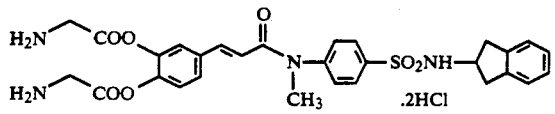

Dicyclohexylcarbodiimide (DCC, 0.27 g) was added to a suspension of the N-(2-indanyl)-4-{N-methyl-N-[(E)-3-(3,4-dihydroxyphenyl)-2-propenoyl]amino}benzenesulfonamide (0.30 g, 0.65 mmol) and N-(tert-butoxycarbonyl)glycine (0.23 g, 1.29 mmol) in ethyl acetate (7 ml). The obtained mixture was stirred at room temperature overnight and filtered. The filtrate was concentrated to give an N-BOC derivative of the title compound as a white crystal (0.47 g, yield: 92 %). This crystal (0.42 g, 0.537 mmol) was dissolved in ethyl acetate (2.0 ml), followed by the addition of a 1.5N solution (2.0 ml) of hydrochloric acid in ethyl acetate. The obtained mixture was stirred at room temperature for one hour.

The precipitated crystal was recovered by filtration to give the title compound as a white crystal (0.32 g, yield: 91%).

m.p. (°C.): 120~127 (AcOEt).

¹H-NMR (90 MHz, DMSO-d6) δ: 8.73 (6H, br, D2O exchange), 8.17 (1H, d, J=7.0H2, D2O exchange), 7.92 (2H, d, J=8.8Hz), 6.91~7.75 (6H, m), 7.11 (4H, s), 6.60 (1H, d, J=15.4Hz), 4.19 (4H, m), 3.98 (3H, m), 3.39 (3H, s), 3.20-2.56 (4H, m).

Mass m/e (FAB): 579 (MH ), 522, 465, 410, 282, 225, 185 (base)

| elemental analysis as C29H30N4O7S.2HCl.½H2O | | | |
|---|---|---|---|
| | C | H | N |
| calculated (%) | 52.98 | 4.70 | 8.52 |

The 3 (4 methylsulfonyl)cinnamic acid (1.56 g, 6.67 mmol) prepared in Preparative Example 5 was suspended in dichloromethane (20 ml), followed by the addition of oxalyl chloride (2.01 ml, 23.3 mmol) and dimethylformamide (two drops). The obtained mixture was stirred at room temperature for one hour and concentrated to give 3 (4-methylsulfonyl)cinnamoyl chloride as a white crystal. This chloride was dissolved in dichloromethane (25 ml) to obtain a solution. This solution was dropped into a solution of the N-(1-benzyl-4-piperidyl)-4-(N-methylamino)benzenesulfonamide dihydrochloride (2.62 g, 6.06 mmol) prepared in Preparative Example 16 in pyridine (25 ml) at 0° C. The obtained mixture was stirred at room temperature for 2 hours, followed by the addition of water. The obtained mixture was extracted with ethyl acetate. The organic layer was washed with water and a saturated aqueous solution of common salt, dried over magnesium sulfate, and concentrated to give a solid residue. This residue was purified by flash column chromatography (chloroform/methanol/aqueous ammonia=98:2:0.2) and recrystallized from ethyl acetate/ether to give the title compound as a white crystal (2.60 g, yield: 76%).

m.p. (°C.): 189~190 (AcOEt-Et2O).

¹H-NMR (400 MHz, CDCl3) δ: 7.95 (2H, d, J=8.6Hz), 7.88 (2H, d, J=8.4Hz), 7.74 (1H, d, J=15.4Hz), 7.50 (2H, d, J=8.4Hz), 7.36 (2H, d, J=8.6Hz), 7.27 (5H, m), 6.45 (1H, d, J=15.4Hz), 4.27 (1H, d, J=7.7Hz), 3.46 (2H, s), 3.46 (3H, s), 3.27 (1H, m), 3.02 (3H, s), 2.75 (1H, brd, J=12.1Hz), 2.05 (2H, t like, J=8Hz), 1.80 (2H, m), 1.52 (2H, m).

Mass m/e (FAB): 568 (MH+), 490, 360, 209, 189, 172 (base)

| elemental analysis as C29H33N3O5S2 | | | |
|---|---|---|---|
| | C | H | N |
| calculated (%) | 61.36 | 5.85 | 7.40 |
| found (%) | 61.08 | 5.98 | 7.42 |

EXAMPLE 5

N-[1-(2-Phenylethyl)-4-piperidyl]-4-{N-methyl-N-[(E)-3-(4-methylsulfonylphenyl)-2-propenoyl]-amino}benzenesulfonamide

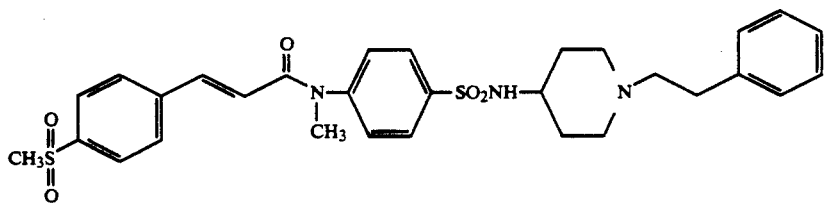

A solution of 3-(4-methylsulfonyl)cinnamoyl chloride [3.10 mmol, prepared from 3-(4-methylsulfonyl)cinnamic acid (0.70 g) in a similar manner to that of Example 4] in dichloromethane (10 ml) was dropped into a solution of the N-11-(2-phenylethyl)-4-piperidyl]-4-(N-methylamino)benzenesulfonamide dihydrochloride (1.26 g, 2.82 mmol) prepared in Preparative Example 18 in pyridine (20 ml) at 0° C. The obtained mixture was stirred at room temperature for 2 hours, followed by the addition of water. The obtained mixture was extracted with ethyl acetate. The organic layer was washed with water and a saturated aqueous solution of common salt, dried over magnesium sulfate, and concentrated to give a solid residue. The residue was recrystallized from ethyl acetate/ether to give the title compound as a white crystal (1.04 g, yield: 63%).

m.p. (°C.): 173~176 (AcOEt-Et$_2$O).

$^1$H-NMR (400 MHz, CDCl$_3$) δ: 7.96 (2H, d, J=8.6Hz), 7.87 (2H, d, J=8.4Hz), 7.74 (1H, d, J=15.6Hz), 7.50 (2H, d, J=8.4Hz), 7.37 (2H, d, J=8.6Hz), 7.28 (2H,m), 7.17 (3H, m), 6.46 (1H, d, J=15.6Hz), 4.68 (1H, d, J=6.0), 3.46 (3H, s), 3.28 (1H, m), 3.01 (3H, s), 2.86 (2H, brd, J=12.3Hz), 2.75 (2H, m), 2.56 (2H, m), 2.11 (2H, brt, J=8Hz), 1.87 (2H, m), 1.55 (2H, m).

Mass m/e (FAB): 582 (MH+), 490, 307, 154 (base).

| elemental analysis as C$_{30}$H$_{35}$N$_3$O$_5$S$_2$ | | | |
|---|---|---|---|
| | C | H | N |
| calculated (%) | 6.194 | 6.06 | 7.22 |
| found (%) | 61.67 | 6.09 | 7.05 |

EXAMPLES 6 TO 99

The compounds of Examples 6 to 99 which will be described below were each prepared in a similar manner to that of Example 4 or 5.

EXAMPLE 6

N-Methyl-N-[2-(6-methyl-2-pyridyl)ethyl]-4-{N-methyl-N-[(E)-3-(4-methylsulfonylphenyl)-2-propenoyl]amino}benzenesulfonamide hydrochloride

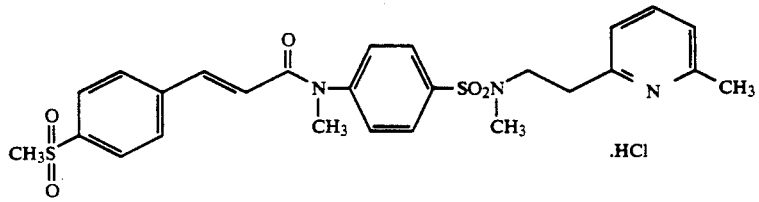

m.p. (°C.): 164~167 (EtOH-AcOEt).

$^1$H-NMR (90 MHz, DMSO-d$_6$) δ: 8.38 (1H, t, J=7.9Hz), 8.00~7.44 (11H, m), 6.76 (1H, d, J=15.4Hz), 3.60~3.20 (4H, m), 3.40 (3H, s), 3.21 (3H, s), 2.83 (3H, s), 2.78 (3H, s).

Mass m/e (FAB): 528 (MH+ base), 314, 209, 170, 149, 107.

| elemental analysis as C$_{26}$H$_{29}$N$_3$O$_5$S$_2$.HCl | | | |
|---|---|---|---|
| | C | H | N |
| calculated (%) | 55.36 | 5.36 | 7.45 |
| found (%) | 55.26 | 5.15 | 7.29 |

EXAMPLE 7

(E)-N-Methyl-N-{4-[4-(2-phenylethyl]homopiperazinyl]sulfonylphenyl}-3-(4-methylsulfonylphenyl)-2-propenamide

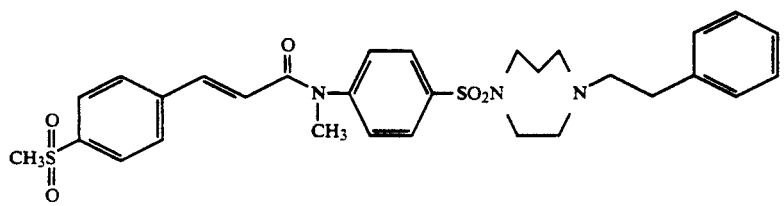

m.p. (°C.): 203~207 (EtOH-AcOEt-MeOH).

¹H-NMR (400 MHz, CDCl₃-DMSOd₆ (10:1) δ: 7.92 (2H, d, J=8.4Hz), 7.85 (2H, d, J=8.4Hz), 7.76 (1H, d, J=15.5Hz), 7.56 (2H, d, J=8.4Hz), 7.44 (2H, d, J=8.4Hz), 7.35~7.23 (5H, m), 6.51 (1H, d, J=15.5Hz), 3.81 (2H, m), 3.49 (3H, s), 3.27 (6H, m), 3.06 (3H, s), 2.48 (6H, m).

Mass m/e (FAB): 582 (MH+), 490, 372, 111 (base).

| elemental analysis as C₃₀H₃₅N₃O₅S₂.HCl | | | |
|---|---|---|---|
| | C | H | N |
| calculated (%) | 58.28 | 5.87 | 6.80 |
| found (%) | 58.20 | 5.67 | 6.71 |

High MASS: as C₂₉H₃₄N₄O₅S₂: calculated (%) 582.1970 (M+) found (%) 582.1964

EXAMPLE 9

(±)-N-[1-Benzyl-3-hexamethyleneimino]-4-{N-methyl-N-[(E)-3-(4-methylsulfonylphenyl)-2-propenoyl]amino}benzenesulfonamide

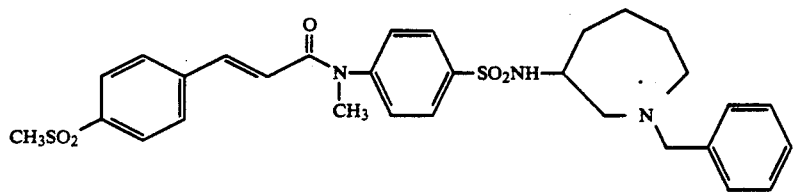

m.p. (°C.): 88~92 (amorphous, iso-Pr₂O).

¹H-NMR (90 MHz, DMSO-d₆) δ: 8.00~7.32 (10H, m), 7.23 (5H, m), 6.61 (1H, d, J=15.3Hz), 3.49 (2H, s), 3.18 (3H, s), 1.80~1.20 (6H, m).

Mass m/e (FAB): 582 (MH+, base), 232, 203, 188.

High MASS: as C₃₀H₃₅N₃O₅S₂: calculated (%) 582.2097 (MH+). found (%) 582.2102.

EXAMPLE 10

N-[1-(2-Methylpropyl)-4-piperidyl)-4-{N-methyl-N-(E)-3-(4-methylsulfonylphenyl)-2-propenoyl]-amino}benzenesulfonamide

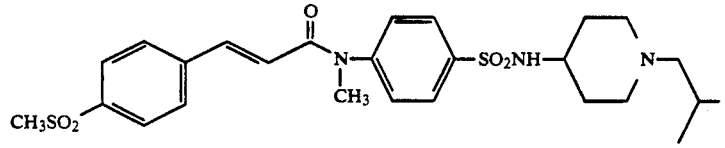

m.p. (°C.): 147~148 (AcOEt-Et₂O)

¹H-NMR (400 MHz, CDCl₃) δ: 7.96 (2H, d, J=8.6Hz), 7.87 (2H, d, J=8.4Hz), 7.74 (1H, d,

EXAMPLE 8

(±)-N-[1-(2-Pyridylmethyl)-3-hexamethyleneimino]-4-{N-methyl-N-[(E)-3-(4-methylsulfonylphenyl)-2-propenoyl]amino}benzenesulfonamide dihydrochloride

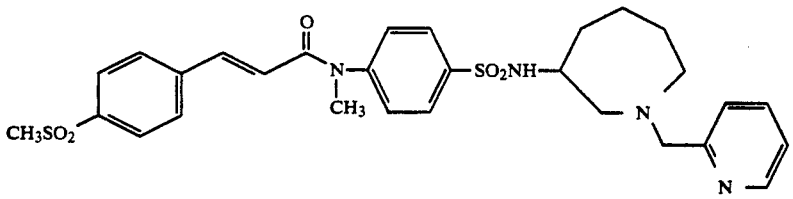

.2HCl m.p. (°C.): 145~148 (Et₂O-AcOEt).

¹H-NMR (400 MHz, DMSO-d₆ δ (free form): 7.87 (2H, d, J=8.4Hz), 7.85 (2H, d, J=8.8Hz), 7.73 (1H, d, J=15.6Hz), 7.51 (2H, d, J=8.2Hz), 7.37~7.21 (6H, m), 6.44 (1H, d, J=15.6Hz), 3.87 (1H, d, J=13.2Hz), 3.51 (1H, dd, J=14.2, 3.9Hz), 3.44 (3H, s), 3.35 (1H, m), 3.28 (1H, m), 3.07 (1H, dd, J=14.2, 7.6Hz), 3.02 (3H, s), 2.92 (1H, m), 2.00~1.60 (4H, m), 1.47 (2H, m).

Mass m/e (FAB): 582 (MH ), 475, 374, 203, 106 (base).

J=15.6Hz), 7.50 (2H, d, J=8.4Hz), 7.37 (2H, d, J=8.6Hz), 6.45 (1H, d, J=15.6Hz), 4.82 (1H, br), 3.46 (3H, s), 3.27 (1H, m), 3.02 (3H, s), 2.78 (1H, brd, J=12.3Hz), 2.09 (2H, d, J=6.0Hz), 2.04 (2H, brt, J=8Hz), 1.90–1.64 (3H, m), 1.60 (2H, m)

Mass m/e (FAB): 582 (MH+), 490, 324, 209, 140 (base), 112

| elemental analysis as C₂₆H₃₅N₃O₅S₂.0.4H₂O | | | |
|---|---|---|---|
| | C | H | N |
| calculated (%) | 57.73 | 6.67 | 7.77 |

-continued

| elemental analysis as $C_{26}H_{35}N_3O_5S_2 \cdot 0.4H_2O$ | | | |
|---|---|---|---|
| | C | H | N |
| found (%) | 57.50 | 6.39 | 7.54 |

EXAMPLE 11

N-(1-Methyl-4-piperidyl)-4-{N-methyl-N-[(E)-3-(4-methylsulfonylphenyl)-2-propenoyl]amino}-benzenesulfonamide

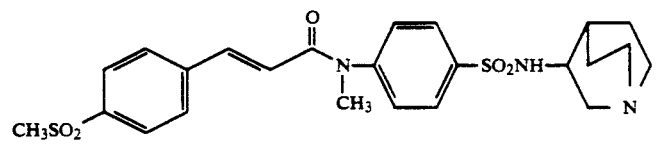

m.p. (°C.): 122~125 (AcOEt).
$^1$H-NMR (90 MHz, CDCl$_3$) δ: 7.96 (2H, d, J=8.6Hz), 7.88 (2H, d, J=8.6Hz), 7.74 (1H, d, J=15.8Hz), 7.49 (2H, d, J=8.6Hz), 7.37 (2H, d, J=8.6Hz), 6.44 (1H, d, J=15.8Hz), 3.47 (3H, s), 3.3 (1H, m), 3.03 (3H, s), 2.7 (2H, m), 2.24 (3H, s), 2.1~1.4 (6H, m).
Mass m/e (FAB): 492 (MH., base), 315, 282, 209, 170

| elemental analysis as $C_{23}H_{29}N_3O_5S_2$ | | | |
|---|---|---|---|
| | C | H | N |
| calculated (%) | 56.19 | 5.95 | 8.55 |
| found (%) | 56.13 | 6.11 | 8.17 |

EXAMPLE 12

N-(3-Quinuclidyl)-4-{N-methyl-N-[(E)-3-(4-methylsulfonylphenyl)-2-propenoyl]amino}benzenesulfonamide

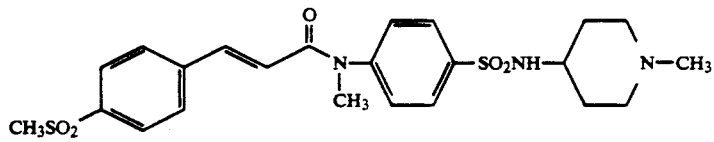

m.p. (°C.): 221~222 (EtOH-MeOH).
$^1$H-NMR (90 MHz, DMSO-d$_6$) δ: 8.46 (1H, d, J=6.5Hz, D$_2$O exchange), 8.00~7.40 (9H, m), 6.73 (1H, d, J=15.4Hz), 3.39 (3H, s), 3.21 (3H, s), 3.80-2.80 (8H, m), 2.10-1.50 (4H, m).
Mass m/e (FAB): 504 (MH+), 277, 185 (base), 125

| elemental analysis as $C_{24}H_{29}N_3O_5S_2 \cdot 2.5H_2O$ | | | |
|---|---|---|---|
| | C | H | N |
| calculated (%) | 52.53 | 6.24 | 7.66 |
| found (%) | 52.18 | 5.57 | 7.34 |

EXAMPLE 13

N-[3-(N,N-Dimethylamino)propyl]-4-{N-methyl-N-[(E)-3-(4-methylsulfonylphenyl)-2-propenoyl]-amino}benzenesulfonamide hydrochloride -continued

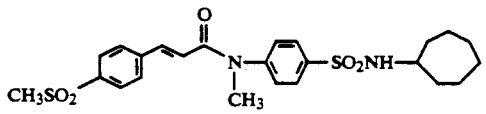

m.p. (°C.): 201~204 (MeOH)

$^1$H NMR (400 MHz, DMSO-d$_6$) δ: 7.94 (1H, t, J=6.0Hz), 7.88 (2H, d, J=7.7Hz), 7.86 (2H, d, J=8.4Hz), 7.78 (2H, d, J=7.7Hz), 7.62 (1H, d, J=15.6Hz), 7.56 (2H, d, J=8.4Hz), 6.76 (1H, brd, J=15.6Hz), 3.38 (3H, s), 3.36 (3H, s), 3.01 (2H, dd, J=7.0, 6.0Hz), 2.86 (2H, q, J=6.0Hz), 1.82 (2H, quint, J=7.7Hz).
Mass m/e (FAB): 480 (MH, base), 259, 209, 167, 149

| elemental analysis as $C_{22}H_{29}N_3O_5S_2 \cdot HCl$ | | | |
|---|---|---|---|
| | C | H | N |
| calculated (%) | 51.20 | 5.86 | 8.14 |
| found (%) | 50.86 | 5.86 | 7.99 |

EXAMPLE 14

N-Cycloheptyl-4-{N-methyl-N-[(E)-3-(4-methylsulfonylphenyl)-2-propenoyl]amino}benzenesulfonamide

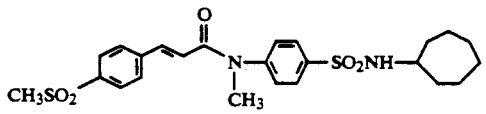

m.p. (°C.): 146~148 (MeOH).
$^1$H-NMR (90 MHz, CDCl$_3$) δ: 7.94 (1H, d, J=8.8Hz), 7.87 (2H, d, J=8.4Hz), 7.74 (1H, d, J=15.4Hz), 7.49 (2H, d, J=8.4Hz), 7.36 (2H, d, J=8.8Hz), 6.43 (1H, d, J=15.4Hz), 4.59 (1H, d, J=8.4Hz), 3.46 (3H,s), 3.46 (1H, m), 3.03 (3H, s), 2.00~1.30 (12H, m).
Mass m/e (FD): 490 (M+)

| elemental analysis as $C_{24}H_{30}N_2O_5S_2$ | | | |
|---|---|---|---|
| | C | H | N |
| calculated (%) | 58.75 | 6.16 | 5.71 |
| found (%) | 58.51 | 6.15 | 5.60 |

EXAMPLE 15

N-[2-(6-methyl-2-pyridyl)ethyl]-4-{N-methyl-N-[(E)-3-(4-methylsulfonylphenyl)-2-propenoyl]amino}benzenesulfonamide hydrochloride

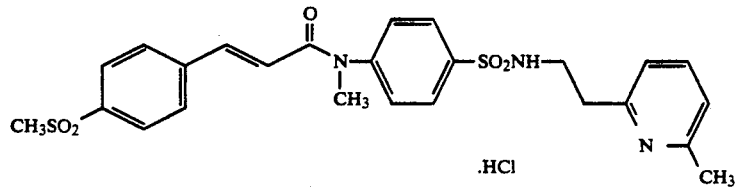

m.p. (°C.): 169~175 (AcOEt).

$^1$H-NMR (400 MHz, CMSO-$d_6$) δ: 7.94 (2H, d, J=8.6Hz), 7.83 (2H, d, J=8.2Hz), 7.72 (1H, d, J=15.6Hz), 7.48 (3H, m), 7.34 (2H, d, J=8.6Hz), 7.00 (1H, d, J=7.5Hz), 6.90 (1H, d, J=7.7Hz), 6.60 (1H, brt), 6.43 (1H, d, J=15.6Hz), 3.44 (3H, s), 3.42 (2H, m), 2.94 (2H, t, J=6.0Hz), 2.48 (3H, s), 3.02 (3H, s).

Mass m/e (FAB): 514 (MH+, base), 498, 304.

| elemental analysis as $C_{25}H_{27}N_3O_5S_2 \cdot 0.2H_2O$ | | | |
|---|---|---|---|
| | C | H | N |
| calculated (%) | 54.23 | 5.17 | 7.59 |
| found (%) | 54.07 | 5.03 | 7.42 |

EXAMPLE 16

N-[3-(4-Pyridyl)propyl]-4-{N-methyl-N-[(E)-3-(4-methylsulfonylphenyl)-2-propenoyl]amino}benzenesulfonamide

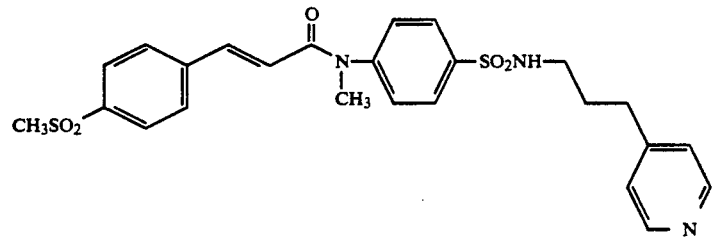

m.p. (°C.): amorphous (CH$_2$Cl$_2$).

$^1$H-NMR (400 MHz, CDCl$_3$) δ: 8.48 (2H, d, J=6.0Hz), 7.93 (2H, d, J=8.6Hz), 7.87 (2H, d, J=8.4Hz), 7.75 (1H, d, J=15.6Hz), 7.51 (2H, d, J=8.4Hz), 7.38 (2H, d, J=8.6Hz), 7.09 (2H, d, J=6.0Hz), 6.47 (1H, d, J=15.6Hz), 5.05 (1H, t, J=7Hz), 3.46 (3H, s), 3.05 (2H, m), 2.69 (2H, t, J=7.7Hz), 1.89 (2H, quint, J=7.7Hz).

Mass m/e (FAB):
High MASS: as $C_{25}H_{27}N_3O_5S_2$: calculated (%) 514.1470 (MH+) found (%) 514.1471

EXAMPLE 17

N-Methyl-N-[2-(2-pyridyl)ethyl]-4-{N-methyl-N-[(E)-3-(4-methylsulfonylphenyl)-2-propenoyl]amino}benzenesulfonamide hydrochloride

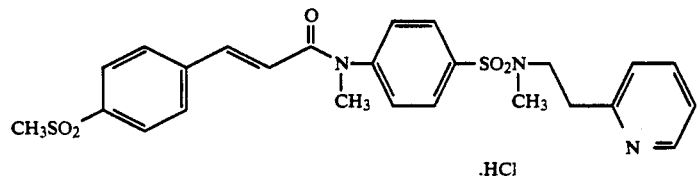

m.p (°C.): 153~159 (AcOEt).

$^1$H-NMR (400 MHz, DMSO-$d_6$) δ: 8.79 (1H, d, J=8Hz), 8.46 (1H, t, J=8Hz), 7.97 (1H, d, J=8Hz), 7.85 (3H, m), 7.76 (4H, m), 7.60 (1H, d, J=15.6Hz), 7.55 (2H, dd, J=8.2Hz), 6.74 (1H, d, J=15.6Hz), 3.46 (2H, d, J=6Hz), 3.38 (3H, s), 3.30 (2H, t, J=6Hz), 3.18 (3H, s), 2.79 (3H, s)

Mass m/e (FAB):
514 (MH+, base), 378, 314, 209, 170.

| elemental analysis as $C_{25}H_{27}N_3O_5S_2 \cdot HCl \cdot 0.1H_2O$ | | | |
|---|---|---|---|
| | C | H | N |
| calculated (%) | 54.40 | 5.33 | 7.61 |
| found (%) | 51.17 | 5.01 | 7.38 |

EXAMPLE 18

N-[2-(2-Pyridyl)ethyl]-4-{N-methyl-N-[(E)-3-(4-methylsulfonylphenyl)-2-propenoyl]amino}benzenesulfonamide -continued

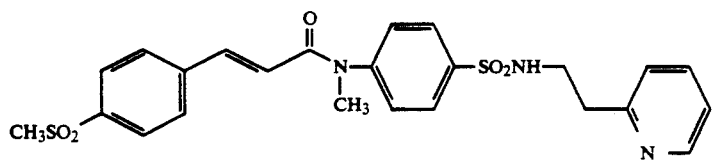

m.p. (°C.): 143~144 (Et₂O-EtOH).

¹H-NMR (90 MHz, DMSO-d₆) δ: 8.43 (1H, d like, J=6.0Hz), 7.96~7.40 (10H, m), 7.17 (1H, d like, J=7.5Hz), 6.71 (1H, d, J=15.4Hz), 3.39 (3H, s), 3.19 (3H, s), 3.30-3.00 (2H, m), 2.85 (1H, t like, J=6.6Hz).

Mass m/e (FD): 499 (M+).

elemental analysis as $C_{24}H_{25}N_3O_5S_2 \cdot 0.5H_2O$

|  | C | H | N |
|---|---|---|---|
| calculated (%) | 56.67 | 5.15 | 8.26 |
| found (%) | 56.67 | 4.93 | 8.17 |

EXAMPLE 19

N-(2-Pyridylmethyl)-4-{N-methyl-N-[(E)-3-(4-methylsulfonylphenyl)-2-propenoyl]amino}benzenesulfonamide hydrochloride

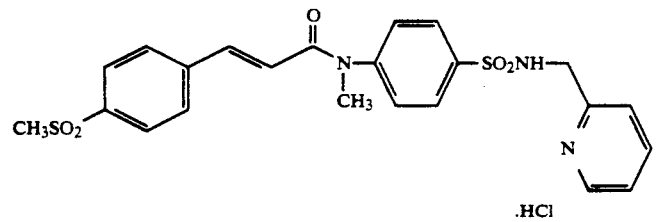

m.p. (°C.): 125~128 (CH₂Cl₂-EtOH-MeOH).

¹H-NMR (90 MHz, DMSO-d₆) δ: 8.78 (1H, d D₂O exchange), 8.68 (1H, d, J=5.0Hz), 8.34 (1H, t, J=8.0Hz), 8.00-7.45 (11H, m), 6.74 (1H, d, J=15.8Hz), 4.45 (2H, s), 3.39 (3H, s), 3.20 (3H, s).

Mass m/e (FAB): 486 (MH+), 314, 278, 209, 170, 131, 107 (base).

elemental analysis as $C_{23}H_{23}N_3O_5S_2 \cdot HCl$

|  | C | H | N |
|---|---|---|---|
| calculated (%) | 52.92 | 4.63 | 8.05 |
| found (%) | 52.85 | 4.57 | 7.70 |

EXAMPLE 20

(E)-N-Methyl-N-[4-(4-cyclohexylmethyl-1-homopiperazinyl)sulfonylphenyl]-3-(4-methylsulfonylphenyl)-2-propenamide hydrochloride

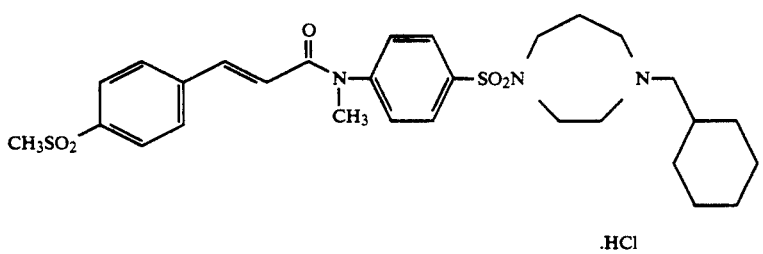

m.p. (°C.): 212~216 (AcOEt-MeOH-EtOH)

¹H-NMR (400 MHz, CDCl₃) δ: 11.95 (1H, brs), 7.91 (2H, d, J=8.2Hz), 7.82 (2H, d, J=8.2Hz), 7.75 (1H, d, J=15.5Hz), 7.54 (2H, d, J=8.2Hz), 7.41 (2H, d, J=8.2Hz), 6.48 (1H, d, J=15.5Hz), 3.95-3.55 (5H, m), 3.48 (3H, s), 3.30~2.85 (6H, m), 3.05 (3H, s), 2.20 (1H, m), 2 05~1.65 (6H, m), 1.35~1.00 (5H, m).

Mass m/e (FAB): 574 (MH+), 394, 364, 195 (base).

elemental analysis as $C_{29}H_{39}N_3O_5S_2 \cdot HCl \cdot 0.3H_2O$

|  | C | H | N |
|---|---|---|---|
| calculated (%) | 56.58 | 6.65 | 6.83 |
| found (%) | 56.60 | 6.48 | 6.69 |

EXAMPLE 21

(E)-N-Methyl-N-[4-(4-benzyl-1-homopiperazinyl)-sulfonylphenyl]-3-(4-methylsulfonylphenyl)-2-propenamide hydrochloride -continued

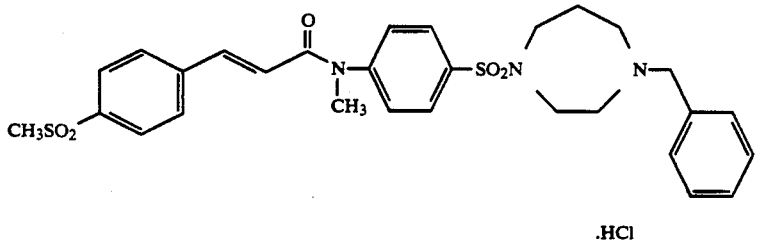
.HCl m.p (°C.): 196~199 (AcOEt)
¹H-NMR (400 MHz, CDCl₃-DMSO-d₆) δ: 11.95 (1H, brs), 7.91 (2H, d, J=8.4Hz), 7.82 (2H, d, J=8.9Hz), 7.73 (1H, d, J=15.6Hz), 7.70 (2H, m), 7.58 (2H, d, J=8.9Hz), 7.45 (2H, d, J=8.4Hz), 7.45 (3H, m), 6.54 (1H, d, J=15.6Hz), 4.38 (1H, m), 4.28 (1H, m), 3.91 (1H, m), 3.73 (1H, m), 3.57 (2H, m), 3.48 (3H, s), 3.33~3.11 (3H, m), 3.08 (3H, s), 2.75 (1H, m), 2.17 (1H, m).

Mass m/e (FAB): 568 (MH+), 359, 315, 209, 189 (base)

| elemental analysis as C₂₉H₃₃N₃O₅S₂.HCl | | | |
|---|---|---|---|
| | C | H | N |
| calculated (%) | 57.65 | 5.67 | 6.96 |
| found (%) | 57.36 | 5.77 | 6.61 |

EXAMPLE 22

(E)-N-Methyl-N-{4-{4-(2-phenylethyl)piperazinyl]-sulfonylphenyl}-3-(4-methylsulfonylphenyl)-2-propenamide

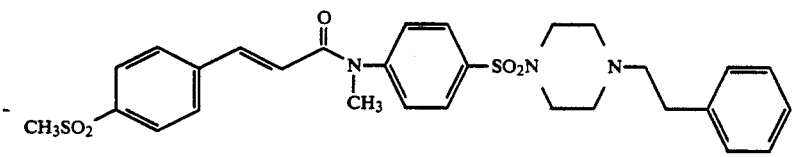

m.p. (°C.): 193~194 (AcOEt)
¹H-NMR (400 MHz, CDCl₃) δ: 7.90 (2H, d, J=8.3Hz), 7.86 (2H, d, J=8.6Hz), 7.77 (1H, d, J=15.6Hz), 7.54 (2H, d, J=8.3Hz), 7.42 (2H, d, J=8.6Hz), 7.28 (2H, m), 7.21 (1H, d, J=6.2Hz), 7.17 (2H, d, J=6.8Hz), 6.48 (1H, d, J=15.6Hz), 3.48 (1H, s), 3.14 (3H, s), 3.04 (3H, s), 2.77 (2H, m), 2.66 (4H, m).

Mass m/e (FAB): 568 (MH+), 476, 209, 136 (base).
elemental analysis as C₂₉H₃₃N₃O₅S₂.

| elemental analysis as C₂₉H₃₃N₃O₅S₂ | | | |
|---|---|---|---|
| | C | H | N |
| calculated (%) | 61.35 | 5.86 | 7.40 |
| found (%) | 61.36 | 5.87 | 7.21 |

EXAMPLE 23

(E)-N-Methyl-N-{4-[4-(3-pyridylmethyl)piperazinyl]sulfonylphenyl}-3-(4-methylsulfonylphenyl)-2-propenamide

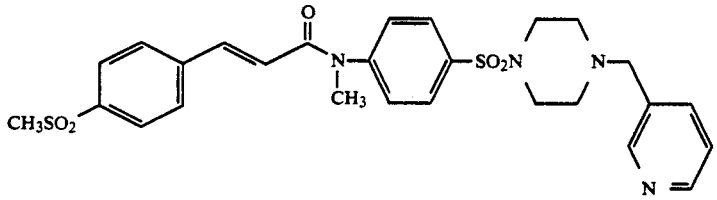

m.p. (°C.): 194~196 (CH₂Cl₂-EtOH isoPr₂O).
¹H-NMR (400 MHz, CDCl₃) δ: 8.50 (2H, s), 7.88 (2H, d, J=8.2Hz), 7.82 (2H, d, J=8.4Hz), 7.73 (1H, d, J=15.4Hz), 7.56 (1H, brd, J=7.7Hz), 7.51 (2H, d, J=8.2Hz), 7.39 (2H, d, J=8.4Hz), 7.23 (1H, dd, J=7.7, 4.8Hz), 6.45 (1H, d, J=15.4Hz), 3.53 (2H, s), 3.46 (3H, s), 3.09 (4H, brs), 3.02 (3H, s), 2.57 (4H, t, J=4.6Hz).

Mass m/e (FAB): 555 (MH+), 347, 209, 176 (base).

| elemental analysis as C₂₇H₃₀N₄O₅S₂ | | | |
|---|---|---|---|
| | C | H | N |
| calculated (%) | 58.46 | 5.45 | 10.10 |
| found (%) | 58.17 | 5.37 | 9.95 |

EXAMPLE 24

(E)-N-methyl-N-[4-(4-benzylpiperazinyl)sulfonylphenyl]-3-(4-methylsulfonylphenyl)-2-propenamide hydrochloride

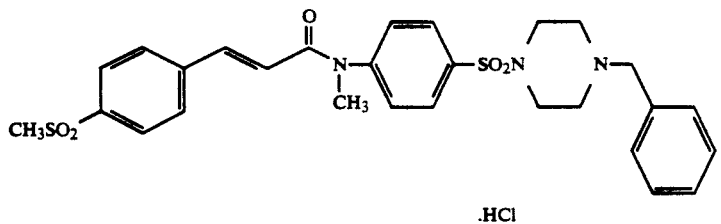

m.p. (°C.): 194~196 (CH₂Cl₂).

¹H-NMR (400 MHz, DMSO-d₆) δ: 7.89 (4H, s), 7.80 (2H, d, J=7.2Hz), 7.65 (1H, d, J=15.6Hz), 7.63 (2H, d, J=7.2Hz), 7.60 (2H, m), 7.43 (3H, m), 6.76 (1H, brd, J=15.6Hz), 4.30 (2H, brs), 3.74 (2H, brs), 3.39 (3H, s), 3.3 (4H), 3.19 (3H, s), 2.95 (2H, brs).

Mass m/e (FAB): 554 (MH.), 346, 259, 207, 149, 115 (base).

| elemental analysis as C₂₄H₂₇N₃O₃S | | | |
|---|---|---|---|
| | C | H | N |
| calculated (%) | 65.88 | 6.22 | 9.60 |
| found (%) | 65.83 | 6.17 | 9.41 |

EXAMPLE 26

N-(1-Benzyl-4-piperidyl)-4-{N-methyl-N-[(E)-3-(4-cyanophenyl)-2-propenoyl]-amino}benzenesulfonamide hydrochloride

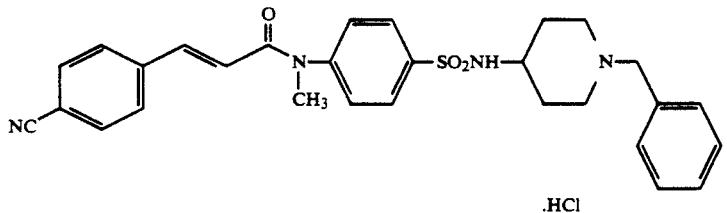

m.p. (°C.): 180~183 (AcOEt)

¹H-NMR (90 MHz, DMSO-d₆) δ: 8.12 (1H, d, J=7.0Hz, D₂O exchange), 8.00~7.32 (14H, m), 6.67 (1H, d, J=15.9Hz), 4.20 (2H, m, D₂O exchange), 3.40 (3H, s), 3.60~2.60 (5H, m), 2.20~1.60 (4H, m).

Mass m/e (FD):

| elemental analysis as C₂₈H₃₁N₃O₅S₂.HCl.0.5H₂O | | | |
|---|---|---|---|
| | C | H | N |
| calculated (%) | 56.13 | 5.55 | 7.01 |
| found (%) | 55.85 | 5.48 | 6.99 |

EXAMPLE 25

N-Cycloheptyl-4-{N-methyl-N-I(E)-3-(4-cyanophenyl)-2-propenoyl]amino}benzenesulfonamide

| elemental analysis as C₂₉H₃₀N₄O₃S.HCl.0.7H₂O | | | |
|---|---|---|---|
| | C | H | N |
| calculated (%) | 61.79 | 5.75 | 9.93 |
| found (%) | 61.84 | 5.59 | 9.95 |

EXAMPLE 27

N-(2-Indanyl)-4-{N-methyl-N-[(E)-3-(4-(1-imidazoyl)phenyl]-2-propenoyl]amino}-benzenesulfonamide

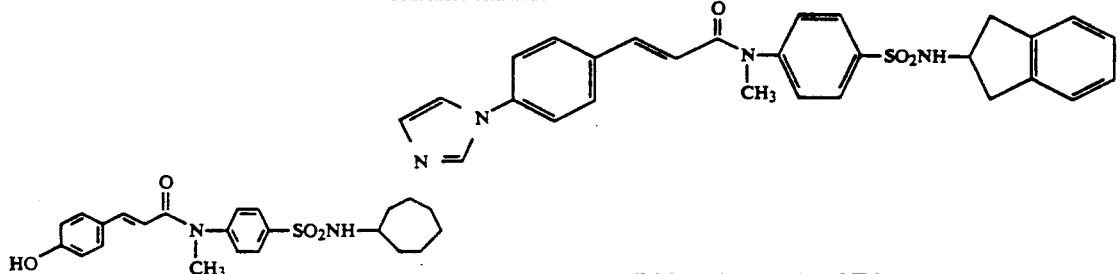

m.p. (°C.): 170~171 (Et₂O-AcOEt).

¹H-NMR (90 MHz, CDCl₃) δ: 8.00~7.40 (10H, m), 6.63 (1H, d, J=15.8Hz), 3.40 (3H, s), 3.20 (1H, m), 1.80~1.00 (12H, m).

Mass m/e (FAB): 438 (MH⁺, base), 342, 262, 156, 136.

m.p. (°C.): 213~215 (AcOEt).

¹H-NMR (90 MHz, DMSO-d₆) δ: 8.25 (1H, s), 8.20 (1H, d, J=7.5Hz, D₂O exchange), 8.04 (2H, d, J=9.2Hz), 7.80~7.40 (3H, m), 7.61 (4H, s), 7.09 (4H, s), 6.60 (1H, d, J=15.4Hz), 3.92 (1H, m), 3.40 (3H, s), 3.20~2.57 (4H, m).

Mass m/e (FD) 498 (M⁺).

| elemental analysis as $C_{28}H_{26}N_4O_3S$ | | | |
|---|---|---|---|
| | C | H | N |
| calculated (%) | 67.45 | 5.26 | 11.24 |
| found (%) | 67.19 | 5.20 | 11.17 |

EXAMPLE 28

N-[1-(1,2,3,4-Tetrahydro)naphthyl]-4-{N-methyl-N-[(E)-3-(4-(1-imidazolyl)-phenyl)-2-propenoyl]amino}benzenesulfonamide m.p. (°C.): 221~222 (AcOEt)
$^1$H-NMR (90 MHz, DMSO-d$_6$) δ: 8.28 (1H, s), 8.16 (1H, d, J=7.9Hz), 7.96 (2H, d, J=8.3Hz), 7.79 7.43 (4H, m), 7.61 (4H, s), 7.08 (4H, s), 7.08 (1H, s), 6.55 (1H, d, J=15.8Hz), 4.43 (1H, m), 3.39 (3H, s), 2.65 (2H, m), 1.65 (4H, m).
Mass m/e (FD): 512 (M+)

| elemental analysis as $C_{29}H_{28}N_4O_3S \cdot 0.1H_2O$ | | | |
|---|---|---|---|
| | C | H | N |
| calculated (%) | 67.71 | 5.52 | 10.89 |
| found (%) | 67.95 | 5.42 | 10.81 |

EXAMPLE 29

N-Cycloheptyl-4-{N-methyl-N-I(E)-3-(4-(1-imidazolyl)phenyl]-2-propenoyl]-amino}benzenesulfonamide m.p. (°C.): 173~174 (AcOEt-Et$_2$O).
$^1$H-NMR (90 MHz, DMSO-d$_6$) δ: 8.29 (1H, brs), 7.87 (2H, d, J=8.4Hz), 7.83~7.40 (11H, m), 7.11 (1H, brs), 6.52 (1H, d, J=15.4Hz), 3.37 (3H, s), 3.16 (1H, m), 1.88~1.05 (12H, m).
Mass m/e (FAB): 479 (MH+, base), 383, 303, 197, 170, 144.

| elemental analysis as $C_{26}H_{30}N_4O_3S$ | | | |
|---|---|---|---|
| | C | H | N |
| calculated (%) | 65.25 | 6.32 | 11.71 |
| found (%) | 65.13 | 6.45 | 11.54 |

EXAMPLE 30

N-Cyclooctyl-4-{N-methyl-N-[(E)-3-(4-(1-imidazolyl)phenyl]-2-propenoyl]-amino}benzenesulfonamide m.p. (°C.): 173~174 (AcOEt-Et$_2$O).
$^1$H-NMR (90 MHz, DMSO-d$_6$) δ: 8.29 (1H, brs), 7.87 (2H, d, J=8.4Hz), 7.83~7.40 (11H, m), 7.11 (1H, brs), 6.52 (1H, d, J=15.4Hz), 3.37 (3H, s), 3.16 (1H, m), 1.88~1.05 (12H, m).
Mass m/e (FAB): 479 (MH+, base), 383, 303, 197i 170, 144.

| elemental analysis as $C_{26}H_{30}N_4O_3S$ | | | |
|---|---|---|---|
| | C | H | N |
| calculated (%) | 65.25 | 6.32 | 11.71 |
| found (%) | 65.13 | 6.45 | 11.54 |

EXAMPLE 31

(±)-N-(exo-2-Norbornyl)-4-{N-methyl-N-[(E)-3-(4-(1-imidazolyl)phenyl]-2-propenoyl]amino}benzenesulfonamide

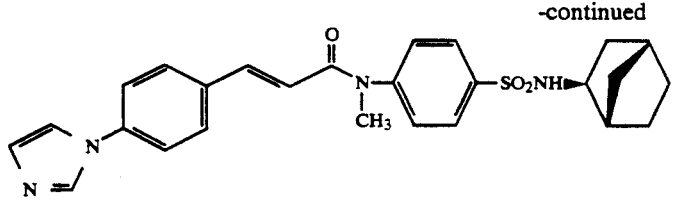

m.p (°C.): 187~188 (AcOEt-E₁2O)
¹H-NMR (90 MHz, DMSO-d₆) δ: 8.28 (1H, s), 7.86 (2H, d, J=8.8Hz), 7.74 (1H, s), 7.69~7.40 (4H, m), 7.61 (4H, s), 7.10 (1H, s), 6.53 (1H, d, J=15.8Hz), 3.37 (1H, s), 3.00 (1H, m), 2.20~1.90 (2H, m), 1.64~0.80 (8H, m).
Mass m/e (FD): 477 (MH⁺).

| elemental analysis as C₂₆H₂₈N₄O₃S.0.7H₂O | | | |
|---|---|---|---|
| | C | H | N |
| calculated (%) | 63.83 | 6.06 | 11.45 |
| found (%) | 63.83 | 5.77 | 11.46 |

EXAMPLE 32

(±)-N-(endo-2-Norbornyl)-4-{N-methyl-N-[(E)-3-(4-(1-imidazolyl)phenyl]-2-propenoyl]amino}benzenesulfonamide hydrochloride

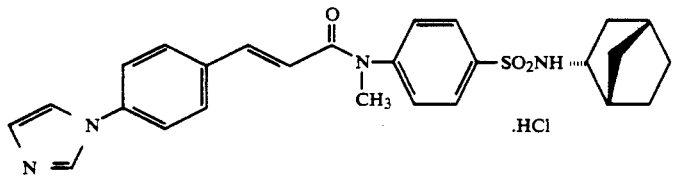

m.p. (°C.): 191~195 (AcOEt-EtOH).
¹H-NMR (90 MHz, DMSO-d₆) δ: 9.71 (1H, s), 8.27 (1H, s), 8.00~7.40 (11H, m), 6.61 (1H, d, J=15.8Hz), 3.38 (1H, s), 2.03 (2H, m), 2.00~0.70 (8H, m).
Mass m/e (FAB): 477 (MH⁺, base), 303, 197, 144, 115.

| elemental analysis as C₂₆H₂₈N₄O₃S.HCl.0.1H₂O | | | |
|---|---|---|---|
| | C | H | N |
| calculated (%) | 63.83 | 6.06 | 11.45 |
| found (%) | 63.83 | 5.77 | 11.46 |

EXAMPLE 33

N-(2-Indanyl)-4-{N-methyl-N-[(E)-3-(4-nitrophenyl)-2-propenoyl]amino}benzenesulfonamide

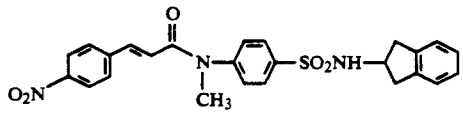

m.p. (°C.): 241~242 (AcOEt-iso-Pr₂O).
¹H-NMR (90 MHz, DMSO-d₆) δ: 8.14 (2H, d, J=8.8Hz), 8.1 (1H), 7.93 (2H, d, J=8.8Hz), 7.76 (2H, d, J=8.8Hz), 7.66 (1H, d, J=15.6Hz), 7.58 (2H, d, J=8.8Hz), 7.10 (4H, s), 6.76 (1H, d, J=15.6Hz), 3.99 (1H, m), 3.41 (3H, s), 2.99 (2H, dd, J=15.8, 7.5Hz), 2.70 (2H, dd, J=15.8, 7.5Hz).
Mass m/e (FD): 477 (MH⁺).
elemental analysis as C₂₅H₂₃N₃O₅S

| elemental analysis as C₂₅H₂₃N₃O₅S | | | |
|---|---|---|---|
| | C | H | N |
| calculated (%) | 62.88 | 4.86 | 8.80 |
| found (%) | 62.75 | 4.91 | 8.52 |

EXAMPLE 34

N-Cyclohexyl-N-methyl-4-{N-[(E)-3-(4-nitrophenyl)-2-propenoyl]amino}benzenesulfonamide

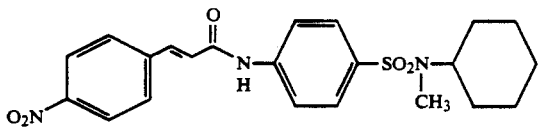

m.p. (°C.): 247~250 (AcOEt)
¹H-NMR (90 MHz, DMSO-d₆) δ: 10.70 (1H, s), 8.30 (2H, d, J=8.8Hz), 7.91 (2H, d, J=8.8Hz), 7.91 (2H, d, J=8.8Hz), 7.76 (2H, d, J=8.8Hz), 7.75 (1H, d, J=15.8Hz), 7.00 (1H, d, J=15.8Hz), 3.6 (1H, m), 2.67 (3H, s), 1.8~1.0 (10H, m).
Mass m/e (FD): 443 (MH⁺).
elemental analysis as C₂₂H₂₅N₃O₅S.0.25H₂O

| elemental analysis as C₂₂H₂₅N₃O₅S.0.25H₂O | | | |
|---|---|---|---|
| | C | H | N |
| calculated (%) | 58.97 | 5.74 | 9.38 |
| found (%) | 59.11 | 5.75 | 9.19 |

EXAMPLE 35

N-Cyclohexyl-4-{N-[(E)-3-(4-nitrophenyl)-2-propenoyl]amino}-benzenesulfonamide

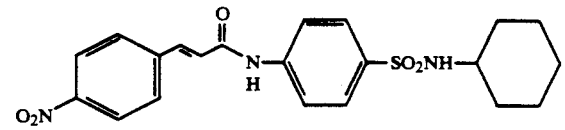

m.p. (°C.): 261~262 (AcOEt-H₂O).
¹H-NMR (90 MHz, DMSO-d₆) δ: 10.63 (1H, brs), 8.26 (2H, d, J=8.8Hz), 7.86 (2H, d, J=8.8Hz), 7.72 (2H, d, J=8.8Hz), 7.71 (1H, d, J=16.2Hz), 7.49 (1H, d, J=7.9Hz, D₂O exchange), 6.98 (1H, d, J=16.2Hz), 2.90 (1H, m), 1.8~1.0 (10H, m).

Mass m/e (FD): 429 (MH+).

| elemental analysis as C₂₁H₂₃N₃O₅S | | | |
|---|---|---|---|
| | C | H | N |
| calculated (%) | 58.73 | 5.40 | 9.78 |
| found (%) | 58.45 | 5.45 | 9.49 |

EXAMPLE 36

N-Cyclohexyl-4-{N-methyl-N-[(E)-3-(4-nitrophenyl)-2-propenoyl]amino}benzenesulfonamide

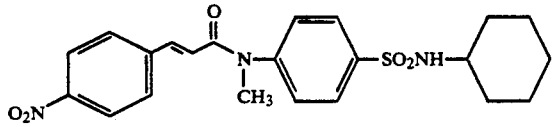

¹H-NMR (90 MHz, DMSO-d₆) δ: 8.17 (2H, d, J=8.8Hz), 7.88 (2H, d, J=8.8Hz), 7.73 (2H, d, J=8.8Hz), 7.65 (1H, d, J=16.1Hz), 7.55 (2H, d, J=8.8Hz), 6.70 (1H, d, J=16.1Hz), 3.38 (3H, s), 2.96 (1H, m), 1.8~1.0 (10H, m).

Mass m/e (FD): 443 (MH+)

| elemental analysis as C₂₂H₂₅N₃O₅S | | | |
|---|---|---|---|
| | C | H | N |
| calculated (%) | 59.58 | 5.68 | 9.48 |
| found (%) | 59.58 | 5.64 | 9.36 |

EXAMPLE 37

N-Cyclohexyl-N-methyl-4-{N-methyl-N-[(E)-3-(4-nitrophenyl)-2-propenoyl]amino}benzenesulfonamide

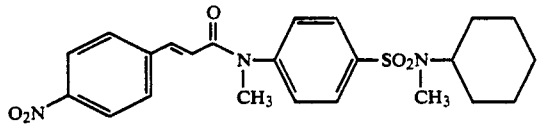

m.p. (°C.): 124~125 (AcOEt-iso-Pr₂O).

¹H-NMR (90 MHz, DMSO-d₆) δ: 8.18 (2H, d, J=8.8Hz), 7.87 (2H, d, J=8.8Hz), 7.74 (2H, d, J=8.8Hz), 7.64 (1H, d, J=15.8Hz), 7.56 (2H, d, J=8.8Hz), 6.70 (1H, d, J=15.8 Hz), 3.64 (1H, m), 3.39 (1H, s), 2.72 (3H, s), 1.8~1.0 (10H, m).

Mass m/e (FD): 457 (MH+).

| elemental analysis as C₂₃H₂₇N₃O₅S | | | |
|---|---|---|---|
| | C | H | N |
| calculated (%) | 60.38 | 5.95 | 9.18 |
| found (%) | 60.33 | 5.89 | 8.93 |

EXAMPLE 38

N-cycloheptyl-4-{N-methyl-N-[(E)-3-(4-nitrophenyl)-2-propenoyl]amino}benzenesulfonamide

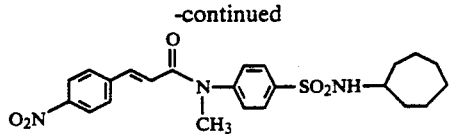

m.p. (°C.): 187~188 (AcOEt-iso-Pr₂O).

¹H-NMR (90 MHz, DMSO-d₆) δ: 8.19 (2H, d, J=8.6Hz), 7.96 (2H, d, J=8.6Hz), 7.75 (1H, d, J=15.4Hz), 7.46 (2H, d, J=8.6Hz), 7.37 (2H, d, J=8.6Hz), 6.44 (1H, d, J=15.4Hz), 4.51 (1H, brd, J=7.9Hz), 3.47 (3H, s), 3.4 (1H, m), 2.0~1.2 (12H, m).

Mass m/e (FD): 457 (MH+).

| elemental analysis as C₂₃H₂₇N₃O₅S | | | |
|---|---|---|---|
| | C | H | N |
| calculated (%) | 60.38 | 5.95 | 9.18 |
| found (%) | 60.33 | 5.96 | 9.02 |

EXAMPLE 39

N-Cycloheptyl-4-{N-methyl-N-[(2E,4E)-5-(4-nitrophenyl)-2,4-pentadienoyl]amino}benzenesulfonamide

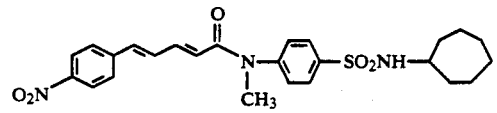

m.p. (°C.): 208~210 (AcOEt-iso Pr₂O).

¹H-NMR (90 MHz, DMSO-d₆) δ: 8.13 (2H, d, J=8.8Hz), 7.84 (2H, d, J=8.8Hz), 7.71 (2H, d, J=8.8Hz), 7.67 (2H, d, J=7.2 Hz, D₂O exchange), 7.49 (2H, d, J=8.8Hz), 7.4~7.0 (3H, m), 6.13 (1H, m), 3.33 (1H, m), 3.22 (3H, m), 2.0~1.2 (12H, m).

Mass m/e (FD): 483 (MH+)

| elemental analysis as C₂₅H₂₉N₃O₅S | | | |
|---|---|---|---|
| | C | H | N |
| calculated (%) | 62.09 | 6.05 | 8.69 |
| found (%) | 62.03 | 6.02 | 8.68 |

EXAMPLE 40

N-(2-Indanyl-4-{N-methyl-N-[(E)-3-(3,5-dihydroxyphenyl)-2-propenoyl]amino}benzenesulfonamide

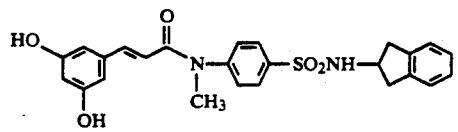

m.p. (°C.): 243~244 (AcOEt).

¹H-NMR (90 MHz, DMSO-d₆) δ: 9.36 (2H, s), 8.13 (1H, d, J=6.6Hz), 7.93 (2H, d, J=8.4Hz), 7.57 (2H, d, J=8.4Hz), 7.36 (1H, d, J=15.8Hz), 7.11 (4H, s), 6.33 (1H, d, J=15.8Hz), 6.27 (3H, brs), 3.33 (3H, s), 3.02 (2H, dd, J=16.0, 7.5Hz), 2.73 (2H, dd, J=16.0Hz).

Mass m/e (FD): 464 (MH+).

| elemental analysis as $C_{25}H_{24}N_2O_5S \cdot 0.6H_2O$ | | | |
|---|---|---|---|
| | C | H | N |
| calculated (%) | 63.17 | 5.34 | 5.89 |
| found (%) | 63.15 | 5.67 | 4.93 |

EXAMPLE 41

N-(2-Indanyl)-4-{N-methyl-N-[(E)-3-(4-hydroxyphenyl)-2-propenoyl]amino}benzenesulfonamide

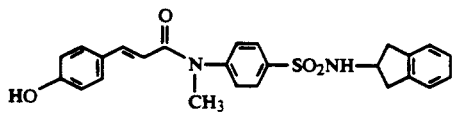

m.p. (°C.): 215~217 (iso Pr₂O-Et₂O).

$^1$H-NMR (90 MHz, DMSO-$d_6$) δ: 9.88 (1H, s, D₂O exchange), 8.08 (1H, d, J=7.0Hz, D₂O exchange), 7.91 (2H, d, J=8.8Hz), 7.5 (2H, d, J=8.8Hz), 7.48 (1H, d, J=15.4Hz), 7.29 (2H, d, J=8.8Hz), 7.11 (4H, s), 6.69 (2H, d, J=8.4 Hz), 6.31 (1H, d, J=15.4Hz), 3.94 (1H, m), 3.36 (3H, s), 3.16~2.52 (4H, m).

Mass m/e (FD): 449 (MH+).

| elemental analysis as $C_{25}H_{24}N_2O_4S$ | | | |
|---|---|---|---|
| | C | H | N |
| calculated (%) | 66.96 | 5.39 | 6.25 |
| found (%) | 66.63 | 5.23 | 6.04 |

EXAMPLE 42

Disodium salt of 4-{(E)-1-[N-methyl-N-[4-(2-indanyl)aminosulfonylphenyl]amino]-3-propenoyl}phenoxyacetic acid

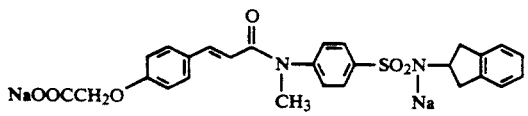

m.p. (°C.): 223~237 (EtOH-H₂O).

$^1$H-NMR (90 MHz, DMSO-$d_6$) δ: 7.74 (2H, d, J=8.8Hz), 7.45 (1H, d, J=15.4Hz), 7.24 (4H, ABq), 7.02 (4H, m), 6.73 (2H, d, J=8.3Hz), 6.22 (1H, d, J=15.4Hz), 4.13 (2H, s), 3.29 (3H, s), 3.72 (1H, m), 2.96-2.35 (4H, m).

Mass m/e (FAB): 551 (MNa+, base), 529 (MH+), 207, 137, 115.

| elemental analysis as $C_{27}H_{24}N_2O_6Na_2 \cdot 4.1H_2O$ | | | |
|---|---|---|---|
| | C | H | N |
| calculated (%) | 51.94 | 5.20 | 4.49 |
| found (%) | 51.58 | 4.90 | 4.40 |

EXAMPLE 43

N-Cycloheptyl-4-{N-methyl-N-[(E)-3-(3-fluoro-4-hydroxyphenyl)-2-propenoyl]amino}benzenesulfonamide

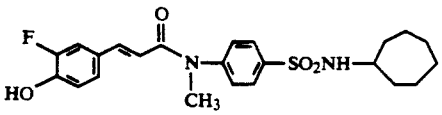

m.p. (°C.): 190~191 (AcOEt-iso Pr₂O).

$^1$H-NMR (90 MHz, DMSO-$d_6$) δ: 7.87 (2H, d, J=8.4Hz), 7.68 (1H, d, J=7.9Hz), 7.52 (2H, d, J=8.4Hz), 6.96 (1H, d, J=15.6Hz), 7.5-6.7 (3H, m), 6.28 (1H, d, J=15.6Hz), 3.34 (3H, s), 3.2 (3H, m), 1.8~1.1 (12H, m).

Mass m/e (FD): 446 (M+).

| elemental analysis as $C_{23}H_{27}FN_2O_4S$ | | | |
|---|---|---|---|
| | C | H | N |
| calculated (%) | 61.86 | 6.10 | 6.27 |
| found (%) | 61.73 | 6.04 | 6.13 |

EXAMPLE 44

N-Cycloheptyl-4-{N-methyl-N-[(2E;4E)-5-(3,5-dibromo-4-hydroxyphenyl)-2,4-pentadienoyl]-amino}benzenesulfonamide

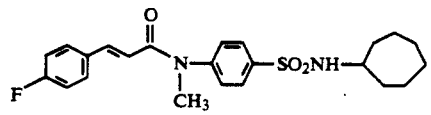

m.p. (°C.): 201~202 (EtOH).

$^1$H-NMR (90 MHz, DMSO-$d_6$) δ: 7.87 (2H, d, J=8.3Hz), 7.70 (2H, s), 7.69 (1H, d, J=7.5Hz), 7.51 (2H, d, J=8.3Hz), 7.40~7.00 (2H, m), 7.00~6.80 (2H, m), 5.97 (1H, d, J=14.1Hz), 3.30 (3H, s), 1.80~1.00 (12H, m)

Mass m/e (FAB): 613 (MH+), 331, 307, 289, 154 (base).

| elemental analysis as $C_{25}H_{28}Br_2N_2O_4S$ | | | |
|---|---|---|---|
| | C | H | N |
| calculated (%) | 49.03 | 4.61 | 4.57 |
| found (%) | 48.79 | 4.40 | 4.53 |

EXAMPLE 45

N-Cycloheptyl-4-{N-methyl-N-[(E)-3-(4-fluorophenyl-2-propenoyl)amino}benzenesulfonamide

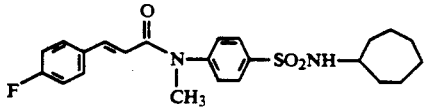

m.p. (°C.): 168~169 (AcOEt-isoPr₂O).

$^1$H NMR (90 MHz, CDCl₃) δ: 7.94 (2H, d, J=8.6Hz), 7.68 (1H, d, J=15.6Hz), 7.36 (2H, d, J=8.6Hz), 7.31 (2H, dd, J=8.8, 5.3Hz), 6.98 (2H, t, J=8.8Hz), 6.24 (1H, d, J=15.6Hz), 4.61 (1H, d, J=8.4Hz), 3.44 (3H, s), 3.44 (1H), 2.0~1.3 (12H, m).

Mass m/e (FD): 430 (M+).

| elemental analysis as $C_{23}H_{27}FN_2O_3S$ | | | |
|---|---|---|---|
| | C | H | N |
| calculated (%) | 64.16 | 6.32 | 6.51 |
| found (%) | 64.15 | 6.28 | 6.40 |

EXAMPLE 46

N-(2-Indanyl-4-{N-methyl-N-[(2E,4E)-5-(3,4-dihydroxyphenyl)-2,4-pentadienoyl]amino}benzenesulfonamide

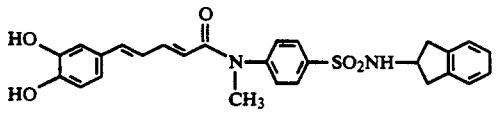

m.p. (°C.): 194~197 (AcOEt-isoPr2O).

$^1$H-NMR (90 MHz, DMSO-d$_6$) δ: 8.11 (1H, d, J=6.6Hz, D$_2$O exchange), 7.90 (2H, d, J=8.8Hz), 7.52 (2H, d, J=8.8Hz), 7.11 (4H,s), 6.87~6.50 (4H, m), 5.98 (1H, d, J=15.4Hz), 3.32 (3H, s), 3.20~2.52 (4H, m).

Mass m/e (FD): 491 (MH+).

| elemental analysis as $C_{27}H_{26}N_2O_5S$ | | | |
|---|---|---|---|
| | C | H | N |
| calculated (%) | 64.52 | 5.48 | 5.57 |
| found (%) | 64.52 | 5.53 | 5.58 |

EXAMPLE 47

N-[2-(1,2,3,4-Tetrahydro)naphthyl]-4-{N-methyl-N-[(E)-3-(3,4-dihydroxyphenyl)-2-propenoyl]amino}-benzenesulfonamide

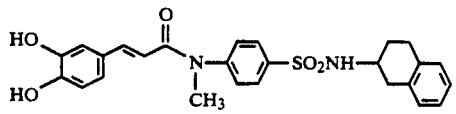

m.p. (°C.): 277~280 (isoPr2O-Etzo)

$^1$H-H-NMR (90 MHz, DMSO-d$_6$) δ: 9.20 (1H, br, D$_2$O exchange), 7.92 (2H, d, J=8.3Hz), 7.90 (1H, br, D$_2$O, exchange), 7.53 (2H, d, J=8.3Hz), 7.39 (1H, d, J=15.8Hz), 7.10~6.80 (4H, m), 6.80~6.52 (3H, m), 6.19 (1H, d, J=15.8Hz), 2.72 (4H, m), 2.00~1.60 (2H, m).

3 Mass m/e (FD): 479 (MH+).

| elemental analysis as $C_{26}H_{26}N_2O_5S$ | | | |
|---|---|---|---|
| | C | H | N |
| calculated (%) | 65.25 | 5.48 | 5.85 |
| found (%) | 65.20 | 5.51 | 5.64 |

EXAMPLE 48

N-[2-(1,2,3,4-Tetrahydro)naphthyl]-4-{N-methyl-N-[(2E,4E)-5-(3,4-dihydroxyphenyl)-2,4-pentadienoyl]-amino}benzenesulfonamide

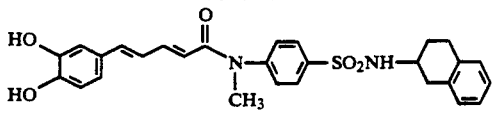

m.p. (°C.): 190~194 (isoPr2O-Et2O).

$^1$H-NMR (90 MHz, DMSO-d$_6$) δ: 7.91 (2H, d, J=8.4Hz), 7.90 (1H, d, D$_2$O exchange), 7.51 (2H, d, J=8.8Hz), 7.37~6.59( 10H, m), 5.96 (1H, d, J=14.5Hz), 3.32 (3H, s), 2.72 (4H, m), 1.77 (2H, m).

Mass m/e (FAB): 505 (MH+), 189, 131 (base).

| elemental analysis as $C_{28}H_{27}N_2O_5S \cdot 0.5H_2O$ | | | |
|---|---|---|---|
| | C | H | N |
| calculated (%) | 65.48 | 5.69 | 5.45 |
| found (%) | 65.37 | 5.88 | 5.25 |

EXAMPLE 49

N-Cycloheptyl-4-{N-methyl-N-[(E)-3-(3,4-dihydroxyphenyl)-2-propenoyl]amino}benzenesulfonamide

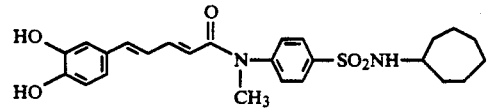

m.p. (°C.): 207~210 (AcOEt-Et2O).

$^1$H-NMR (90 MHz, DMSO-d$_6$) δ: 7.86 (2H, d, J=8.4Hz), 7.51 (2H, d, J=8.8Hz), 7.37 (2H, d, J=15.4Hz), 6.82~6.59 (3H, m), 6.13 (1H, d, J=15.4Hz), 3.32 (3H, s), 1.90~1.00 (12H, m).

Mass m/e (FD): 444 (M+).

| elemental analysis as $C_{23}H_{28}N_2O_5S$ | | | |
|---|---|---|---|
| | C | H | N |
| calculated (%) | 62.14 | 6.35 | 6.30 |
| found (%) | 61.99 | 6.27 | 6.17 |

EXAMPLE 50

N-Cycloheptyl-4-{N-methyl-N-[(2E,4E)-5-(3,4-dihydroxyphenyl)-2,4-pentadienoyl]amino}-benzenesulfonamide

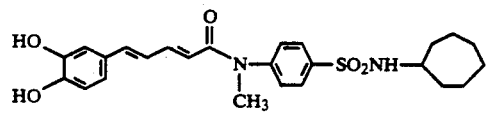

m.p (°C.): 213~215 (AcOEt-Et2O).

$^1$H-NMR (90 MHz, DMSO-d$_6$) δ: 9.30, 8.36 (each 1H, s, D$_2$O exchange), 7.85 (2H, d, J=8.4Hz), 7.68 (1H, d, J=7.4Hz, D$_2$O exchange), 7.49 (2H, d, J=8.8Hz), 7.33-6.39 (6H, m), 5.89 (1H, d, J=14.1Hz), 3.29 (3H, s), 3.20 (1H, m), 1.44 (12H, m).

Mass m/e (FD): 470 (M+).

| elemental analysis as $C_{25}H_{30}N_2O_5S \cdot 0.5H_2O$ | | | |
|---|---|---|---|
| | C | H | N |
| calculated (%) | 62.61 | 6.52 | 5.84 |

-continued

| elemental analysis as $C_{25}H_{30}N_2O_5S \cdot 0.5H_2O$ | | | |
|---|---|---|---|
| | C | H | N |
| found (%) | 62.54 | 6.37 | 5.66 |

EXAMPLE 51

N-(2-Indanyl)-4-{N-methyl-N-l(E)-3-(2-chloro-3,4-dihydroxyphenyl)-2-propenoyl]amino}benzenesulfonamide

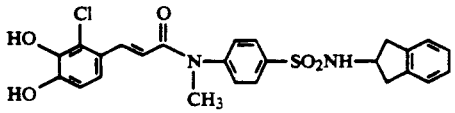

m.p. (°C.): 201~205 (isoPr₂O-AcOEt).

¹H-NMR (90 MHz, DMSO-d₆): δ: 9.25, 8.00 (each 1H, br, D₂O exchange), 7.92 (2H, d, J=8.3Hz), 7.78 (1H, d, J=15.4Hz), 7.57 (2H, d, J=8.3Hz), 7.10 (4H, s), 6.86 (1H, d, J=8.0Hz), 6.64 (1H, d, J=8.0Hz), 6.37 (1H, d, J=15.4Hz), 3.37 (3H, s), 3.20~2.52 (4H, m).

Mass m/e (FD): 498 (M⁺).

| elemental analysis as $C_{25}H_{23}ClN_2O_5S$ | | | |
|---|---|---|---|
| | C | H | N |
| calculated (%) | 60.18 | 4.65 | 5.61 |
| found (%) | 60.24 | 4.81 | 5.62 |

EXAMPLE 52

N-(2-Indanyl)-4-{N-methyl-N-[(E)-3-(3-chloro-4,5-dihydroxyphenyl)-2-propenoyl]amino}benzenesulfonamide

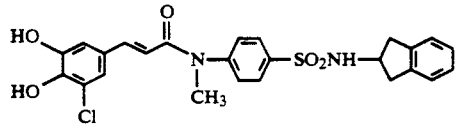

m.p. (°C.): 234~235 (AcOEt-CH₂Cl₂-EtOH).

¹H-NMR (90 MHz, DMSO-d₆) δ: 10.00~9.00, 8.00 (each 1H, br, D₂O exchange), 7.91 (2H, d, J=8.4Hz), 7.55 (2H, d, J=8.4Hz), 7.38 (1H, d, J=15.8Hz), 7.09 (4H, s) 6.98 (1H, brs), 6.79 (1H, brs), 6.29 (1H, d, J=15.4Hz), 3.92 (1H, br), 3.35 (3H, s), 3.16~2.55 (4H, m).

Mass m/e (FD): 498 (M⁺).

| elemental analysis as $C_{25}H_{23}ClN_2O_5S$ | | | |
|---|---|---|---|
| | C | H | N |
| calculated (%) | 60.18 | 4.65 | 5.61 |
| found (%) | 59.88 | 4.76 | 5.52 |

EXAMPLE 53

N-(2-Indanyl)-4-{N-methyl-N-[(E)-3-(2-chloro-4,5-dihydroxyphenyl)-2-propenoyl]amino}benzenesulfonamide -continued

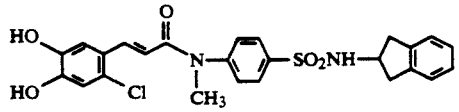

m.p. (°C.): 226~228 (AcOEt-CH₂Cl₂).

¹H-NMR (90 MHz, DMSO-d₆) δ: 8.12 (1H, d, J=6.1Hz, D₂O exchange), 7.92 (2H, d, J=8.4Hz), 7.74 (1H, d, J=15.4Hz), 7.57 (2H, d, J=8.8Hz), 7.10 (4H, s), 6.85 (1H, s), 6.80 (1H, s), 6.30 (1H, d, J=15.4Hz), 3.94 (1H, m), 3.36 (3H, s), 3.20~2.54 (4H, m).

Mass m/e (FD): 498 (M⁺).

| elemental analysis as $C_{25}H_{23}ClN_2O_5S \cdot H_2O$ | | | |
|---|---|---|---|
| | C | H | N |
| calculated (%) | 58.09 | 4.87 | 5.42 |
| found (%) | 58.20 | 4.70 | 5.36 |

EXAMPLE 54

N-(2-Indanyl)-4-{N-methyl-N-[(E)-3-(3-bromo-4,5-dihydroxyphenyl)-2-propenoyl]amino}benzenesulfonamide

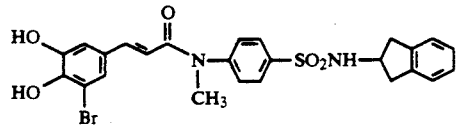

m.p. (°C.): 221~222 (MeOH).

¹H-NMR (90 MHz, DMSO-d₆) δ: 9.90, 9.55 (each 1H, br, D₂O exchange), 8.11 (1H, d, J=6.4Hz, D₂O exchange), 7.92 (2H, d, J=8.8Hz), 7.56 (2H, d, J=8.8Hz), 7.39 (1H, d, J=15.4Hz), 7.10 (4H, s), 7.10 (1H, s), 6.82 (1H, d,J=2Hz), 6.29 (1H, d, J=15.4Hz), 3.92 (1H, m), 3.36 (3H, s), 3.20~2.56 (4H, m).

Mass m/e (FD): 543 (M⁺).

| elemental analysis as $C_{25}H_{23}BrN_2O_5S$ | | | |
|---|---|---|---|
| | C | H | N |
| calculated (%) | 55.25 | 4.27 | 5.16 |
| found (%) | 55.15 | 4.32 | 4.75 |

EXAMPLE 55

N-(2-Indanyl)-4-{N-methyl-N-[(E)-3-(2-bromo-4,5-dihydroxphenyl)-2-propenyl]amino}benzenesulfonamide

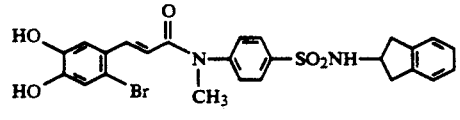

m.p. (°C.): 231~233 (AcOEt-MeOH).

¹H-NMR (90 MHz, DMSO-d₆) δ: 9.56 (2H, brs), 8.08 (1H, brd, J=6Hz), 7.93 (2H, d, J=8.6Hz), 7.71 (1H, d, J=14.3Hz), 7.58 (2H, d, J=8.6Hz), 7.11 (4H, s), 6.97 (1H, s), 6.86 (1H, s), 6.26 (1H, d, J=14.3Hz), 3.92 (1H, brq, J=7Hz), 3.34 (3H, s), 3.01 (2H, dd, J=15.8, 7.0Hz), 2.72 (2H, dd, J=15.8, 7.0Hz).

Mass m/e (FAB): 544, 542 (M⁺); 243, 241, 162 (base); 117.

| elemental analysis as $C_{25}H_{23}BrN_2O_5S$ | | | |
|---|---|---|---|
| | C | H | N |
| calculated (%) | 55.25 | 4.27 | 5.16 |
| found (%) | 54.95 | 4.33 | 4.96 |

EXAMPLE 56

N-(2-Indanyl)-4-{N-methyl-N-l(E)-3-(3,4-dihydroxyphenyl)-2-methyl-2-propenyl]amino}-benzenesulfonamide

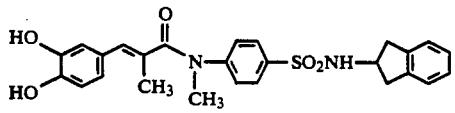

m.p. (°C.): 155~156 (isoPr$_2$O).

$^1$H-NMR (90 MHz, DMSO-d$_6$) δ: 8.98 (2H, br, D$_2$O exchange), 7.96 (1H, br, D$_2$O exchange), 7.80 (2H, d, J=8.4Hz), 7.47 (2H, d, J=8.8Hz), 7.03 (4H, m), 6.73~6.31 (4H, m), 3.80 (1H, m), 3.34 (3H, s), 3.04~2.44 (4H, m), 1.83 (3H, s).

Mass m/e (FAB): 479 (MH$^+$), 282, 177 (base), 149, 131.

| elemental analysis as $C_{26}H_{26}N_2O_5S$ | | | |
|---|---|---|---|
| | C | H | N |
| calculated (%) | 65.25 | 5.48 | 5.85 |
| found (%) | 65.09 | 5.54 | 5.74 |

EXAMPLE 57

N-Cyclopentyl-4-{N-methyl-N-[(E)-3-(3,4-dihydroxyphenyl)-2-propenoyl]amino}benzenesulfonamide

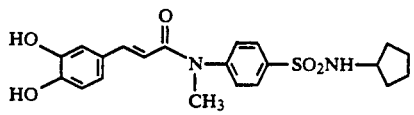

m.p. (°C.): 209~211 (AcOEt-Et$_2$O).

$^1$H-NMR (90 MHz, DMSO-d$_6$) δ: 9.10 (1H, br, D$_2$O exchange), 7.87 (2H, d, J=8.8Hz), 7.52 (2H, d, J=8.4Hz), 7.38 (2H, d, J=15.4Hz), 6.82~6.60 (3H, m), 6.13 (1H, d, J=15.3Hz), 3.32 (3H, s), 3.10~3.60 (1H, m), 1.90~1.10 (8H, m).

Mass m/e (FD): 416 (M$^+$).

| elemental analysis as $C_{21}H_{24}N_2O_5S$ | | | |
|---|---|---|---|
| | C | H | N |
| calculated (%) | 60.56 | 5.81 | 6.73 |
| found (%) | 60.56 | 5.91 | 6.46 |

EXAMPLE 58

N-Cyclohexyl-4-{N-methyl-N-[(E)-3-(3,4-dihydroxyphenyl)-2-propenoyl]amino}benzenesulfonamide

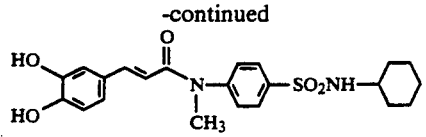

m.p. (°C.): 224~225 (AcOEt-isoPr$_2$O).

$^1$H-NMR (90 MHz, DMSO-d$_6$) δ: 9.16 (2H, brs), 7.88 (2H, d, J=8.6Hz), 7.64 (1H, brd, J=7Hz), 7.52 (2H, d, J=8.6Hz), 7.38 (2H, d, J=15.9Hz), 6.77 (1H, brs), 6.69 (2H, s), 6.13 (1H, d, J=15.9Hz), 3.34 (3H, s), 3.00 (1H, m), 1.8~1.0 (10H, m).

Mass m/e (FD): 430 (M$^+$)

| elemental analysis as $C_{22}H_{26}N_2O_5S$ | | | |
|---|---|---|---|
| | C | H | N |
| calculated (%) | 61.38 | 6.09 | 6.51 |
| found (%) | 61.19 | 6.17 | 6.11 |

EXAMPLE 59

N-(1-Indanyl)-4-{N-methyl-N-[(E)-3-(3,4-dihydroxyphenyl)-2-propenoyl]amino}benzenesulfonamide

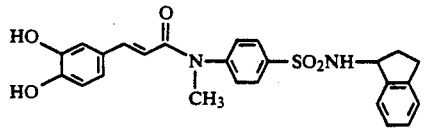

m.p. (°C.): 202~206 (isoPr$_2$O).

$^1$H-NMR (90 MHz, DMSO-d$_6$) δ: 9.10, 8.15 (each 1H, br, D$_2$O exchange), 7.95 (2H, d, J=8.4Hz), 7.56 (2H, d, J=8.3Hz), 7.39 (1H, d, J=15.4Hz), 7.82-7.57 (3H, m), 7.23~7.05 (4H, m), 6.19 (1H, d, J=15.4Hz), 4.62 (1H, m), 3.34 (3H, s), 2.72 (2H, m), 2.30~1.40 (2H, m)

Mass m/e (FD): 465 (MH$^+$).

| elemental analysis as $C_{25}H_{24}N_2O_5S$ | | | |
|---|---|---|---|
| | C | H | N |
| calculated (%) | 64.64 | 5.21 | 6.03 |
| found (%) | 64.69 | 5.32 | 6.05 |

EXAMPLE 60

N-[2-(2-pyridyl)ethyl]-4-{N-methyl-N-[(E)-3-(3,4-dihydroxyphenyl)-2-propenoyl]amino}-benzenesulfonamide

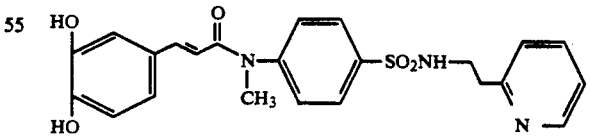

m.p. (°C.) 95~105 (amorphous, isoPr$_2$O-Et$_2$O-AcOEt).

$^1$H-NMR (90 MHz, DMSO-d$_6$) δ: 9.39, 9.07 (each 1H, s, D$_2$O exchange), 8.44 (1H, m), 7.83 (2H, d, J=8.3Hz), 7.51 (2H, d, J=8.4Hz), 7.70~7.40 (1H, m), 7.30~7.05 (3H, m), 6.80~6.50 (3H, m), 6.19 (1H, d, J=15.4Hz), 3.32 (3H, s), 3.40~2.60 (4H, m) .

Mass m/e (FD): 454 (M$^+$)

elemental analysis as $C_{23}H_{23}N_3O_5S \cdot 0.3H_2O$

|  | C | H | N |
|---|---|---|---|
| calculated (%) | 60.12 | 5.19 | 9.14 |
| found (%) | 60.15 | 5.36 | 8.90 |

EXAMPLE 61

N-(2-Thiazolyl)-4-{N-I(E)-3-(3,4-dihyhdroxyphenyl)-2-propenoyl]amino}benzenesulfonamide m.p. (°C.): 219~220 (MeOH).

$^1$H-NMR (90 MHz, DMSO-d$_6$) δ: 10.37, 9.49, 9.21 (each 1H, brs, D$_2$O exchange), 7.78 (4H, s), 7.44 (1H, d, J=16.2Hz), 7.24 (2H, d, J=4.8Hz), 7.03-6.67 (3H, m), 6.80 (1H, d, J=4.8Hz), 6.52 (1H, d, J=16.2Hz).

Mass m/e (FD): 417 (M$^+$).

elemental analysis as $C_{18}H_{15}N_3O_5S_2$

|  | C | H | N |
|---|---|---|---|
| calculated (%) | 51.79 | 3.62 | 10.07 |
| found (%) | 51.39 | 3.61 | 10.03 |

EXAMPLE 62

N-[2-(4,6-Dimethyl)pyrimidyl]-4-{N-[(E)-3-(3,4-dihydroxyphenyl)-2-propenoyl]amino}benzenesulfonamide m.p. (°C.): 174~177 (MeOH).

$^1$H-NMR (90 MHz, DMSO-d$_6$) δ: 10.56 (1H, brs, D$_2$O exchange), 7.96 (2H, d, J=8.8Hz), 7.81 (1H, d, J=8.8Hz), 7.45 (1H, d, J=15.7Hz), 7.09~6.71 (4H, m), 6.57 (1H, d, J=15.7Hz), 2.27 (6H, s).

Mass m/e (FD): 440 (M$^+$).

elemental analysis as $C_{21}H_{20}N_4O_5S \cdot 3H_2O$

|  | C | H | N |
|---|---|---|---|
| calculated (%) | 51.01 | 5.30 | 11.32 |
| found (%) | 50.86 | 4.70 | 10.99 |

EXAMPLE 63

N-(2-Hydroxyethyl)-4-{N-[(E)-3-(3,4-dihydroxyphenyl)-2-propenoyl]amino}benzenesulfonamide m.p. (°C.): 216~219 (MeOH-H$_2$O).

$^1$H-NMR (90 MHz, DMSO-d$_6$) δ: 10.41 (1H, s), 9.60-9.00 (2H, br, D$_2$O exchange), 7.79 (4H, ABq), 7.60~7.36 (2H, m), 7.09~6.68 (3H, m), 6.72 (1H, d, J=16.3Hz), 3.36 (2H, t, J=6.6Hz), 2.78 (2H, q like, J=6.2Hz).

Mass m/e (FD): 378 (M$^+$).

elemental analysis as $C_{17}H_{18}N_2O_6S$

|  | C | H | N |
|---|---|---|---|
| calculated (%) | 53.96 | 4.80 | 7.40 |
| found (%) | 53.91 | 4.81 | 7.02 |

EXAMPLE 64

N-Cyclohexyl-4-{N-[(E)-3-(3,4-dihydroxyphenyl)-2-propenoyl]amino}benzenesulfonamide m.p. (°C.): 120~124 (AcOEt-isoPr$_2$O).

$^1$H-NMR (90 MHz, DMSO-d$_6$) δ: 10.39 (1H, s), 9.49 (1H, s), 9.20 (1H, s), 7.87 (2H, d, J=8.8Hz), 7.73 (2H, d, J=8.8Hz), 7.50 (1H, d, J=7.9Hz), 7.46 (1H, d, J=15.4Hz), 7.02 (1H, brs), 6.96 (1H, brd, J=7.9Hz), 6.77 (1H, d, J=7.9Hz), 6.54 (1H, d, J=15.4Hz), 2.91 (1H, m), 1.8~1.1 (10H, m).

Mass m/e (FD): 416 (M$^+$).

elemental analysis as $C_{21}H_{24}N_2O_5S \cdot 0.3H_2O$

|  | C | H | N |
|---|---|---|---|
| calculated (%) | 59.78 | 5.88 | 6.64 |
| found (%) | 60.06 | 5.91 | 6.12 |

EXAMPLE 65

4-{N-Methyl-N-[(E)-3-(3,4-dihydroxyphenyl)-2-propenoyl]amino}benzenesulfonamide m.p. (°C.): 205~206 (AcOEt-Et$_2$O)

$^1$H-NMR (90 MHz, DMSO-d$_6$) δ: 9.38 (1H, brs, D$_2$O exchange), 9.07 (1H, brs, D$_2$O exchange), 7.86 (2H, d, J=8.3Hz), 7.48 (2H, d, J=8.3Hz), 7.37 (2H, d, J=15.4Hz), 7.40 (2H, s, D$_2$O exchange), 6.69 (3H, m), 6.16 (1H, d, J=15.4Hz), 3.29 (3H, s)

Mass m/e (FD): 348 (M$^+$).

elemental analysis as $C_{16}H_{16}N_2O_5S$

|  | C | H | N |
|---|---|---|---|
| calculated (%) | 55.16 | 4.63 | 8.04 |

| elemental analysis as $C_{16}H_{16}N_2O_5S$ | | | |
|---|---|---|---|
| | C | H | N |
| found (%) | 55.06 | 4.68 | 7.64 |

EXAMPLE 66

4-{N-Isopropyl-N-[(E)-3-(3,4-dihydroxyphenyl)-2-propenoyl]amino}benzenesulfonamide

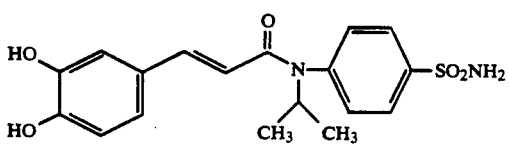

m.p. (°C.): 224~228 (H$_2$O-MeOH).

$^1$H-NMR (90 MHz, DMSO-d$_6$) δ: 9.20 (1H, br, D$_2$O exchange), 7.94 (2H, d, J=7.9Hz), 7.80~7.20 (1H, br, D$_2$O exchange), 7.44 (2H, d, J=7.9Hz), 7.39 (1H, d, J=15.4Hz), 6.67 (3H, s), 5.80 (1H, d, J=15.4Hz), 4.92 (1H, m), 1.05 (6H, d, J=6.5Hz).

Mass m/e (FD): 376 (M+).

| elemental analysis as $C_{18}H_{20}N_2O_5S$ | | | |
|---|---|---|---|
| | C | H | N |
| calculated (%) | 57.43 | 5.36 | 7.44 |
| found (%) | 57.38 | 5.36 | 7.30 |

EXAMPLE 67

N-[2-(N,N-Dimethylamino)ethyl]-4-{N-methyl-N-[(E)-3-(3,4-dihydrophenyl)-2-propenoyl]amino}-benzenesulfonamide hydrochloride

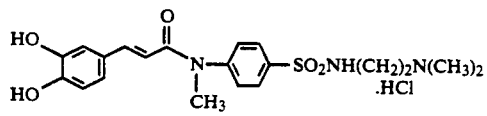

m.p. (°C.): 177~180 (AcOEt).

$^1$H-NMR (90 MHz, DMSO-d$_6$) δ: 10.40 (1H, br, D$_2$O exchange), 9.6~8.8, 8.22 (each 1H, br, D$_2$O exchange), 7.92 (2H, d, J=8.3Hz), 7.56 (2H, d, J=8.3Hz), 7.43 (1H, d, J=15.4Hz), 6.92~6.64 (3H, m), 6.22 (1H, d, J=15.4Hz), 3.34 (3H, s), 3.17 (4H, brs), 2.76 (6H, s).

Mass m/e (FD): 420 (MH+).

| elemental analysis as $C_{20}H_{25}N_3O_5S \cdot HCl \cdot 0.3H_2O$ | | | |
|---|---|---|---|
| | C | H | N |
| calculated (%) | 52.07 | 5.81 | 9.11 |
| found (%) | 52.13 | 5.66 | 8.88 |

EXAMPLE 68

N-methyl-{N-methyl-N-[(E)-3-(3,4-dihydroxyphenyl)-2-propenoyl]amino}benzenesulfonamide

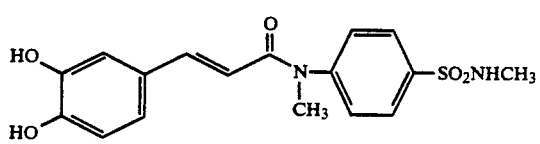

m.p. (°C.): 180~182 (Et$_2$O-AcOEt-EtOH)

$^1$H-NMR (90 MHz, DMSO-d$_6$) δ: 9.20 (2H, br,D$_2$O exchange), 7.85 (2H, d, J=8.4Hz), 7.54 (2H, d, J=8.3Hz), 7.40 (1H, d, J=15.3Hz), 6.84~6.60 (3H, m), 6.21 (1H, d, J=15.3Hz), 3.34 (3H, s), 2.47 (3H, s, D$_2$O sharpen).

Mass m/e (FD): 362 (M+).

| elemental analysis as $C_{17}H_{18}N_2O_5S \cdot 0.1H_2O$ | | | |
|---|---|---|---|
| | C | H | N |
| calculated (%) | 56.06 | 5.04 | 7.69 |
| found (%) | 56.28 | 5.06 | 7.30 |

EXAMPLE 69

N-Isopropyl-4-{N-methyl-N-[(E)-3-(3,4-dihydroxyphenyl)-2-propenoyl]amino}benzenesulfonamide

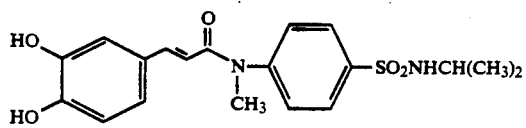

m.p. (°C.): 197~199 (H$_2$O-MeOH).

$^1$H-NMR (90 MHz, DMSO-d$_6$) δ: 10.50~8.50 (1H, br), 7.87 (2H, d, J=8.8Hz), 7.70~7.24 (4H, m), 6.80~6.60 (3H, m), 6.13 (1H, d, J=15.3Hz), 3.32 (3H, s), 0.98 (6H, d, J=7.0Hz).

Mass m/e (FAB): 391 (MH+), 289, 228, 236.

| elemental analysis as $C_{19}H_{22}N_2O_5S$ | | | |
|---|---|---|---|
| | C | H | N |
| calculated (%) | 58.45 | 5.68 | 7.18 |
| found (%) | 58.33 | 5.64 | 6.98 |

EXAMPLE 70

(E)-N-Methyl-N-[4-(4-morpholinyl)sulfonylphenyl]-3-(4-methylsulfonylphenyl)-2-propenamide

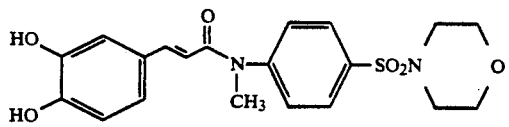

m.p. (°C.): 265↓266 (THF-MeOH).

$^1$H-NMR (90 MHz, DMSO-d$_6$) δ: 9 40, 9.03 (each 1H, br, D$_2$O exchange), 7.81 (2H, d, J=8.4Hz), 7.59 (2H, d, J=8.8Hz), 7.40 (1H, d, J=15.4Hz), 6.86-6.60 (3H, m), 6.22 (1H, d, J=15.4Hz), 3.65 (4H, m), 3.36 (3H, s), 2.91 (4H, m).

Mass m/e (FD): 418(M+).

| elemental analysis as $C_{20}H_{22}N_2O_6S$ | | | |
|---|---|---|---|
| | C | H | N |
| calculated (%) | 57.40 | 5.30 | 6.70 |
| found (%) | 57.24 | 5.37 | 6.52 |

EXAMPLE 71

4-{N-[(E)-3-(3,4-Dimethoxyphenyl)-2-propenoyl]-amino}benzenesulfonamide

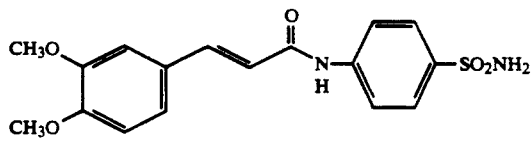

m.p. (°C.): 251~2.52 (CH2Cl2).

1H-NMR (90 MHz, DMSO-d6) δ: 10.40 (1H, br, D2O exchange), 7.82 (4H, s), 7.59 (1H, d, J=16.2Hz), 7.24 (2H, brs, D2O exchange), 7.35~7.11 (2H, m), 7.01 (1H, d, J=8.1Hz), 6.70 (1H, d, J=16.2Hz), 3.34 (6H, s).

Mass m/e (FD): 362 (M+).

| elemental analysis as $C_{17}H_{18}N_2O_5S$ | | | |
|---|---|---|---|
| | C | H | N |
| calculated (%) | 56.34 | 5.01 | 7.73 |
| found (%) | 56.27 | 4.94 | 7.56 |

EXAMPLE 72

4-{N-[(Z)-3-(3,4-Dimethoxyphenyl)-3-(3-Pyridyl)-2-propenoyl]amino}benzenesulfonamide

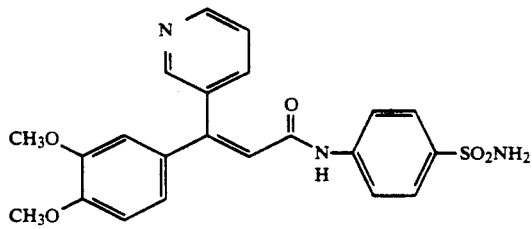

m.p. (°C.): 168~171 (CH2Cl2-EtOH-MeOH)

1H-NMR (90 MHz, DMSO-d6) δ: 10.69 (1H, brs), 8.68 (1H, m), 8.59 (1H, brs), 7.88 (1H, dt, J=7.9, 2.2 Hz), 7.71 (4H, s), 7.22 (2H, brs, D2O exchange), 7.09 (1H, d, J=1.7Hz), 7.01 (1H, d, J=8.4Hz), 6.91 (1H, s), 6.76~6.52 (1H, m), 6.62 (1H, dd, J=8.4, 1.7Hz), 3.78 (6H, s).

Mass m/e (FD): 439 (M+).

| elemental analysis as $C_{22}H_{21}N_3O_5S \cdot 1.7H_2O$ | | | |
|---|---|---|---|
| | C | H | N |
| calculated (%) | 56.21 | 5.23 | 8.94 |
| found (%) | 55.84 | 4.67 | 8.70 |

EXAMPLE 73

4-{N-[(E)-3-(3,4-Dimethoxyphenyl)-3-(3-pyridyl)-2-propenoyl]amino}benzenesulfonamide

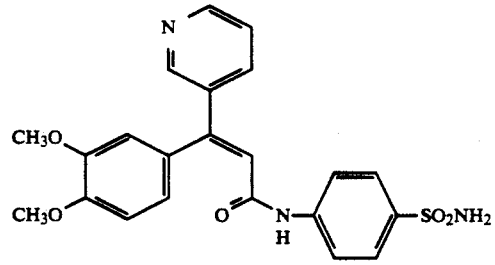

m.p. (°C.): 207~208 (CH2Cl2).

1H-NMR (90 MHz, DMSO-d6) δ: 10-43 (1H, s, D2O exchange), 8.49~8.63 (2H, m), 7.71 (4H, s), 7.64 (1H, dt, J=7.9, 2.2Hz), 7.41 (1H, dd, J=7.9, 3.9Hz), 7.22 (2H, s, D2O exchange), 6.96 (1H, d, J=8.3Hz), 6.82 (1H, d, J=1.7Hz), 6.71 (1H, dd, J=8.3, 1.8Hz), 6.62 (1H, s), 3.77, 3.63 (each 3H, s).

Mass m/e (FAB): 440 (MH+), 397, 289, 268.

| elemental analysis as $C_{22}H_{21}N_3O_5S$ | | | |
|---|---|---|---|
| | C | H | N |
| calculated (%) | 60.13 | 4.82 | 9.56 |
| found (%) | 60.15 | 4.77 | 9.36 |

EXAMPLE 74

4-{N-[(Z)-3-(3,4-Dihydroxyphenyl)-3-(3-pyridyl)-2-propenoyl]amino}benzenesulfonamide hydrobromide

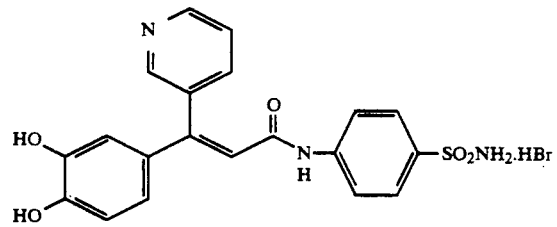

m.p. (°C.): 255~256 (EtOH-MeOH-H2O).

1H-NMR (90 MHz, DMSO-d6) δ: 10.41 (1H, brs, D2O exchange), 9.40, 9.11 (each 1H, s, D2O exchange), 8.51 (2H, dd, J=4.9, 1.8Hz), 8.33 (1H, brd, J=1.8Hz), 7.69 (4H, s), 7.55 (1H, d, J=7.9Hz), 7.38 (1H, dd, J=7.9, 4.9Hz), 7.21 (2H, s, D2O exchange), 6.94~6.52 (4H, m).

Mass m/e (FAB): 412 (MH+), 307, 289, 240.

| elemental analysis as $C_{20}H_{17}N_3O_5S \cdot HBr \cdot 0.7H_2O$ | | | |
|---|---|---|---|
| | C | H | N |
| calculated (%) | 47.57 | 3.84 | 8.32 |
| found (%) | 47.65 | 4.03 | 7.61 |

EXAMPLE 75

4-{N-[(E)-3-(3,4-Dihydroxyphenyl)-3-(3-pyridyl)-2-propenoyl]amino}benzenesulfonamide

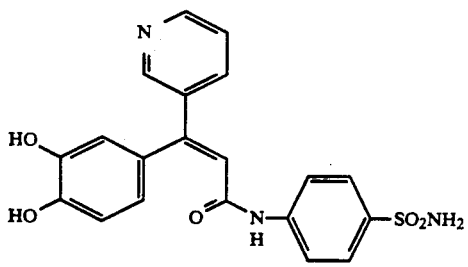

m.p. (°C.): 195~201 (CH$_2$Cl$_2$-H$_2$O).

$^1$H-NMR (90 MHz, DMSO-d$_6$) δ: 10.37 (1H, brs, D$_2$O exchange), 10.00 (1H, br, D$_2$O exchange), 8.72~8.48 (2H, m), 7.82~7.60 (1H, m), 7.70 (4H, s), 7.45 (1H, dd, J=7.9, 3.9Hz), 7.21 (2H, s, D$_2$O exchange), 6.70 (1H, d, J=7.9Hz), 6.61 (1H, d, J=1.8Hz), 6.49 (1H, s), 6.45 (1H, dd, J=7.9, 1.8Hz).

Mass m/e (FD): 411 (M+).

| elemental analysis as C$_{20}$H$_{17}$N$_3$O$_5$S.1.5H$_2$O | | | |
|---|---|---|---|
| | C | H | N |
| calculated (%) | 54.79 | 4.60 | 9.58 |
| found (%) | 54.90 | 4.18 | 8.96 |

EXAMPLE 76

4-{N-[(Z)-3-(3,4-Dihydroxyphenyl)-2-(3-pyridyl)-2-propenoyl]amino}benzenesulfonamide hydrobromide

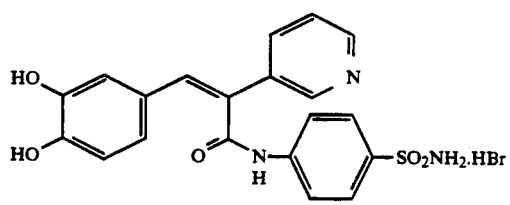

m.p. (°C.): 233~235 (MeOH).

$^1$H-NMR (90 MHz, DMSO-d$_6$) δ: 10.30 (1H, s), 8.89 (2H, m), 8.35 (1H, brd, J=8.0Hz), 8.01 (1H, dd, J=8.0, 4.8Hz), 7.80 (4H, s), 7.71 (1H, s), 7.29 (1H, br, D$_2$O exchange), 6.67 (1H, d, J=8.8Hz), 6.42 (1H, brs), 6.50 (1H, dd, J=8.8, 1.5Hz)

Mass m/e (FD): 411 (M+).

| elemental analysis as C$_{20}$H$_{17}$N$_3$O$_5$S.HBr.0.3H$_2$O | | | |
|---|---|---|---|
| | C | H | N |
| calculated (%) | 48.26 | 3.78 | 8.44 |
| found (%) | 48.45 | 3.94 | 7.86 |

EXAMPLE 77

4-{N-[(E)-3-(3,4-Dihydroxyphenyl)-2-propenoyl]-amino}benzenesulfonamide

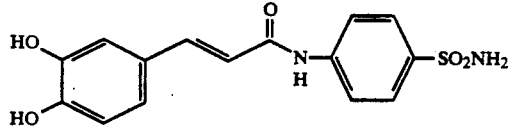

m.p. (°C.): 292~294 (MeOH-H$_2$O).

$^1$H-NMR (90 MHz, DMSO-d$_6$) δ: 9.26 (2H, br, D$_2$O exchange), 7.78 (4H, s), 7.44 (1H, d, J=16.2Hz), 7.20 (3H, br, D$_2$O exchange), 7.10~6.60 (3H, m), 6.51 (1H, d, J=16.2Hz).

Mass m/e (FD): 334 (M+).

| elemental analysis as C$_{15}$H$_{14}$N$_2$O$_5$S | | | |
|---|---|---|---|
| | C | H | N |
| calculated (%) | 53.89 | 4.22 | 8.38 |
| found (%) | 53.64 | 4.13 | 8.15 |

EXAMPLE 78

N-[4-(1-Piperidylmethyl)-benzyl]-4-{N-methyl-N-[(E)-3-(4-methylpulfonylphenyl)-2-propenoyl]-amino}benzenesulfonamide hydrochloride

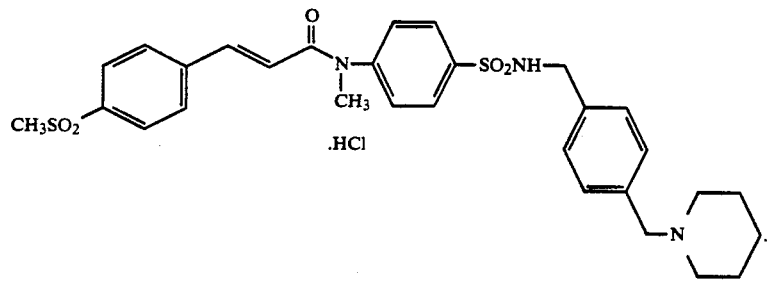

m.p. (°C.): 162~164 (AcOEt-EtOH-MeOH).

$^1$H NMR (400 MHz, CDCl$_3$) δ: 11.30 (1H, brs), 8.12 (2H, d, J=8.2Hz), 7.88 (2H, d, J=8.1Hz), 7.74 (2H, d, J=15.5Hz), 7.70 (1H, t, J=6.3Hz), 7.55 (2H, d, J=8.4Hz), 7.54 (1H, d, J=8.1Hz), 7.40 (2H, d, J=8.2Hz), 7.39 (2H, d, J=7.7Hz), 6.50 (1H, d, J=15.5Hz), 4.15 (2H, d, J=6.3Hz), 4.03 (2H, d, J=5.1Hz), 3.47 (3H, s), 3.41 (2H, d, J=10.8Hz), 3.05 (3H, s), 2.61 (2H, q, J=10Hz), 2.15 (2H, q, J=10Hz), 1.79 (3H, m), 1.36 (1H, q, J=10Hz).

Mass m/e (FAB): 582 (MH+), 372, 203.

| elemental analysis as C$_{30}$H$_{35}$N$_3$O$_5$S$_2$.HCl | | | |
|---|---|---|---|
| | C | H | N |
| calculated (%) | 58.28 | 5.87 | 6.80 |
| found (%) | 57.92 | 5.79 | 6.67 |

EXAMPLE 79

N-[1-[2-(3,4-Dimethoxyphenyl)ethyl]-4-piperidyl]-
4-{N-methyl-N-[(E)-3-(4-methylsulfonylphenyl)-2-
propenoyl]amino}benzenesulfonamide

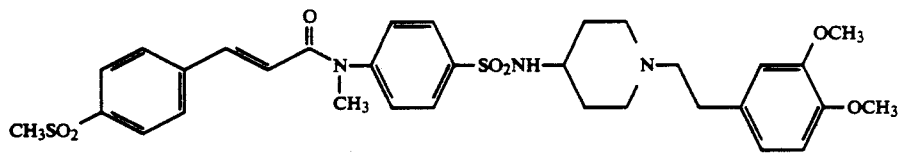

m.p. (°C.): 146~150 (Et2O-AcOEt)
1H-NMR (90 MHz, CDCl3) δ: 7.98 (2H, d, J=8.6Hz), 7.89 (2H, d, J=8.4Hz), 7.74 (1H, d, J=15.6Hz), 7.51 (2H, d, J=8.4Hz), 7.38 (2H, d, J=8.6Hz), 6.81~6.70 (3H, m), 6.47 (1H, d, J=15.6Hz), 4.88 (1H, brd), 3.85 (3H, s), 3.84 (3H, s), 3.47 (3H, s), 3.32 (1H, m), 3.02 (3H, s), 2.82 (2H, m), 2.75 (2H, m), 2.60 (2H, t, like), 2.09 (2H, m), 1.90 (2H, m), 1.62 (2H, m).
Mass m/e (FAB): 642 (MH+), 490, 265, 264, 209, 165 (base).

elemental analysis as C29H35N4O5S2.HCl.H2O

| | C | H | N |
|---|---|---|---|
| calculated (%) | 54.66 | 5.85 | 8.79 |
| found (%) | 54.76 | 5.76 | 8.99 |

EXAMPLE 81

N-[1-[2-(6-Methyl-2-pyridyl)ethyl]-4-piperidyl]-
4-{N-methyl-N-[(E)-3-(4-methylsulfonylphenyl)-2-
propenoyl]amino}benzenesulfonamide

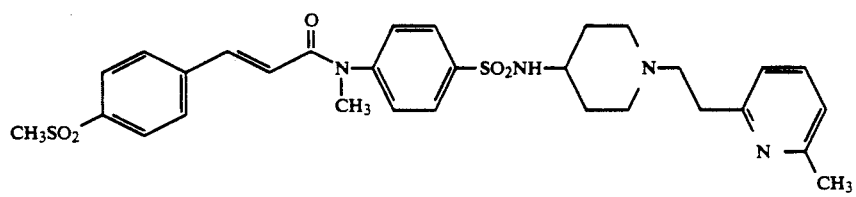

elemental analysis as C32H39N3O7S2.0.5H2O

| | C | H | N |
|---|---|---|---|
| calculated (%) | 59.06 | 6.19 | 6.46 |
| found (%) | 58.94 | 6.04 | 6.06 |

EXAMPLE 80 m.p. (°C.): 161~162 (Et2O-AcOEt).
1H-NMR (400 MHz, CDCl3) δ: 7.96 (2H, d, J=8.6Hz), 7.88 (2H, d, J=8.4Hz), 7.74 (1H, d, J=15.4Hz), 7.50 (2H, d, J=8.4Hz), 7.46 (1H, t, J=8.0Hz), 7.37 (2H, d, J=8.6Hz), 6.95 (2H, d, J=8.2Hz), 6.47 (1H, d, J=15.4Hz), 4.72 (1H, brd), 3.46 (3H,s), 3.30 (1H, m), 3.02 (3H, s), 2.70 (4H, m), 2.49 (3H, s), 2.18 (2H, t, J=7.0Hz), 1.85 (2H, m), 1.56 (2H, m).
Mass m/e (FAB): 597 (MH+), 490, 282, 201 (base), 175.

N-[1-[2-(3-Pyridyl)ethyl]-4-piperidyl]-4-
{N-methyl-N-[(E)-3-(4-methylsulfonylphenyl)-2-
propenoyl]amino}benzenesulfonamide hydrochloride

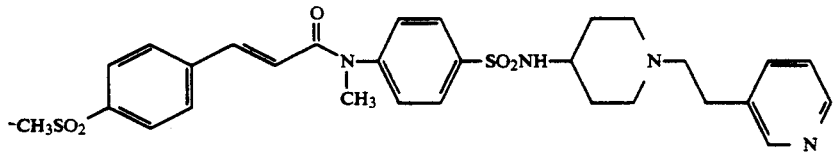

m.p. (°C.): 182~185 (AcOEt)
1H-NMR (400 MHz, DMSO-d6) δ: 8.46 (2H, brd), 8.00 (1H, m), 7.88 (4H, d, J=8.2Hz), 7.77~7.63 (3H, m), 7.62~7.50 (3H, m), 7.35 (1H, brd), 6.70 (1H, brd, J=15Hz), 3.37 (3H, s), 3.19 (3H, s), 3.35~2.85 (9H, m), 1.78 (4H, m)
Mass m/e (FAB): 583 (MH+, 490, 277, 185 (base), 106.

elemental analysis as C30H36N4O5S2 elemental analysis as C30H36N4O5S2

| | C | H | N |
|---|---|---|---|
| calculated (%) | 60.38 | 6.08 | 9.39 |
| found (%) | 60.09 | 6.01 | 9.25 |

EXAMPLE 82

N-[4-[1-Pyrrolidylmethyl)benzyl]-4-{N-methyl-N-

[(E)-3-(4-methylsulfonylphenyl)-2-propenoyl]-amino}benzenesulfonamide

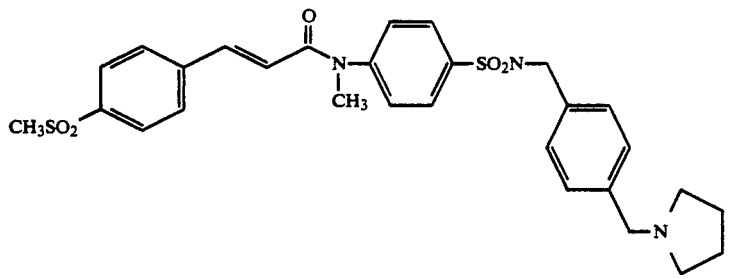

m.p (°C.): 180~182 (AcOEt-CH₂Cl₂).
¹H-NMR (400 MHz, CDCl₃) δ: 7.94 (2H, d, J=8.8Hz), 7.87 (2H, d, J=8.2Hz), 7.74 (1H, d, J=15.4Hz), 7.51 (2H, d, J=8.2Hz), 7.35 (2H, d, J=8.8Hz), 7.26 (2H, d, J=8.2Hz), 7.16 (2H, d, J=8.2Hz), 6.47 (1H, d, J=15.4Hz), 4.20 (2H, s), 3.58 (2H, s), 3.46 (3H, s), 3.03 (3H, s), 2.49 (4H, brs), 1.77 (4H, m).
Mass m/e (FAB): 568 (MH+), 358, 314, 209, 119 (base).

| elemental analysis as C₂₉H₃₃N₃O₅S₂.0.7H₂O | | | |
|---|---|---|---|
| | C | H | N |
| calculated (%) | 60.02 | 5.98 | 7.24 |
| found (%) | 59.97 | 5.73 | 7.08 |

EXAMPLE 83

N-[8-(5,6,7,8-Tetrahydro)quinolyl]-4-{N-methyl-N-[(E)-3-(4-methylsulfonylphenyl)-2-propenoyl]-amino}benzenesulfonamide hydrochloride

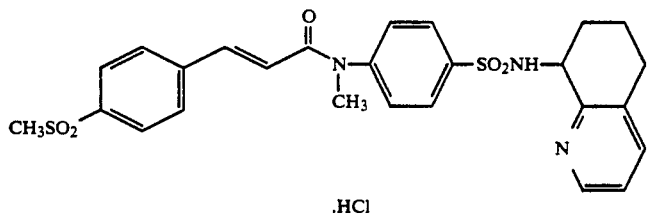

m.p. (°C.): 147~150 (AcOEt-MeOH).
¹H-NMR (90 MHz, DMSO-d₆) δ: 8.62 (1H, d, J=6Hz), 8.55 (1H, brs), 8.13 (1H, d, J=8Hz), 7.98 (2H, d, J=8.8Hz), 7.88~7.60 (6H, m), 7.58 (2H, d, J=8.8Hz), 6.69 (1H, d, J=15.8Hz), 4.78 (1H, m), 3.39 (3H, s), 3.20 (3H, s), 2.80 (2H, m), 1.70 (4H, m).
Mass m/e (FD): 525 (M+).

| elemental analysis as C₂₆H₂₇N₃O₅S₂.HCl.1.5H₂O | | | |
|---|---|---|---|
| | C | H | N |
| calculated (%) | 53.01 | 5.30 | 7.13 |
| found (%) | 52.64 | 5.08 | 7.07 |

EXAMPLE 84

N-Cyclohexyl-4-{N-[(E)-3-(3-fluoro-4-hydroxyphenyl-2-propenoyl)]aminobenzenesulfonamide

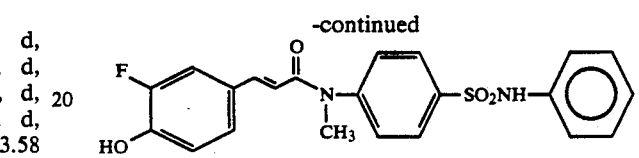

m.p. (°C.): 148~150 (AcOEt).
¹H-NMR (90 MHz, DMSO-d₆) δ: 10.38 (2H, brs), 7.82 (2H, d, J=8.8Hz), 7.69 (2H, d, J=8.8Hz), 7.6~6.9 (4H, m), 6.61 (1H, d, J=15.1Hz), 2.9 (1H, m), 1.8~0.9 (10H, m).
Mass m/e (FD): 418 (M+).

| elemental analysis as C₂₁H₂₃FN₂O₅S | | | |
|---|---|---|---|
| | C | H | N |
| calculated (%) | 60.27 | 5.54 | 6.69 |
| found (%) | 60.27 | 5.61 | 6.50 |

EXAMPLE 85

N-Cyclohexyl-N-methyl-4-{N-[(E)-3-(3-fluoro-4-hydroxyphenyl)-2-propenoyl]amino}benzenesulfonamide

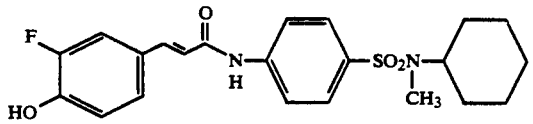

m.p. (°C.): 115~120 (AcOEt-isoPr₂O).
¹H-NMR (90 MHz, DMSO-d₆) δ: 10.42 (2H, brs), 7.85 (2H, d, J=8.8Hz), 7.70 (2H, d, J=8.8Hz), 7.6~6.8 (3H, m), 7.33 (1H, d, J=15.1Hz), 6.62 (1H, d, J=15.1Hz), 3.6 (1H, m), 2.68 (3H, s), 1.8~1.0 (10H, m).
Mass m/e (FD): 432 (M+).

| elemental analysis as $C_{22}H_{25}FN_2O_4S$ | | | |
|---|---|---|---|
| | C | H | N |
| calculated (%) | 61.09 | 5.83 | 6.48 |
| found (%) | 60.89 | 5.98 | 6.24 |

EXAMPLE 86

N-Cycloheptyl-4-{N-methyl-N-[(E)-3-(4-hydroxyphenyl)-2-propenoyl]amino}benzenesulfonamide

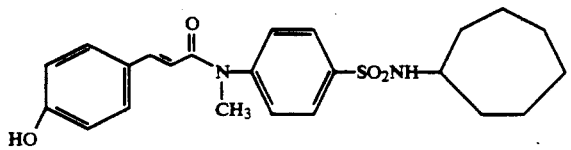

m.p. (°C.): 187~189 (AcOEt-isoPr2O).

$^1$H-NMR (90 MHz, DMSO-d$_6$) δ: 9.80 (1H, br, D$_2$O exchange), 7.87 (2H, d, J=8.3Hz), 7.68 (1H, d, J=7.5Hz, D$_2$O exchange), 7.52 (2H, d, J=8.3Hz), 7.46 (1H, d, J=15.4 Hz), 7.23 (2H, d, J=8.8Hz), 6.70 (2H, d, J=8.4Hz), 6.20 (1H, d, J=15.4Hz), 3.33 (3H, s), 3.16 (1H, s), 3.33 (3H, s), 1.80~1.00 (12H, m).

Mass m/e (FAB): 429 (MH$^+$), 309, 253, 147 (base), 107.

| elemental analysis as $C_{23}H_{28}N_2O_4S$ | | | |
|---|---|---|---|
| | C | H | N |
| calculated (%) | 64.46 | 6.59 | 6.54 |
| found (%) | 64.38 | 6.70 | 6.36 |

EXAMPLE 87

N-Cyclooctyl-4-{N-methyl-N-[(E)-3-(3-fluoro-4-hydroxyphenyl)-2-propenoyl]amino}benzenesulfonamide

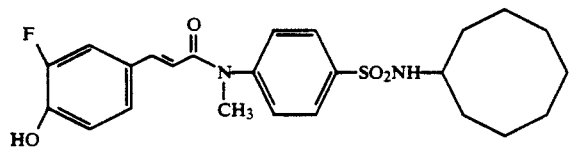

m.p. (°C.): 190~191 (isoPr2O-AcOEt).

$^1$H-NMR (90 MHz, DMSO-d$_6$) δ: 7.87 (2H, d, J=8.7Hz), 7.67 (1H, d, J=7.7Hz, D$_2$O exchange), 7.51 (2H, d, J=8.8Hz), 7.44 (1H, d, J=15.4Hz), 7.35-6.85 (3H, m), 6.27 (1H, d, J=15.4Hz), 3.33 (3H, s), 2.84~1.05 (14H, m).

Mass m/e (FAB): 461 (MH$^+$, base), 351, 271, 165, 137.

| elemental analysis as $C_{24}H_{29}FN_2O_4S$ | | | |
|---|---|---|---|
| | C | H | N |
| calculated (%) | 62.59 | 6.35 | 6.08 |
| found (%) | 62.52 | 6.17 | 6.03 |

EXAMPLE 88

N-Cycloheptyl-4-{N-[(E)-3-{4-(1-imidazolyl)phenyl]-2-propenoyl]amino}benzenesulfonamide

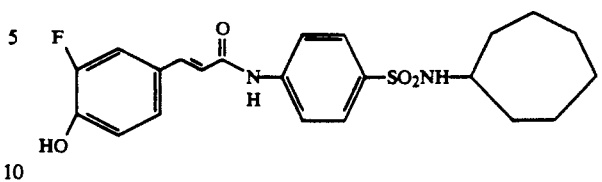

m.p. (°C.): 178~180 (isoPr2O AcOEt).

$^1$H NMR (90 MHz, DMSO-d$_6$) δ: 10.46 (1H, s, D$_2$O exchange), 7.70 (4H, ABq), 7.59-7.20 (5H, m), 6.90 (1H, t like, J=8.0Hz), 6.66 (1H, d, J=15.4Hz), 3.12 (1H, m), 1.80~1.00 (12H, m)

Mass m/e (FAB): 433 (MH$^+$, base), 337, 320, 257, 165, 112.

| elemental analysis as $C_{22}H_{25}N_2O_4S$ | | | |
|---|---|---|---|
| | C | H | N |
| calculated (%) | 61.09 | 5.83 | 6.48 |
| found (%) | 60.96 | 5.73 | 6.34 |

EXAMPLE 89

4-{N-[(E)-3-(3-Acetoxy-4-methoxyphenyl)-2-propenoyl]amino}benzenesulfonamide

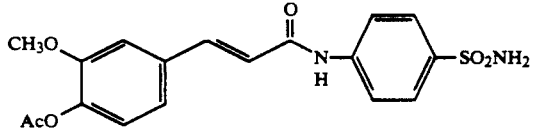

m.p. (°C.): 237~239 (AcOEt).

$^1$H-NMR (400 MHz, DMSO-d$_6$) δ: 7.86 (1H, d, J=8.8Hz), 7.79 (2H, d, J=8.8Hz), 7.63 (1H, d, J=15.7Hz), 7.40 (1H, d, J=1.8Hz), 7.26 (2H, m), 7.17 (1H, d, J=7.9Hz), 6.83 (1H, d, J=15.7Hz), 3.84 (3H, s), 2.27 (3H, s).

Mass m/e (FAB): 391 (MH$^+$), 349, 219, 177 (base), 145.

| elemental analysis as $C_{18}H_{18}N_2O_6S$ | | | |
|---|---|---|---|
| | C | H | N |
| calculated (%) | 55.38 | 4.65 | 7.18 |
| found (%) | 55.46 | 4.58 | 6.94 |

EXAMPLE 90

N-Cycloheptyl-4-{N-[(E)-3-(3,4-dihydroxyphenyl)-2-methyl-2-propenoyl]amino}benzenesulfonamide

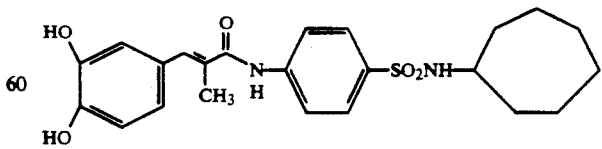

m.p. (°C.): 206~207 (Et2O-EtOH).

$^1$H-NMR (90 MHz, DMSO-d$_6$) δ: 9.26, 9.09 (each 1H, br, D$_2$O exchange), 7.46 (1H, d, J=6.6Hz, D$_2$O exchange), 7.18 (brs), 6.98~6.70 (3H, m), 3.08 (1H, m), 2.10 (3H, s), 1.82~1.00 (12H, m).

Mass m/e (FAB): 445 (MH+), 349, 269, 177, 149, 131.

| elemental analysis C₂₃H₂₈N₂O₅S | | | |
|---|---|---|---|
|  | C | H | N |
| calculated (%) | 62.14 | 6.35 | 6.30 |
| found (%) | 61.99 | 6.41 | 6.20 |

EXAMPLE 91

N-Cyclohexyl-4-{N-methyl-N-[(E)-3-(3,5-dihydroxyphenyl)-2-propenoyl]amino}benzenesulfonamide

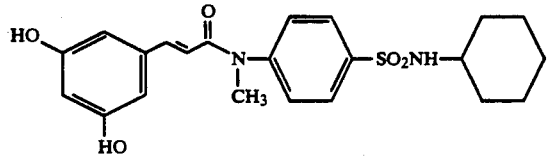

m.p. (°C.): 240~241 (AcOEt-isoPr₂O).

¹H-NMR (90 MHz, DMSO-d₆) δ: 9.29 (2H, s), 7.84 (2H, d, J=8.6Hz), 7.67 (2H, d, J=7.9Hz), 7.48 (2H, d, J=8.6Hz), 7.28 (1H, d, J=15.5Hz), 6.22 (1H, d, J=15.5Hz), 3.34 (3H, s), 2.99 (1H, m), 1.8~1.0 (10H, m).

Mass m/e (FD): 430 (M+).

| elemental analysis as C₂₂H₂₆N₂O₅S | | | |
|---|---|---|---|
|  | C | H | N |
| calculated (%) | 61.38 | 6.09 | 6.51 |
| found (%) | 61.43 | 6.17 | 6.13 |

EXAMPLE 92

N-(2-Indanyl)-4-{N-methyl-N-[(E)-3-(4-hydroxy-3-methoxyphenyl)-2-cyano-2-propenoyl]amino}-benzenesulfonamide

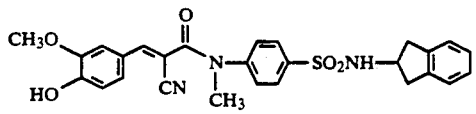

m.p. (°C.): 185~186 (MeOH-THF).

¹H-NMR (90 MHz, DMSO-d₆) δ: 10.19 (1H, br, D₂O exchange), 8.07 (1H, d, J=7.5Hz), 7.83 (2H, d, J=8.4Hz), 7.83 (1H, d, J=8.4Hz), 7.59 (2H, d, J=8.4Hz), 7.59 (1H, d, J=8.4Hz), 7.36 (1H, dd, J=8.2Hz), 7.06 (4H, s), 6.84 (1H, d, J=8.4Hz), 3.68 (3H, s), 3.40 (3H, s), 3.24~2.50 (4H, m).

Mass m/e (FD): 503 (M+).

| elemental analysis as C₂₇H₂₅N₃O₅S | | | |
|---|---|---|---|
|  | C | H | N |
| calculated (%) | 64.40 | 5.00 | 8.35 |
| found (%) | 64.42 | 5.01 | 7.98 |

EXAMPLE 93

4-{N-[(E)-3-(3,4-Dihydroxyphenyl)-2-propenoyl]amino}-5,6,7,8-tetrahydro-1-naphthalenesulfonamide

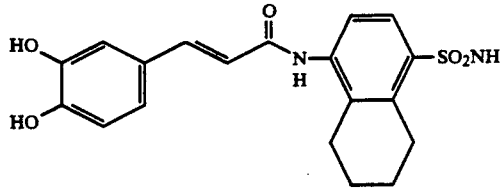

m.p. (°C.): 270~272 (MeOH-H₂O).

¹H-NMR (90 MHz, DMSO-d₆) δ: 9.58 (1H, br, D₂O exchange), 9.29 (1H, brs, D₂O exchange), 9.15 (1H, br, D₂O exchange), 7.69 (2H, s), 7.42 (1H, d, J=15.8Hz), 7.30 (2H, s, D₂O exchange), 7.08~6.60 (4H, m), 3.15 (2H, m), 2.71 (2H, m), 1.75 (4H, m).

Mass m/e (FD): 388 (M+).

| elemental analysis as C₁₉H₂₀N₂O₅S.0.4H₂O | | | |
|---|---|---|---|
|  | C | H | N |
| calculated (%) | 57.68 | 5.30 | 7.08 |
| found (%) | 57.83 | 5.24 | 6.90 |

EXAMPLE 94

N-Isopropyl-4-{N-methyl-N-[(E)-3-(2-chloro-3,4-dihydroxyphenyl)-2-propenoyl]amino}benzenesulfonamide

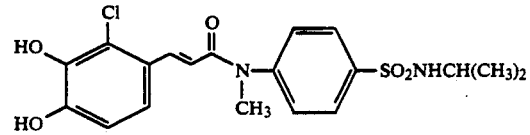

m.p. (°C.): 247~248 (CH₂Cl₂-Et₂O)

¹H-NMR (90 MHz, DMSO-d₆) δ: 10.50~8.50 (2H, br, D₂O exchange), 7.86 (2H, d, J=8.4Hz), 7.76 (1H, d, J=15.4Hz), 7.53 (2H, d, J=8.8Hz), 6.78 (1H, d, J=8.8Hz), 6.63 (1H, d, J=8.8Hz), 6.28 (1H, d, J=15.4Hz), 3.34 (3H, s), 3.20 (1H, m), 0.96 (6H, d, J=6.6Hz).

Mass m/e (FD): 424 (M+).

| elemental analysis as C₁₉H₂₁ClN₂O₅S.0.2H₂O | | | |
|---|---|---|---|
|  | C | H | N |
| calculated (%) | 53.26 | 5.03 | 6.54 |
| found (%) | 53.14 | 5.07 | 6.27 |

EXAMPLE 95

4-{N-[(E)-3-(2-Bromo-4,5-dihydroxyphenyl)-2-propenoyl]amino}benzenesulfonamide

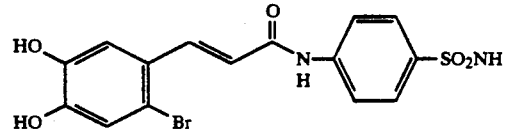

m.p. (°C.): 271~273 (MeOH-H₂O).

¹H-NMR (90 MHz, DMSO-d₆) δ: 7.81 (4H, s), 7.80 (1H, br, D₂O exchange), 7.75 (1H, d, J=15.4Hz), 7.20 (1H, br, D₂O exchange), 7.14 (1H, s), 7.01 (1H, s), 6.58 (1H, d, J=15.4Hz).

Mass m/e (FD): 413 (M+).

| elemental analysis as $C_{15}H_{13}BrN_2O_5S \cdot 0.25H_2O$ | | | |
|---|---|---|---|
| | C | H | N |
| calculated (%) | 43.13 | 3.26 | 6.71 |
| found (%) | 43.32 | 3.42 | 6.31 |

EXAMPLE 96

N-(2-Thiazolyl)-4-{N-[(Z)-3-(3,4-dimethoxyphenyl)-2-(3-pyridyl)-2-propenoyl]amino}-benzenesulfonamide

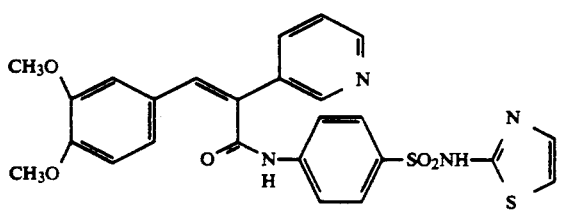

m.p. (°C.): 220~223 (EtOH-MeOH).

$^1$H-NMR (90 MHz, DMSO-$d_6$) δ: 10.22 (1H, brs), 8.52 (1H, dd, J=4.8, 1.8Hz), 8.35 (1H, d like, J=1.8Hz), 7.75 (4H, m, ABq), 7.67 (1H, dt, J=8.0, 1.8Hz), 7.53 (1H, s), 7.42 (1H, dd, J=8.0, 4.8Hz), 7.20 (1H, d, J=4.8Hz), 6.86 (1H, d, J=8.8Hz), 6.77 (1H, d, J=4.8Hz), 6.70 (1H, brd, J=8.8Hz), 6.48 (1H, brs), 3.72 and 3.39 (each 3H, s).

Mass m/e (FD): 522 (M+).

| elemental analysis as $C_{25}H_{22}N_4O_5S_2 \cdot 0.5H_2O$ | | | |
|---|---|---|---|
| | C | H | N |
| calculated (%) | 56.48 | 4.36 | 10.54 |
| found (%) | 56.74 | 4.26 | 10.57 |

EXAMPLE 97

4-{N-[(Z)-3-(3,4-Dimethoxyphenyl)-2-(3-pyridyl)-2-propenoyl]amino}benzenesulfonamide

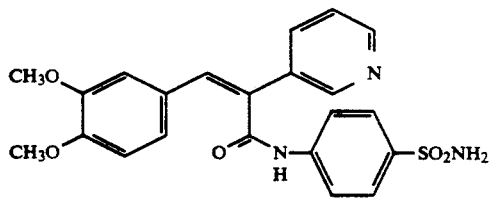

m.p. (°C.): 236~237 (EtOH-MeOH).

$^1$H-NMR (90 MHz, DMSO-$d_6$) δ 10.32 (1H, s), 8.64 (1H, m), 8.44 (1H, brs), 7.80 (4H, m, ABq), 7.83~7.65 (1H, m), 7.62 (1H, s), 7.53 (1H, dd, J=8.1, 4.8Hz), 7.27 (2H, s, $D_2O$ exchange), 6.88 (1H, d, J=8.8Hz), 6.74 (1H, dd, J=8.8, 1.5Hz), 6.51 (1H, d, J=1.5Hz), 3.72 and 3.40 (each 3H, s).

Mass m/e (FD): 439 (M+).

| elemental analysis as $C_{22}H_{21}N_3O_5S$ | | | |
|---|---|---|---|
| | C | H | N |
| calculated (%) | 60.13 | 4.82 | 9.56 |
| found (%) | 60.13 | 4.77 | 9.50 |

EXAMPLE 98

N-(Thiazolyl)-4-{N-[(E)-3-(3,4-dimethoxyphenyl)-2-propenoyl]amino}benzenesulfonamide

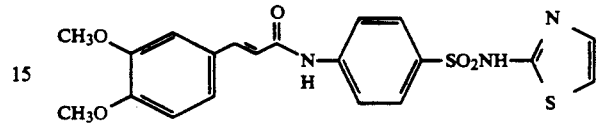

m.p. (°C.): 256~258 ($CH_2Cl_2$).

$^1$H-NMR (90MHz, DMSO-$d_6$) δ: 7.79 (4H, s), 7.57 (1H, d, J=15.6Hz), 7.24 (1H, d, J=4.8Hz), 7.26-7.05 (2H, m), 7.00 (1H, d, J=9.2Hz), 6.81 (1H, d, J=4.8Hz), 6.69 (1H, d, J=15.6Hz), 3.82 and 3.80 (each 3H, s).

Mass m/e (FD): 445 (M+).

| elemental analysis as $C_{20}H_{19}N_3O_5S_2 \cdot 0.25H_2O$ | | | |
|---|---|---|---|
| | C | H | N |
| calculated (%) | 53.38 | 4.37 | 9.34 |
| found (%) | 53.55 | 4.37 | 9.08 |

EXAMPLE 99

4-{N-[(E)-3-(4-Hydroxy-3-methoxyphenyl)-2-propenoyl]amino}benzenesulfonamide

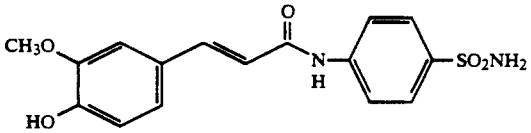

m.p. (°C.): 242~243 (EtOH).

$^1$H-NMR (400 MHz, DMSO-$d_6$) δ: 10.38 (1H, s), 9.53 (1H, s), 7.80 (2H, d, J=8.4Hz), 7.73 (2H, d, J=8.4Hz), 7.49 (1H, d, J=15.9Hz), 7.20 (2H, s), 7.16 (1H, s), 7.04 (1H, d, J=8.1Hz), 6.79 (1H, d, J=8.1Hz), 6.61 (1H, d, J=15.9Hz), 3.79 (3H, s).

Mass m/e (FD): 348 (M+).

| elemental analysis as $C_{16}H_{16}N_2O_5S \cdot 0.3H_2O$ | | | |
|---|---|---|---|
| | C | H | N |
| calculated (%) | 54.43 | 4.69 | 7.92 |
| found (%) | 54.42 | 5.00 | 7.56 |

We claim:

1. A benzenesulfonamide derivative represented by the general formula:

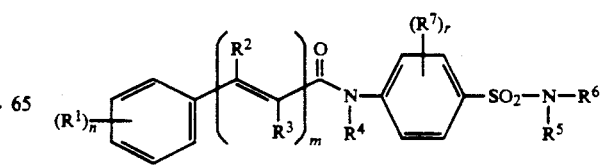

wherein $R^1$ stands for a hydrogen atom, a cyano, nitro or hydroxy group, a halogen atom, a lower alkoxy group, an acyloxy group wherein said acyl moiety is a residue of an organic saturated or unsaturated aliphatic, carbocyclic or heteroaroyl carboxylic acid wherein the hetero atom is oxygen, nitrogen or sulfur, $-SO_2-R^8$ wherein $R^8$ stands for a lower alkyl group, a heteroaryl wherein the hetero atom is a nitrogen, oxygen or sulfur atom, a glycyloxy group, or a group represented by the formula:

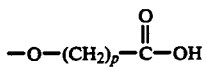

wherein p is an integer of 1 to 3;

n is an integer of 1 to 4;

$R^2$ stands for a hydrogen atom or a pyridyl group;

$R^3$ stands for a hydrogen atom or a lower alkyl, cyano or pyridyl group;

$R^4$ stands for a hydrogen atom or a lower alkyl group;

$R^5$ and $R^6$ may be the same or different from each other and each stand for a hydrogen atom, a lower alkyl group, a group represented by the formula: $-(CH_2)_q-A$ wherein q is an integer of 1 to 4, and A stands for a hydroxyl group, a group represented by the formula:

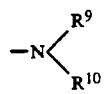

wherein $R^9$ and $R^{10}$ may be the same or different and each stand for a hydrogen atom or a lower alkyl group, a group represented by the formula:

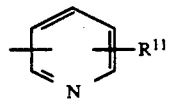

wherein $R^{11}$ stands for a hydrogen atom or a lower alkyl group or a group represented by the formula:

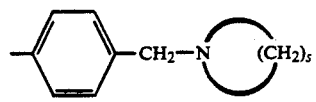

wherein s is an integer of 2 to 5;

$R^5$ and $R^6$ each stand for an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

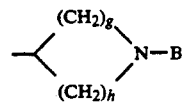

wherein g and h are each an integer of 1 to 4, and B stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group, or, $R^5$ and $R^6$ may be combined together to form a 6- or 7-membered ring which may contain a nitrogen or oxygen atom in addition to the nitrogen atom to which $R^5$ and $R^6$ are bonded, and said 6- or 7-membered ring may be substituted with a lower alkyl, arylalkyl, cycloalkylalkyl or heteroarylalkyl group;

a plurality of $R^7$ groups each independently stand for a hydrogen atom, a lower alkyl group, a lower alkoxy group or a halogen atom; and r is an integer of 1 to 2, provided that when r is 2, the two $R^7$ groups may form a cyclohexenyl or phenyl ring together with two adjacent carbon atoms constituting the benzene ring; and m is an integer of 1 to 2, with the proviso that when $R^1$ is hydrogen, then $R^4$ is not H; and with the proviso that when $R^1$ is halogen and n is 1, $R^4$ is not hydrogen, or a pharmacologically acceptable salt thereof.

2. A benzenesulfonamide derivative or a pharmacologically acceptable salt thereof as set forth in claim 1, wherein $R^1$ is a group represented by the formula: $-SO_2-R^8$ wherein $R^8$ stands for a lower alkyl group, an imidazolyl, cyano or nitro group, a halogen or hydrogen atom or a hydroxyl group.

3. A benzenesulfonamide derivative or a pharmacologically acceptable salt thereof as set forth in claim 1, wherein $R^1$ is a group represented by the formula: $-SO_2CH_3$.

4. A benzenesulfonamide derivative or a each other and each stand for a hydrogen atom, a lower alkyl group, a group represented by the formula: $-(CH_2)_q-A$ an unsubstituted or substituted cycloalkyl group, a bicycloalkyl, tricycloalkyl or azabicycloalkyl group or a group represented by the formula:

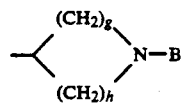

(wherein g and h are each an integer of 1 to 4, and B stands for a lower alkyl group, a substituted or unsubstituted arylalkyl group or a substituted or unsubstituted pyridyl alkyl group), or alternatively, $R^5$ and $R^6$ may be combined together to form a 6 or 7-membered ring pharmacologically acceptable salt thereof as set forth in claim 1, wherein $R^1$ is a $-SO_2CH_3$ group, n is 1 and the $-SO_2CH_3$ group is present at the p-position.

5. A benzenesulfonamide derivative or a pharmacologically acceptable salt thereof as set forth in claim 1, wherein $R^2$ and $R^3$ are each a hydrogen atom and m is 1.

6. A benzenesulfonamide derivative or a pharmacologically acceptable salt thereof as set forth in claim 1, wherein $R^4$ is a methyl group.

7. A benzenesulfonamide derivative or a pharmacologically acceptable salt thereof as set forth in claim 1, wherein $R^4$ is an isopropyl group.

8. A benzenesulfonamide derivative or a pharmacologically acceptable salt thereof as set forth in claim 1, wherein $R^7$ is a hydrogen atom.

9. A benzenesulfonamide derivative or a pharmacologically acceptable salt thereof as set forth in claim 1, wherein $R^5$ is a hydrogen atom or a methyl group and $R^6$ is a group represented by the formula:

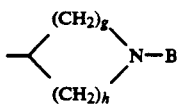

(wherein g and h are each an integer of 1 to 4; and B stands for a lower alkyl group, a substituted or unsubstituted arylalkyl group or a substituted or unsubstituted pyridylalkyl group) or a unsubstituted or substituted cycloalkyl group.

10. A benzenesulfonamide derivative or a pharmacologically acceptable salt thereof as set forth in claim 1, wherein $R^5$ and $R^6$ are combined together to form a 6 or 7 membered ring which may contain a nitrogen or oxygen atom in addition to the nitrogen atom to which $R^5$ and $R^6$ are bonded and which may be substituted with a lower alkyl, arylalkyl, cycloalkylalkyl or heteroarylalkyl group.

11. A benzenesulfonamide derivative or a pharmacologically acceptable salt thereof as set forth in claim 1, wherein $R^5$ is a hydrogen atom or a methyl group and $R^6$ is a group represented by the formula:

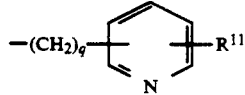

(wherein q is an integer of 1 to 4 and $R^{11}$ stands for a hydrogen atom or a lower alkyl group).

12. A benzenesulfonamide derivative or a pharmacologically acceptable salt thereof as set forth in claim 1, wherein the derivative is N-(1-benzyl-4-piperidyl)-4-{N methyl-N-[(E)-3-(4-methylsulfonyl phenyl-2-propenoyl]amino}benzenesulfonamide.

13. A benzenesulfonamide derivative or a pharmacologically acceptable salt thereof as set forth in claim 1, wherein the derivative is N-[1-(2-phenylethyl)-4-piperidyl-4-{N-methyl-N-[(E)-3-(4- methylsulfonylphenyl)-2-propenoyl]amino}benzenesulfonamide.

14. A benzenesulfonamide derivative or a pharmacologically acceptable salt thereof as set forth in claim 1, wherein the derivative is N-[2-(6-methyl-2-pyridyl)ethyl]-4-{N-methyl-N-[(E)-3-(4-methyl-sulfonylphenyl)-2-propenoyl]amino}benzenesulfonamide.

15. A benzenesulfonamide derivative or a pharmacologically acceptable salt thereof as set forth in claim 1, wherein the derivative is a compound selected from among the following:

N-methyl-N-[2-(6-methyl-2-pyridyl)ethyl]-4-{N-methyl-N-[(E)-3-(4 methylsulfonylphenyl) -2-propenoyl]amino}benzenesulfonamide, E-N-methyl-N-{4-[4-(2-phenylethyl)homopiperazinyl]-sulfonylphenyl}-3-(4-methylsulfonylphenyl)-2-propenamide, (±)-N-[1-(2-pyridylmethyl)-3-hexamethyleneimino]-4-{N-methyl-N-[(E)-3-(4-methylsulfonylphenyl)-2-propenoyl]amino}benzenesulfonamide, (±)-N-[1-benzyl-3-hexamethyleneiminol-4-{N-methyl-N-[(E)-3-(4-methylsulfonylphenyl)-2-propenoyl-]amino}benzenesulfonamide, N-[1-(2-methylpropyl)-4-piperidyl)-4-55 N-methyl-N-[(E)-3-(4-methylsulfonylphenyl)-2-propenoyl]amino} benzenesulfonamide, N-cycloheptyl-4-{N-methyl-N [(E)-3-(4-methylsulfonylphenyl)-2-propenoyl]amino}benzenesulfonamide, N-methyl-N-[2-(2-pyridyl)ethyl]-4-{N-methyl-N-[(E)-3-(4-methylsulfonylphenyl)-2-propenoyl]amino}benzenesulfonamide, N-[2-(2-pyridyl)ethyl]-4-[N-methyl-N-[(E)-3-(4-methylsulfonylphenyl)-2-propenoyl]amino}benzenesulfonamide, (E)-N-methyl-N-[4-(4-benzyl-1-homopiperazinyl)sulfonylphenyl]-3-(4-methylsulfonylphenyl)-2-propenamide, and (E)-N-methyl-N-{4-[4-(2-phenylethyl)piperazinyl]sulfonylphenyl}-3-(4-methylsulfonylphenyl) -2-propenamide.

16. A pharmaceutical composition which comprises an effective phospholipase inhibiting amount of a benzenesulfonamide derivative represented by the general formula:

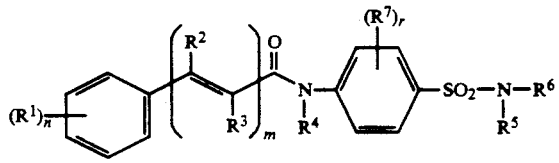

wherein $R^1$ stands for a hydrogen atom, a cyano, nitro or hydroxy group, a halogen atom, a lower alkoxy group, an acyloxy group wherein said acyl moiety is a residue of an organic saturated or unsaturated aliphatic, carbocyclic or heteroaryl carboxylic acid wherein the hetero atom is oxygen, nitrogen or sulfur, —$SO_2$—$R^8$ wherein $R^8$ stands for a lower alkyl group, a heteroaryl wherein the hetero atom is a nitrogen, oxygen or sulfur atom, a glycyloxy group, or a group represented by the formula:

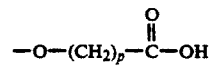

wherein p is an integer of 1 to 3;
n is an integer of 1 to 4;
$R^2$ stands for a hydrogen atom or a pyridyl group;
$R^3$ stands for a hydrogen atom or a lower alkyl, cyano or pyridyl group;
$R^4$ stands for a hydrogen atom or a lower alkyl group;
$R^5$ and $R^6$ may be the same or different from each other and each stand for a hydrogen atom, a lower alkyl group, a group represented by the formula: —$(CH_2)_q$—A wherein q is an integer of 1 to 4, and A stands for a hydroxyl group, a group represented by the formula:

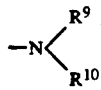

wherein $R^9$ and $R^{10}$ may be the same or different and each stand for a hydrogen atom or a lower alkyl group, a group represented by the formula:

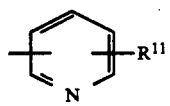

wherein $R^{11}$ stands for a hydrogen atom or a lower alkyl group or a group represented by the formula:

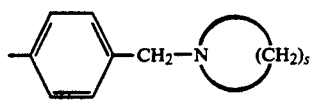

wherein s is an integer of 2 to 5;
$R^5$ and $R^6$ stand for an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrogen group made of two or three rings, respectively, with at least two carbon atoms being common to each ring, or an azabicycloalkyl group which is a bicycloalkyl group as described above in which one carbon atom is replaced by a nitrogen atom or a group represented by the formula:

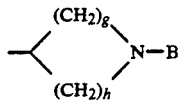

wherein g and h are each an integer of 1 to 4, and B stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group, or,
$R^5$ and $R^6$ may be combined together to form a 6- or 7-membered ring which may contain a nitrogen or oxygen atom in addition to the nitrogen atom to which $R^5$ and $R^6$ are bonded, and said 6- or 7-membered ring may be substituted with a lower alkyl, arylalkyl, cycloalkylalkyl or heteroarylalkyl group;
a plurality of $R^7$ groups each independently stand for a hydrogen atom, a lower alkyl group, a lower alkoxy group or a halogen atom; and r is an integer of 1 to 2, provided that when r is 2, the two $R^7$ groups may form a cyclohexenyl or phenyl ring together with two adjacent carbon atoms constituting the benzene ring; and
m is an integer of 1 to 2, with the proviso that when $R^1$ is halogen and n is 1, $R^4$ is not hydrogen, and with the proviso that when $R^1$ is hydrogen, then $R^4$ is not hydrogen, or a pharmacologically acceptable salt thereof;
and a pharmaceutically acceptable carrier.

17. A method of treating or preventing diseases associated with activation of phospholipase $A_2$, which comprises administering to a patient in need of such treatment, a benzenesulfonamide derivative represented by the general formula:

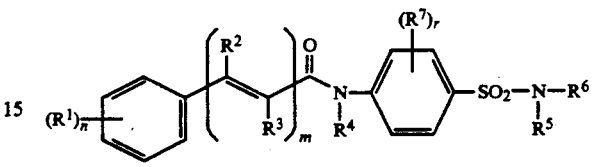

wherein $R^1$ stands for a hydrogen atom, a cyano, nitro or hydroxy group, a halogen atom, a lower alkoxy group, an acyloxy group wherein said acyl moiety is a residue of an organic saturated or unsaturated aliphatic, carbocyclic or heteroaroyl carboxylic acid wherein the hetero atom is oxygen, nitrogen or sulfur, $-SO_2-R^8$ wherein $R^8$ stands for a lower alkyl group, a heteroaryl wherein the hetero atom is a nitrogen, oxygen or sulfur atom, a glycyloxy group, or a group represented by the formula:

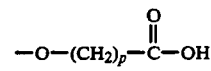

wherein p is an integer of 1 to 3;
n is an integer of 1 to 4;
$R^2$ stands for a hydrogen atom or a pyridyl group;
$R^3$ stands for a hydrogen atom or a lower alkyl, cyano or pyridyl group;
$R^4$ stands for a hydrogen atom or a lower alkyl group;
$R^5$ and $R^6$ may be the same or different from each other and each stand for a hydrogen atom, a lower alkyl group, a group represented by the formula: $-(CH_2)_q-A$ wherein q is an integer of 1 to 4, and A stands for a hydroxyl group, a group represented by the formula:

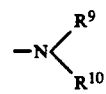

wherein $R^9$ and $R^{10}$ may be the same or different and each stand for a hydrogen atom or a lower alkyl group, a group represented by the formula:

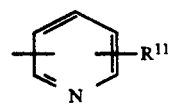

wherein $R^{11}$ stands for a hydrogen atom or a lower alkyl group or a group represented by the formula:

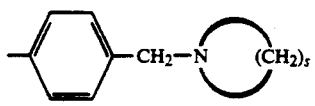

wherein s is an integer of 2 to 5;

$R^5$ and $R^6$ stand for an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrogen group made of two or three rings, respectively, with at least two carbon atoms being common to each ring, or an azabicycloalkyl group which is a bicycloalkyl group as described above in which one carbon atom is replaced by a nitrogen atom or a group represented by the formula:

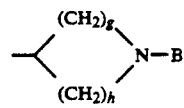

wherein g and h are each an integer of 1 to 4, and B stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group, or, $R^5$ and $R^6$ may be combined together to form a 6- or 7-membered ring which may contain a nitrogen or oxygen atom in addition to the nitrogen atom to which $R^5$ and $R^6$ are bonded, and said 6- or 7-membered ring may be substituted with a lower alkyl, arylalkyl, cycloalkylalkyl or heteroarylalkyl group;

a plurality of $R^7$ groups each independently stand for a hydrogen atom, a lower alkyl group, a lower alkoxy group or a halogen atom; and r is an integer of 1 to 2, provided that when r is 2, the two $R^7$ groups may form a cyclohexenyl or phenyl ring together with two adjacent carbon atoms constituting the benzene ring; and m is an integer of 1 to 2, or a pharmacologically acceptable salt thereof.

* * * * *

UNITED STATES PATENT AND TRADEMARK OFFICE
CERTIFICATE OF CORRECTION

PATENT NO. : 5 281 626
DATED : January 25 1994
INVENTOR(S) : Oinuma H. et al.

It is certified that error appears in the above-indentified patent and that said Letters Patent is hereby corrected as shown below:

In the Claims:

Col. 96, lines 43-64, delete claim 4 and replace with claim 4 as allowed in the above-referenced application:

--4. A benzenesulfonamide derivative or a pharmacologically acceptable salt thereof as set forth in claim 1, wherein $R^1$ is a $-SO_2CH_3$ group, n is 1 and the $-SO_2CH_3$ group is present at the p-position.--

Signed and Sealed this

Sixth Day of June, 1995

*Attest:*

BRUCE LEHMAN

*Attesting Officer*    *Commissioner of Patents and Trademarks*